United States Patent [19]

Thompson

[11] Patent Number: 5,783,182
[45] Date of Patent: Jul. 21, 1998

[54] METHOD FOR IDENTIFYING METASTATIC SEQUENCES

[75] Inventor: Timothy C. Thompson, Houston, Tex.

[73] Assignee: Baylor College of Medicine, Houston, Tex.

[21] Appl. No.: 594,031

[22] Filed: Jan. 30, 1996

Related U.S. Application Data

[60] Provisional application No. 60/006,838 Nov. 16, 1995.

[51] Int. Cl.$^6$ .................. C12N 5/00; C12N 15/63; C12N 15/79; A61K 48/00
[52] U.S. Cl. .................. 424/93.21; 435/375; 435/6; 435/172.3; 435/69.1; 935/62; 935/34; 800/2
[58] Field of Search .................. 435/320.1, 240.2, 435/6, 7.2, 240.21, 7.9; 935/62, 52, 55, 57, 34, 66, 70, 71, 33, 65; 424/93.1, 93.2, 9.1; 800/2

[56] References Cited

U.S. PATENT DOCUMENTS

| | | |
|---|---|---|
| 4,317,818 | 3/1982 | Benson et al. |
| 4,925,835 | 5/1990 | Heston |
| 5,116,615 | 5/1992 | Gokcen et al. |

FOREIGN PATENT DOCUMENTS

| | | |
|---|---|---|
| WO 8603226 | 6/1986 | WIPO |
| WO 9428129 | 12/1994 | WIPO |
| WO 9519369 | 7/1995 | WIPO |
| WO 9630389 | 10/1996 | WIPO |

OTHER PUBLICATIONS

Xiong et al. "Human D–Type Cyclin," Cell, vol. 65: 691–699, May 17, 1991.
Manam et al. "Dose related changes in the profile of ras mutations in chemically induced CD–1 mouse liver tumors," Carcinogenesis, vol. 16 (5): 1113–1119, May 1995.
Blok, et al. "Isolation of cDNA's that are differentially expressed between androgen–dependent and androgen independent prostate carcinoma cells using differential display PCR," Prostate, vol. 26(4): 213–224, Apr. 1995.
Wu et al. "Identification of a human hepatocellular carcinoma–associated tumor suppressor gene by differential display polymerase chain reaction," Life Sciences, vol. 57(11): 1077–1085, Nov. 1995.
Schneider et al. "7,12–Dimethylben[a]anthracene–Induced Mouse Keratinocyte Malignant Transformation Independent of Harvey ras Activation," J. of Investigative Dermatology, vol. 101 (4): 595–599, Oct. 1993.
Fingert et al. "In vivo model for differentiation therapy of leukemia and solid tumors," National Institutes of Health Publication, 84–2635, Serono Symposia Publications from Rven Press, pp. 277–286, 1984.
Taber's Cyclopedic Medical Dictionary, F.A. Davis Company, Philadelphia, PA, edited by Vardara et al., 1993.
Gudas, "Retinoids, Retinoid–responsive Genes, Cell Differentiation, and Cancer"; Cell Growth & Differentiation, vol. 3, pp. 655–662, Sep. 1992.

Mokulis, et al., "Screening for Prostate Cancer: Pros, Cons, and Reality"; Cancer Control, pp. 15–21, Jan./Feb. 1995.
Merz, et al., "Elevated Transforming Growth Factor–$\beta$1 and $\beta$3 mRNA Levels are Associated with ras+myc–Induced Carcinomas in Reconstituted Mouse Prostate: Evidenced for a Paracrine Role during Progression", Molecular Endocrinology, vol. 5, No. 4, (1991) pp. 503–513.
Poster Session Abstracts; First SPORE Investigators' Meeting, "The Role of Retinoids in Prostate Cancer Chemoprevention" Jul. 18–20, 1993, p. 30.
Slawin, et al., "Dietary Fenretinide, a Synthetic Retinoid, Decreases the Tumor Incidence and the Tumor Mass of ras+myc–induced Carcinomas in the Mouse Prostate Reconstitution Model System", Cancer Research, vol. 53, pp. 4461–4465, Oct. 1, 1993.
Thompson, et al., "Transgenic Models for the Study of Prostate Cancer",(Supplement) Cancer, vol. 71, No. 3, Feb. 1, 1993, pp. 1165–1171.
Donehower, et al, "Mice deficient for p53 are developmentally normal but susceptible to spontaneous tumours", Articles, Nature, vol. 356, Mar. 19, 1992, pp. 215–221.
Thompson, et al., "Loss of p53 function leads to metastasis in ras+myc–initiated mouse prostate cancer", Oncogene (1995) vol. 10, pp. 869–879.
Macoska, et al., "Loss of the 17p Chromosomal Region in a Metastatic Carcinoma of the Prostate", The Journal of Urology, vol. 147, Apr. 1992, pp. 1142–1146.
Taylor, et al., "Evidence for synergistic interactions between ras, myc and a mutant form of p53 in cellular transformation and tumor dissemination", Oncogene, Feb. 10, 1992, pp. 1383–1390.
Hall, et al., "Adenylate Kinase: An Oncodevelopmental Marker in an Animal Model for Human Prostatic Cancer", Clinical Chemistry, vol. 31, No. 10, (1985), pp. 1689–1691.
Thompson, et al., Multistage Carcinogenesis Induced by ras and myc Oncogenes in a Reconstituted Organ, Cell, vol. 56, pp. 917–930, Mar. 24, 1989.
Slawin, et al., American Urological Association, Inc., Annual Meeting—San Antonio, Oct. 1, 1992, Dietary Retinoids Decrease the Incidence and Increase Lymphocytic Infiltration of ras+myc Induced Carcinomas in the Mouse Prostate Reconstitution Model System.

(List continued on next page.)

Primary Examiner—Jasemine C. Chambers
Assistant Examiner—Karen M. Hauda
Attorney, Agent, or Firm—James Remenick Baker & Botts, L.L.P.

[57] ABSTRACT

The invention relates to methods for the identification of metastatic sequences. Cells from a cell line or an animal tissue are treated to form a cell line predisposed to metastasis. Treated cells are implanted in an animal of a primary site and incubated for a period of time sufficient for the cells to proliferate and develop metastases at secondary sites. Expressed sequences from cells at the primary and secondary sites are amplified by differential display polymerase chain reaction and compared. Differentially expressed sequences are identical and can be cloned and sequenced. These sequences can be used as probes in the diagnosis of metastatic disorders, as probes to isolate metastatic sequences and as a therapeutic agent.

42 Claims, 63 Drawing Sheets

OTHER PUBLICATIONS

Thompson, et al., "Transforming Growth Factor β1 as a Biomarker for Prostate Cancer", *Journal of Cellular Biochemistry*, Supplement 16H: pp. 54–61 (1992).

Thompson, et al., "Genetic Predisposition and Mesenchymal–Epithelial Interactions in ras+myc–Induced Carcinogenesis in Reconstituted Mouse Prostate" *Molecular Carcinogenesis*, vol. 7, pp. 165–179 (1993).

Bookstein et al., "p53 Is Mutated in a Subset of Advanced–Stage Prostate Cancers[1]", *Cancer*, vol. 53, pp. 3369–3373, Jul. 19, 1993.

Carter, et al. "Prediction of Metastatic Potential in an Animal Model of Prostate Cancer: Flow Cytometric Quantification of Cell Surface Charge", *The Journal of Urology*, vol. 142, pp. 1338–1341, Nov. 1989.

Fox, et al., "p53 And c–myc Expression in Stage A1 Prostatic Adenocarcinoma: Useful Prognostic Determinants?", *The Journal of Urology*, vol. 150, pp. 490–494, Aug. 1993.

Einstein, "Hormonal Therapy for Prostate Cancer—When to Use It", *Cancer Control*, Jan./Feb. 1995, pp. 32–36.

Thompson, et al., "Loss of p53 Function Leads to Metastasis in ras+myc–Initiated Mouse Prostate Cancer", Abstract for Fogarty International Meeting, Jun. 26–28, 1995.

International Search Report, completed May 30, 1997.

Welch, Danny R., et al. "Transforming growth factor β stimulates mammary adenocarcinoma cell invasion and metastatic potential", *Proc. Natl. Acad. Sci. USA*, vol. 87, pp. 7678–7682. Oct. 1990.

Thompson, Timothy C., et al. "Multistage Carcinogenesis Induced by ras and myc Oncogenes in a Reconstituted Organ", *Cell*, vol. 56, pp. 917–930. Mar. 24, 1990.

Liang, Peng, et al. "Differential Display and Cloning of Messenger RNAs from Human Breast Cancer versus Mammary Epithelial Cells", *Cancer Research*, 52, pp. 6966–6968. Dec. 15, 1992.

*Proceedings of the American Association for Cancer Research*, vol. 36, p. 266 #1589. Mar. 1995.

Liang, Peng, et al. "Differential Display of Eukaryotic Messenger RNA by Means of the Polymerase Chain Reaction", *Science*, vol. 257, pp. 967–971. Aug. 14, 1992.

Wood, David P., Jr., et al., "Sensitivity of Immunohistochemistry and Polymerase Chain Reaction in Detecting Prostate Cancer Cells in Bone Marrow", *The Journal of Histochemistry and Cytochemistry*, vol. 42, No. 4, pp. 505–511. 1994.

CL-1#2

AATTTTTTTTTCGACGGCCCAACGGAATTTTTTTTTCGACGGCCCAACGGAATTTTT
TTTTTCGACGGCCCAACGGGAATTCGGCTTAGCTAAGGTCACCCAGACTTCATGGACT
TGTCTATTTTCTTGCCCAAAGGGATAGTTCCTCAGGTATTTGGGGACAGCATTCACCTC
TTGCAGGAGCTATGCCTGTGTGTTTGTGCTAAGTTGATACTTTCTGCGATGATCTCAC (SEQ ID NO. 31)

CL-10#3

TACCATCGGAGAAAGAAGACCAAGCAAGGCTCAGGCAGCCACCGCCTGCTTCGCACT
GAGCCTCCTGACTCAGACTCAGAGTCCAGCACAGACGAAGAGGAATTTGGAGAATTG
GAAATCGCTCTCGTTTTGTCAAGGGAGACTATCCCGATGCTGCAAGATCTGCTGTCCCT
CTGGCCTTTGTCATCCTCGCGCCTGCGTTGTGGCCTCTGTGGGCTTGGTGTGGAGCAAA
TGGCTCTCAAGGAGGACTGAGTCTCAAGGAAATT (SEQ ID NO. 32)

CL-11A#5

AGCTAAGGTCAGGAGGTGTCTGAAGAATTGGCTGATGCATGGCAGGGATGTTGTTGAC
CTGCTTTTAGAACAATACTTCCATTTAATTATAGCATATCTTATGTGTGTATTAAAGCA
GAGCCGATCTGGTGGGGCTCATTAAGTAAATGTACTTACTGCAAAAGGTTCAACTGGT
GACCCCAGTTTTCCCCAGAAGCAATATGATAGGACAGAGGCGACTCCTGCAAGTTGTC
TCAGACTTCACACATACATTGTGACATTCTCTGAGCATGTGCACTGTACATGATATGAC
ACTATCAA (SEQ ID NO. 33)

CL-11C#2

AGCTAAGGTCCACTACCTTGTGAAGATGTATAAACACCTGAAATGTAGAAGCGATCCG
TATGTCAAGATCGAGGGGAAGGACGCTGACGACTGGCTGTGTGTGGACTTTGGGAGTA
TGGTGATCCATTTGATGCTTCCAGAAACCAGAGAAACCTATGAATTAGAGAAACTATG
GACTCTACGTTCTTTTGATGACCTTAGCTAAGCCGAATCAGCACACTGGCGGCGTTACT
AGTGGATCGAGCTCGTACAGCTGATGCATAGCTTGAGTATCTATAGGTTACTAATAGC
TGGCTATCATGTCAAGCGTTC (SEQ ID NO. 34)

AGCTAAGGTCAAAATAAAAGCTCAAGATGACATCAGTCCCATTTGTCCTAAGTCCTGG
TGTTGTATGGATGGTAAGCAGCAGCCAATTATGGTGACAGGTGATAGATCCAATTTGT
TAACATTTCTCCATCTCTAAGCCATCCTTAAAGAAAATCATGAATGGAGTCACACCAT
CTTCACGGTAGTCCAGGAGAGCAACCATACCATCTGGATTCATGTTTCACCAATAAAA
ACTGGTAGTTATTGAATTAGCAAGGATGTGCTACTCTCTGCAGCTCAGC (SEQ ID NO. 35)

CL-13#1

AGCTAAGGTCTCATGCAATGGAACTTAATTCTTAGAACTGTAAGAATTACATCAAACA
TAAAAGCCTCCCTATTAATGTAGTCCACAAAACTGGCAGGTATATATGCCTTCTGAAT
TTGTCTCCAGTGACTTTGGTAAATCTAACTAAATTTTTAAAAATTCTTAATGAATTTAT
CGTCAACAACAACCACCTCTTGGAAAATTAACCCTTGCAGTGTCTGTGTTAGACTCAG
AAGTCAA (SEQ ID NO. 36)

CL-14#4

GAATTCGGCTTAGCTAAGGTCAGCGTGAAGTTTAAGCAGACATGAGTCTGAAACAGTC
TCATGACACATCTGATAGGATTTTTTAAGACTGCCTGGCTTAGTCTTACTGCTGTTAGT
GTATATTAGGTGTTGTACACATTATAAAGAAAATTATGTCTCATTATCTTGTTTAAGTC
AAGGAAAATAGAGAACTTTGGTCAAAT (SEQ ID NO. 37)

CL-2#2

GAATTCGGCTTAGCTAAGGTCAGCGTGAAGTTTAAGCAGACATGAGTCTGAAACAGTC
TCATGACACATCTGATAGGATTTTTTAAGACTGCCTGGCTTAGTCTTACTGCTGTTAGT
GTATATTAGGTGTTGTACACATTATAAAGAAAATTATGTCTCATTATCTTGTTTAAGTC
AAGGAAAATAGAGAACTT (SEQ ID NO. 38)

CL-2#3

GAATTCGGCTTAGCTAAGGTCAAAATACACGGATTGCAATCACTTTTCTAAACAAAAG
AAACAAAGTAACTGCTGAGGTTAGCAAAGATGAGTTCTCGTCATACTGCCTTGTACTG

FIG. 12B

TTTTGTGAACTGTGTTATTAAAAATCTGAGCTTAACAAAATCTTTACAAGTCACCTCAT

GAAAACAGCATTTGGCCAATAAGAGTTTAATTCCACACCAGTGAGACCTTAGCCT (SEQ ID NO. 39)

CL-2#4

GAATTCGGCTTTCTGCGATCCACTCTTTGAAGCTATTGGCAAGATATTCAGCAACATCC

GCATCAGCACGCAGAAAGAGATATGAGGGACATTTCAAGGATGAAAGGTTTTTTTCCC

CCCTTACTATTTCCTTGGTGCCAATTCCAAGTTGCTCTCGCAGCAGCAAATTTATGAAT

GGTTTGTCTTGATCAAGAACAAAGAATTCATTCCACCATTCTCATATATACTACTTTC

TCTTCTT (SEQ ID NO. 40)

CL-3#1

GAATTCGGCTTTCTGCGATCCACTCTTTGAAGCTATTGGCAAGATATTCAGCAACATCC

GCATCAGCACGCAGAAAGAGATATGAGGGACATTTCAAGGATGAAAGGTTTTTTTCCC

CCCTTACTATTTCCTTGGTGCCAATTCCAAGTTGCTCTCGCAGCAGCAAATTTATGAAT

GGTTTGTCTTGATCAAGAACAAAGAATTCATTCCACCATTCTCATATATCTACGTCTCT

TCTAG (SEQ ID NO. 41)

CL-4#1

GAATTCGGCTTTCTGCGATCCTAGAGCAGGTAAGTGAAGAAGGCCAGTAAGTTTTAAG

GATGGCCTTGTTGCCTTCTATCAAGTTCTCTGGGACTTTGTAATTTTGATTACTACTATT

GATACATGGTTATGGTCAGAAGGCCTCTTCTCCCTT (SEQ ID NO. 42)

CL-4#2

AGCTAAGGTCCGGACTCTATGGCATGACCCCAAAAACATTGGCTGGAAAGATTACACT

GCCTACAGGTGGCACCTGATTCACAGGCCTAAGACAGGCTACATGAGAGTCTTAGTGC

ATGAAGGAAAGCAAGTCATGGCTGACTCAGGACCAATTTATGACCAAACCTACGCTG

GTGGACGGCTGGGCTGTTTGTCTTCTCCAAGAGATGGTCTATTCTCGGACCTCAAGTAT

GAGTGCAGAGATGCTAGAGAGCAGGCTCAGTCTCAGCA (SEQ ID NO. 43)

TGACCATCGAGTGCATCAGCCTCATCGGGCTGGCCGTCGGGAAGGAGAAATTCATGCA
GGATGCTTCAGATGTGATGCAGCTATTGTTGAAGACACAGACAGACTTCAATGATATG
GAAGATGACGACCCCAGATTTCTTACATGATCTCAGCATGGGCCAGGATGTGCAAAA
TCTTGGGAAAGAATTCCAGCAGTACCTTCCCGTGGTTATGGGGCCGCTGATGAAGACT
GCTTCAATTAAGTCCTGAGTGCCTCTAGACACCAGGACATGAGATATGAGGTA (SEQ ID NO. 44)

CL-6#2

TGACCATCGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGATGCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT (SEQ ID NO. 45)

CL-7#4

TGACCATCGAACACCCCAACACTCTCCACTACCTGCCATTTCTTCCAGCCTTATCCACA
CCACCCCGTTTCTCCTGAAGACTGATTTGCTTAGCAACTGCACTGAGCCAACCCTGAA
GACACATGATTATTGGTTGGGCTCCATTAAACAACAAGCCTAGTGCTTGGGAAGGGGG
GTGGGGAGGGGAAGAGACGTGAGAAGCATGTTGGCGTAGACCTTGAGGCATGGATGA
AGCATCTGCCGGCCTGACCTGGTACAGGTGGCATCTGCACTGCAGCAAGGC (SEQ ID NO. 46)

TGACCATCGAAGTGCAAAGGAAATGACTTGATTTCATGAAGTATCTCCAGAAGTAACG
CTTTGTTTTCTGCATCCTGAACTTTATTCCCAGTGAAGAGCTGAAAATCTGGACGCTCA
AAAAATGGAAGCACTTTGGAGAGAGCCCTTAACTCTATCAGGTACAGGAAGTACAAG
TTCCTCAGCCTTCGTGGGCCTTCTCCTTCAGTCAGAATCCATCAAAGGTGCTGGAACTC
TGTGACATTGTGACCCATTCTTTCAGCCAGTATCTGTAAGATAC (SEQ ID NO. 47)

CL-9#1

GGGAACGAATGATCTGGAACTGTGGCTTGTAGACAACCCAAATATCTTAGGTAGGTAA
GAAATTCCAGCATCACACTATATAGGAAATACTGTGCGAAACTGACAGTTAACTGTGC
ACAAAGTTCAATGGCTTCAAAATAATGTATAAAGGATAAGAAGAAACCAGTTTACCAT
TTTGGT ATTATTTTGGTTGCTTTGTATAACTTCAATAATTT        (SEQ ID NO. 48)

CL-54A#2.-SP

GGGAACGAATGATCTGGAACTGTGGCTTGTAGACAACCCAAATATCTTAGGTAGGTAA
GAAATTCCAGCATCACACTATATAGGAAATACTGTGCGAAACTGACAGTTAACTGTGC
ACAAAGTTCAATGGCTTCAAAATAATGTATAAAGGATAAGAAGAAACCAGTTTACCAT
TTTGGTATTATTTTGGTTGCTTTGTATAACTTCAATAATTT        (SEQ ID NO. 49)

CL-54A#2.-SO

GACGTAAGCC        (SEQ ID NO. 50)

CCACAAAGCAAGCTTCTGTCTGGAGTACAGCTCCTGTGACTATGGGTACCACAGGGCC
TTTGCGTGCACTGCACACACAGGGATTGAGTCCTGGATGTTATGACACCTATGCGG
CAGACATAGACTGCCAGTGGATTGATATTACAGATGTACAACCTGGAAACTACATTCT
AAAGGTCAGTGTAAA (SEQ ID NO. 51)

FIG. 12E

CTATCAATGAAGGGGGAGATCACTGGGTAAGTTCGAATGCCCTCAGGCAAGGTGGCC

CAGCCTTCCATTACTGAATTCAAAGATGGCACTGTTACTGTACGTTACTCACCCAGTGA

AGCTGGCCTGCATGAAATGGACATTCGCTATGACAATATGCATATCCCAGGAAGCCCT

CTGCAGTTCTATGTTGATTATGTCAACTGTGGCCACATCACTGCTTATGGTCC (SEQ ID NO. 52)

TTAGCACCTCGACCACGAAATGAGGAAGATGCAACAGACGTGGTGGGCCTGGCTCAG

GCTGTAAACGCTCGGTCCCCACCTTCAGTAAAACAGAACAGCTTGGATGAAGACCTTA

TTCGGAAGCTAGCTTATGTTGCTGCTGGGGACCTGGCACCCATAAATGCTTTCATTGG

GGGCCTTGCTGCCCAGGAAGTCATGAAGGCCTGCTCTGGAAAGTTTATGCCCATCATG

CAGTGGTTGTACTTTGATGCTCTTGAATGTCTCCCAGAACGGACAAAGAGGCTCTGAC

AGAGGAGAGTGCCTCCCACGTCAGAACCGTTACGATGGGCAGGTAGCTGTATTGGTCA

GACTTCAGGAGAAGCTGAGAAGCAAA (SEQ ID NO. 53)

TTAGCACCTCCAATGGCTGGGTACCAGCCAGCCGCAATGTCCGCTCCACAAATTTGGA

GTCTGTGAGGTACTGATTAACATTTTCTGCTGGCTGCTTGAAAAGGCCTTCAAATTCAT

CCCGGGCCCACTGAAGAGTGTGTTCGATGGCATTGGGAAAGTTTTTCAGGGTACAAAT

GGGGATGGATTTCTCTGGTGGATCCTGGCTAGACGTGATGGATTCTGTCAGGAAGGGG

ATTACCACCTGCACGTTGCCCTTT (SEQ ID NO. 54)

TTAGCACCTCACACTCACATGCCCTTCTACATAGAGACTGGTTAAACAGCCCTCCCTCC

CTTGTCCCGACTTGACTTCCAGGCCCCTCTGCTTTCCTCTCACAACCACACCAGGTCTG

ATGGAGTCCAGTGCCTGCAGTGACCCAACATAGACTGCACTTTCACCTACCTACTGGA

TGGTCCTGCAGCCCAGACGGCTGCTCTTCTTTCTCATGGAGTTTCTCTCCTGCCTGAGA

TATGCTATCTGGTCTGCCCCTGTGTAGCTCCCATGGGATCCCTTAAAATCGATCCTTTT

TTAA (SEQ ID NO. 55)

FIG. 12F

TTAGCACCTCGTGAGGAGACTGTTGTCCACAGGCCAGCTAGTGGTACCCTACTGAGAA

GTTGGGTTTTGGTTTTGTTTCCCTTGAAGGGTCGCTGTTAGAGGATGGAAGTAACTTCT

AATTCTTGATCTGTTTGTTGGTCTTGTTTTCAGTACTTTTTGCCAGTTGTATACACTTGG

AGAGGGAATTTGTATGCCTGTAATCTTGTTCTTGAGGTCAGAAATTCAAAACATTGGG

AGCTTTTGTTGTAAAGGTTAAACTGTGAATCCATATAGCAAATGCAGATCCTTTTACA

GTGTAAACCACATTTCCTGCCTCAGCCTAAAGCACTGGTCATTT (SEQ ID NO. 56)

ACCTGCATGCCTAAAGGAGTAGGCTTAGGGGTGGGGAGAGAGAAGGCATAGGCTTTT

CTAGTTATACAAAGCTGTGTAAGGCAAGGTTCCTTTCTACTAAATGGTCAGCTGTCACT

ACATTTATACTTTTGTATGTCATAAACCCTTTCTTTCATTCCTCCCTGGGTAACCAGGA

CAATCGGAGGGCAGTGTGTTACTGGGATTAGAGGACTAGCAATACTGGGTAACCCGCC

TAAGCTGGAAGGTGACGTAATACGTTTCTTTAAAGATTCAGTCAGTCAAGCAGTTTAG

CAATATCAAAATGTCTGGCTGTTTGGTCCAGTGTACACTGTT (SEQ ID NO. 57)

GCTATCTGCGAAACTACAGAAAGGAAGACAGCTTGGCCCAGCGCGGTGAAGTTCAGA

ATTCACTAGGTAGTTGTTGTTGGTTGACTTGGAGGTAGCTGGGTAATCAACAGCTTTCA

CTTTAGATTCAATGTGAACCGCAGAGTTACTCATGACCAAGAGTCTGGCAAACTCATT

AATGCTGTTTAATACTTGTTTGATATTTTTTCACCTTTTGAGCCCTTTTCCCAAAGAATT

CAATATCAGTTTAGTAGCAACAGTACAGTTGCCATTTAAATTGGTTTAGTTGCAGTATA

GCA (SEQ ID NO. 58)

GCTATCTGCGAAACTACAGAAAGGAAGACAGCTTGGCCCAGCGCGGTGAAGTTCAGA

ATTCACTAGGTAGTTGTTGTTGGTTGACTTGGAGGTAGCTGGGTAATCAACAGCTTTCA

CTTTAGATTCAATGTGAACCGCAGAGTTACTCATGACCAAGAGTCTGGCAAACTCATT

AATGCTGTTTAATACTTGTTTGATATTTTTTCACCTTTTGAGCCCTTTTCCCAAAGAATT

FIG. 12G

CAATATCAGTTTAGTAGCAACAGTACAGTTGCCATTTAAATTGGTTTAGTTGCAGTATA
GCA
(SEQ ID NO. 59)

GCTATACTGCAACTAAACCAATTTAAATGGCAACTGTACTGTTGCTACTAAACTGATA
TTGAATTCTTTGGGAAAAGGGCTCAAAAGGTGAAAAAATATCAAACAAGTATTAAAC
AGCATTAATGAGTTTGCCAGACTCTTGGTCATGAGTAACTCTGCGGTTCACATTGAATC
TAAAGTGAAAGCTGTTGATTACCCAGCTACCTCCAAGTCAACCAACAACAACTACCTA
GTGAATTCTGAACTTCACCGCGCTGGGCCAAGCTGTCTTCC
(SEQ ID NO. 60)

GCTATACTGCCCACCACATTGCCACACTCGGAATGACATTTCTATATTTTCACCTCCCC
AGATTTCCATTTCTTCATCGTAACTTCCAATGTGCTCAAAATATTTTTAGATATAGAA
AAAAGGCCTCCTGCAAAGGTGGGGGTCTTAATTGGGTAGGTTTCATCTTTCCTTCTTTG
CTTCTCATGATCAGGAAGTGACTCCCAGCCAAAGGAAAGGCTCCAGTCAAAATTTCCA
CGGTTATGGTTGCTTCCGTACGGAGAAGGCTTGTTGAATTCAAATGTGTTTAGATCTAT
GGATGCGATGTCTGGACTCACCACGGCA
(SEQ ID NO. 61)

GCTATACTGCTGAAGGAGATCATTTTGGTGGATGATGCTAGTGTAGACGACTACCTGC
ATGAAAAGCTGGAGGAATACATAAAACAGTTTTCTATTGTGAAAATAGTCAGGCAGC
AAGAAAGGAAAGGCCTGATCACCGCGCGGTTGCTAGGGGCAGCTGTAGCAACTGCCG
AGACGCTCACGTTCTTAGATGCTCACTGTGAGTGCTTCTATGGCTGGCTGGAACCTCTG
CTGGCCAGGATAGCTGAGAACTACACTGCCG
(SEQ ID NO. 62)

AGTTGCCAGGGGGCAGCTCACGGCGCAGCTCATCCTCTGTGATGTAATTCTTATCTCC
AGCCAGGATCTTGAAGGAAGCCATGACCTGATCTGCAGTATCAGTATCTGCCGTCTCT

FIG. 12H

CGGGACATAAAGTCGATGAAGGCCTGGAACGTCACTACCCCCAAGCGGTTGGGGTCT
ACAATGCTCATGATTCGGGCAAACTCTGCCTCTCCCATGTTGTAACCCATGGAGATAA
GGCAGGCGCGGAAATCGTCTGTGTCCATCATGCCCGTCTTCTTCCGGTCAAAGTGGTT
GAAAGA                                                                   (SEQ ID NO. 63)

AAGCCGTGTCGCTGAACTGGGAGGACACACTGCTCACCCTAGAAGGCTCTGGCTGACC
CTCCGCCCGGTTAAACAGGGACTTTGTGGCCATGTGCTGGCGACACAGGTCCTGGTAC
TCAAAAGTAGTGTCACCATGGGCCCCCTCCGGCCCCAGCGCTGCCAGGCGTCCTTATC
CCGCTGTCTCGAATGATGGCGCATACCAAGGCCACTGAAAGCCACTAGCAGCCCAGCG
ACGCCTGCCAGGGCCACTAGAGTAAGCAGCACTGAGCGCATGGGAGATATGCCAT
                                                                         (SEQ ID NO. 64)

AAGCCGTGTCTGGACGTCCGTGTGTCCGGCTCTTGCTCACGCAGTCATGGCCTCCGGA
ACGCGCAAATCGGAAAGTCGGCTCCTGACTTCACGGCCACAGCGGTGGTGGATGGTGC
CTTCAAGGAAATCAAGCTTTCGGACTACAGAGGGAAGTACGTTGTCCTCTTTTTCTACC
CACTGGACTTCACTTTTGTTTGCCCCACGGAGATCATCGCTTTTAGCGACCATGCTGAG
GACTTCCGAAAGCTAGGCTGCGAGGTGCTGGGAGTGTCTGTGGACTCTCAGTTCACCC
ACCTGGCGTGGATCAATACCCCACGGAAAGAGGGAGGCTT           (SEQ ID NO. 65)

AAGCCGTGTCGGAGGGCACCAAGGCTGTCACCAAGTACACCAGCTCCAAGTGAGTGC
TCAAGACTCAGCTCTTAACCCAAAGGCTCTTTTCAGAGCCACTCAAGACTTCAAAATT
GGAGCTTTAATGCTGACTTAGTGACTACCGGGAAAATAACTGACTTCATCTGCAGGAT
TGTGTACAAACACTTATGGTTTAGTAAATCGAAAAGATAGACATTGCCCATCAGTTCT
GTCTGGTCCACTTAAATATGCTTTTTTCTTAGAAGTTCTAAGAACCCTGTCAATAACCT
ATCTAGGTCCAGTCCTTGAGTTCAAAGGCCAAATACCAATG              (SEQ ID NO. 66)

FIG. 12I

CAACGCTCAGGATGTAAGCTGTTTCCAGCACCTGGTTCAAGCGAATGTAAGAAATAAG
AAGGTGTTGAAAGATGCCGTGAATAACATTACAGCAAAGGGGATCACAGATTACAAG
AAAGGCTTTAGCTTTGCCTTCGAACAGCTACTTAATTATAATGTTTCCAGAGCTAATTG
CAATAAGATTATCATGTTATTCACGGATGGAGGAGAAGAGAGAGCCCAGGAGATATT
TGCCAAATACAATAAAGACAAAAAGTCCGTGTGTTTACATTTTCCGTCGGTCAACAT
AATTATGACAGAGGACCTATTCAGTGGATGGCTTGTGAAATAAAGGTTACTATTATGA
GATTCCTCCATT (SEQ ID NO. 67)

TCAACGCTCATCACACCAAGAATCAACTGGTTCTTCAAGTTTGTCTTATTTTCAGATTG
GCCAGTGACGTTGAAGACTGGTAGAGTTCCAGTAATGACAAGTCCCAGTTCCAGGGCA
TCCAAATACACATTTGTCCATTGAACTTGCTTCGCTTTGTCACCAGCTAAAACCATTGG
TCTTCCCAGAACATCTAGATATTCCTGAGTATTGATTCTTATTGCACCAATGGAGGGAA
TCTCATAATAGTAACCTTTATTTTCACAAGCCATCCACTGAATAGGTCTCTGTCATAAT
TATGTTGACCGACGGAAATGTAA (SEQ ID NO. 68)

TAACGCTCAGGAGAAGAATAGGAATGCAGAGAACTCTGCCACAGCCCCCACGCTCCC
GGGCAGCACCTCAGCCACCACCGCAACCACCACCCCTGCTGTAGATGAAAGCAAGCCT
TGGAACCAGTATCGCTTGCCTAAGACTCTTATACCTGACTCCTACCGGGTGATCTTGAG
ACCCTACCTCACCCCCAACAATCAGGGCCTGTACATCTTCCAAGGCAACAGTACTGTT
CGCTTTACCTGCAACCAGACCACGGATGTCATTATCATCCACAGCAAAAAGCTCAACT
ACACCCTCAAAGGAAACCACAGGGTGG (SEQ ID NO. 69)

CGAGTCAGACGGCTTCAGCATCGAGACCTGTAAGATCATGGTGGACATGCTGGATGAA
GATGGGAGTGGCAAGCTTGGCCTGAAGGAGTTCTACATCCTCTGGACGAAGATTCAGA
ATACCAAAAATCTACCGGGAAATCGATGTGGACAGGTCTGGAACTATGAATTCCTA

FIG. 12J

CGAGATGCGGAAAGCACTGGAAGAAGCAGGTTTCAAGCTGCCCTGTCAACTCCATCA

AGTCATCGTTGCCCGGTTTGCAGACGACGAGCTAATCATCGACTTTGACAATTTTG (SEQ ID NO. 70)

CGAGTCAGACAACCTGTTCAAGTGGGGTGGGGACCATCCACGGAGCAGCCGGCACCG

TATATGAAGACCTGAGGTACAAACTCTCCCTAGAGTTCCCCAGCGGCTACCCTTACAA

CGCACCCACAGTGAAGTTCCTCACACCCTGCTACCACCCCAACGTGGACACCCAGGGC

AACATCTGCCTGGACATCCTCAAGGATAAGTGGTCTGCACTATATGATGTCAGGACTA

TCTTGCTCTCTATCCAGAGCCTGCTAGGAGAACCCAACATCGATAGCCTTTGAACACA

CACGCTGCGGAACTCTGGAAAA (SEQ ID NO. 71)

TATGAGTCCGGAGCGACGGCTACGAGTGTGAACTGTTCCAGCCCCGAGCGACACACCA

GAAGTTATGACTACATGGAAGGAGGGGATATAAGGGTGAGAAGACTGTTCTGTCGCA

CCCAGTGGTACCTGAGGATTGACAAACGAGGCAAAGTGAAAGGGACCCAGGAGATGA

AGAACAGCTACAACATCATGGAAATCAGGACCGTGGCAGTTGGAATTGTGGCAATCA

AAGGGGTGGAAAGTGAATACTATCTTGCCATGAACAAGGAAGGGAAACTCTATGCAA

AGAAAGAATGCAATGAGGATTGCAACTTCAAAGAACTGATTCTGGAAAACCATTATA

ACACCTATG (SEQ ID NO. 72)

TATGAGTCCGAGGAGGAGCACAATGCTGGGAGTGTGGAAAGCCAGGTTGTCCCCAGC

ACACACCGAGTGACCGATTCCAAGTTCCATCCACTCCATGCCAAGATGGATGTCATCA

AAAAAGGCCACGCCAGGGACAGCCAGCGCTACAAAGTTGACTATGAGTCTCAAAGCA

CAGACACCCAGAACTTCTCCTCCGAGTCTAAGCGGGAGACAGAATACGGTCCCTGCCG

CAGAGAAATGGAGGACACACTGAATCATCTGAAGTTCCTCAATGTGCTGAGTCCAGAG

TCTCACATCCAAACTGTGACAAGAAGGGG (SEQ ID NO. 73)

FIG. 12K

TCGCCCGGGACTTCATGCGATTGAGAAGATTGTCTACCAAATATAGAACAGAAAAGAT
TTATCCCACAGCCACTGGAGAAAAAGAAGAAAATGTTAAAAAGAACAGATATAAGGA
CATACTGCCATTTGATCACAGCCGAGTTAAGTTGACTTTGAAGACTCCATCCCAAGAT
TCAGATTATATCAATGCAAATTTTATTAAGGGTGTGTATGGGCCAAAAGCATATGTGG
CAACCCAAGGGCCTTT (SEQ ID NO. 74)

TGTGGAAAGCCAGGTTGTCCCCAGCACACACCGAGTGACCGATTCCAAGTTCCATCCA
CTCCATGCCAAGATGGATGTCATCAAAAAGGCCACGCCAGGGACAGCCAGCGCTAC
AAAGTTGACTATGAGTCTCAAAGCACAGACACCCAGAACTTCTCCTCCGAGTCTAAGC
GGGAGACAGAATACGGTCCCTGCCGCAGAGAAATGGAGGACACACTGAATCATCTGA
AGTTCCTCAATGTGCTGAGTCCAGAG (SEQ ID NO. 75)

TGACCATCGAAGTGCAAAGGAAATGACTTGATTTCATGAAGTATCTCCAGAAGTAACG
CTTTGTTTTCTGCATCCTGAACTTTATTCCCAGTGAAGAGCTGAAAATCTGGACGCTCA
AAAAATGGAAGCACTTTGGAGAGAGCCCTTAACTCTATCAGGTACAGGAAGTACAAG
TTCCTCAGCCTTCGTGGGCCTTCTCCTTCAGTCAGAATCCCATCAAAGCGCTGCTGGAA
CTCTGTGACATTGTGACCCCATTTCTTTTCCAGCCAAGTATCTTGTAAAAGATACCTTG
CACTCAAATGCACATTAATGCTTGCGTGCAGGCCAGATATAAGTCTGTAGAATCGCTC
TTTCTACACAGAGGCCTTCTAGCCAGTTGTAAA (SEQ ID NO. 76)

CTGCTTGATGCTAAGCCCGGCAGCCTGTGTTTCATCTACAGGATGCACAACATAAAAG
AAAAGATCTGATTCCCGCAGGTTCTCTTCTGACCTACACACACACACTAAAATAAC
ATTTAAAAATATGTGCCAAATTATATTTGTTCGGGTGCCACCTTCCACCAGCTTACCAC
TACGGTAGAACTGTCAAATTCATCTCCCTGAATTTGTCTTAAAGGGGTGTCCATGCAC
AGGCCCAAGAGTCACCTCCAATGAAATAAATGTAATACTGAAGTATGCCATGATGTTT

FIG. 12L

GTTGTTTTCTTTCATCGTAAGCCTGTAAGCAGGAAAAATAGTAATAGATAGAATAGAG
ACTTACCAGTGGTCGATGGCCTGGTCAGTCTGTGCGGTGACTAGGACCAGG (SEQ ID NO. 77)

ACCTGCATGCCGAGTGTGACGCCTTTGAGGAGAAGATCCAGGCTGCCGGAGGGATCG
AACTCTTTGTCGGAGGCATTGGCCCCGATGGACACATTGCCTTCAATGAGCCAGGCTC
CAGCCTGGTGTCCAGGACCCGTGTGAAGACTCTGGTTATGGACACCATCCTGGCCAAC
GCTAGGTTCTTTGATGGTGATCTTGCCAAGGTGCCCACCATGGCCCTGACAGTGGGTG
TCGGCACTGTCATGGATGCTAAAGAGGTGATGATCCTCATCACAGGCGCTCACAAGGC
CTTTGCTCTGTACAAAGCCATCGATGGAGGCGTGAACCACATGTGGACGGTGTG (SEQ ID NO. 78)

GCTATACTGCAATGTTAGGGGAATGAACGCGTTTCCTACTGCACTGGGGACTTTTAG
ATAGGTTAATGAAAGGCCTTTTATTCTGTTACTGGACACGAAAACTTTGTCTAATTTCT
TATACTCTATTGTACGTTTACAGTCGCAGCACTAAAATGGAAGACATCAAACATTTTT
AACAGAAAAAAAAAAGATGTAAAAACTAACTAAGGACTATTTATTGATAATGTTTTG
CTACTCCTGTCAGACAATGGCTATAAACTGAATTAGGCAGTCTTAAAAAAAAAAAAG
AAAAAAAAGAAAAAAGAAAAAAAGAAAAGAAAAGAAAAAAAACTGG (SEQ ID NO. 79)

AGCTAAGGTCGGGTACTCTGATACTTCAGAGTTTAAAATCATCAGCCCTTGTAGATCT
ATTCCTAAATCTTATGAAAATGCTCAGATGTTTACACAGCTGTGAAACAGGGTCAGTT
CAGATCGCTGATGGCTTGAGAATGTGTTTCTTGTTGACATCAGGAACTGGAAATGTTT
ACTTCCCGTCATTTATGAGTCATCAAGTATCTCGGCTCTTTTAAGAGCGCAAGATAAA
ACAAGCTTAAACCAGGTGATAAGAGCAGAGTCCACTTGAGTCTGAGCTCACCCGAGA
ACTTGCTATCGAGGACATTTGGAATGGGAGTGTGCAGGCTTCCTTCAGTTACTGAATG
AGTCCATCTGCTAGTCACCTTGAC (SEQ ID NO. 80)

FIG. 12M

AGCTAAGGTCCAGGGGGCAAAGCGGTGACGTGTGCACATCGATATGAGAAACGGCAG
CACGTCAACACGAAGCAGGAGTCGCGGGATATCTTTGGAAGATGTTATGTCCTAAGTC
AGAATCTCAGAATTGAAGATGATATGGACGGAGGAGACTGGAGTTTCTGCGATGGCC
GGTTGAGAGGCCATGAAAAGTTTGGCTCCTGTCAGCAAGGAGTAGCGGCTACTTTCAC
TAAGGACTTTCATTACATTGTTTTTGGAGCCCCAGGGACTTACAACTGGAAAGGGATC
GTCGTGTAGAACAAAAGAATAACACTTTTTT (SEQ ID NO. 81)

AAGCCGTGTCTGTGCTCAAGGAAGAAACCCACTGGACCAACTTCTGTCAGAAAGGAA
AACCTTGTTCAAAGTTTCAGGACCCTGTTCTTTGCTTATTTGCACATGGTCACCTTGGT
CTGAGCTAGCCACCATTGTCACCCACAGCTGCAAAGAAAGCAGACCTTAGGAAACACT
GTCACGGCTGAGTGTGACTGCCTTGTTCATCCCCTGGACTGGTACTGTGTTGCCTGCAG
TACCATTGGGATCCCATAGCAAGAGAGGGAGAGGGAGATGTTAGTTAGCCTTTGCTAC
GAACCAAGCTGTCCCAAGTCTCAACAGCTAAACAGGTATTCATTTACCATGATTCTAT
GGTTAGCTAAGCTCTTGAG (SEQ ID NO. 82)

CTTTCTACCCTGGAGGATGTGCTTGAGGCACACTGCTCCTGTGCTCTCCACTTGAGGCA
TAAGCCCAGTCAGTTGTGCATAGATGATTAACCTCTGACCCCTAAAGATGGTAAGTTG
CTCTGGAGAAAGCATTTTAACAGACAAACCAGGAGGCAAATCCCAACTTAGAGAGAT
GTTATCCACTGCACACTGTAGAGCAAACTTGAGAGACCCAAGAGCCTTGGTCTGCATC
CTGTCCTTGCCTGTGATAAACACTCGAGTACCCCTGATACCGGGCGATATTTTTGATT
AACTGGTCGAGGCTCCTTGTCCAATTCCAAAAGAGAACATCTGTGTTTC (SEQ ID NO. 83)

FIG. 12N

TGGTAAAGGGCATCTGTAAATACACTCTATGAGGAAATTAAAACTTGAACATGGCAGT
CTGACATTGCAAAACAAAACAAAACAAAACTGACCCTCCAATAGCAGCGAAAACAAC
GTGAAAGATACAAAGCAATGAGAATCTGGTTCTGAACGCCTGGGATCCTGGGAGTCAT
CGGTAGCAGCGCCATGAGAGGAGCCGTGGCCTGTCCCATGTGGTCCCACCTTCACCTC
TTCCCTCACATCCCTCTTAAG (SEQ ID NO. 84)

TGGTAAAGGGGGCAAGGGCAAAGGCACGGGAGACAGAGGCCACTGCATCTGTACCCA
CATCAGACATGTTTGTCCATTTTCTCTCATTTGGCCTTAGACCATTGGCAAGAGTAAAT
GCTCTTAGTCCCGTTATCTAGAAATTTCTTCCTTTGGGGAGAACCACTTATAGACAATA
TCAGCTCTCTACAAATAACACGAAAGGTCGTAACAC
AGCAAGTGACCAGAAAGTGCCCGTCCTTGCGGCTCTGATCCACGTGGCTCTCCGTAGA
CAAATTGTTTTTTCTTGTAGGGATATCTGTTTTGCTTCTGAACTTTCTTACAAGTGTTTG
GGACTCTTCGGGTGGCGTT (SEQ ID NO. 85)

TGGTAAAGGGTCAAGTGTTCGATCAGAGTGGAGCTCCATTACCGAATGTAATCGTGGA
AGTCCAAGACAGAAAGCATATCTGCCCGTTTAGAACCAACAAGCTTGGAGAATACTAT
CTGCTTCTGCTGCCCGGGTCCTACGTGATCAATGTTACAGTCCCTGGACACGACTCCTA
CCTCACGAAGCTTACTATTCCAGGGAAATCCCAGCCCTTCAGTGCTCTTAAAAAGGAT
TTTCACCTCCCGCTGCGATGGCAGCCGGATTCCATCTCCGTATCCAATCCTTCGTGCCG
ATGATTCCGCTGTACAAATTCATGCCAAGCCACTCGGCTGCCACAAAGCCTAGTCTGG
G (SEQ ID NO. 86)

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT

FIG. 120

GGTTTGTCTTGATCAAGAACAAAGAATTCATTCCCACCATTCTCATATATACTACTTTC
TCTTCTT (SEQ ID NO. 87)

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT
GGTTTGTCTTGATCAAGAACAAAGAATTCATTCCACCATTCTCATATATCTACGTCTCT
TCTAG (SEQ ID NO. 88)

ACGAGGGGAAACCTCCTCAGAGCCTGCAGCCAGCCACGCGCCAGCATGTCTGGGGGC
AAATACGTAGACTCCGAGGGACATCTCTACACTGTTCCCATCCGGGAACAGGGCAACA
TCTACAAGCCCAACAACAAGGCCATGGCAGACGAGGTGACTGAGAAGCAAGTGTATG
ACGCGCACACCAAGGAGATTGACCTGGTCAACCGCGACCCCAAGCATCTCAACGACG
ACGTGGTCAAGATTGACTTTGAAGATGTGATTGCAGAACCAGAAGGGACACACAGTTT
CGACGGCATCTGGAAGGCCAGCTTCACCACCTTCACTGTGACAAAATATTGGTTTTAC
CGCTTGTTGTCTACGATCTTCGGCATCCCAATGGCACTCATCTGGGGCATTTACTTTGC
CATTCTCTCCTTCCTGCACATCTGGGCGGTTGTACCGTGCATCAAGAGCTTCCTGATTG
AGATTCAGTGCATCAGCCGCGTCTACTCCATCTACGTCCATACCTTCTGCGATCCACTC
TTTGAAGCTATTGGCAAGATATTCAGCAACATCCGCATCAGCACGCAGAAAGAGATAT
GAGGGACATTTCAAGGATGAAAGGTTTTTTTCCCCCCTTACTATTTCCTTGGTGCCAAT
TCCAAGTTGCTCTCGCAGCAGCAAATTTATGAATGGTTTGTCTTGATC (SEQ ID NO. 89)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIF
PRCQKEDANGNIVYEKNCRNEAGLSADPYVYNWTAWSEDSDGENGTGQSHHNVFPDGK

FIG. 12P

PFPHHPGWRRWNFIYVFHTLGQYFQKLGRCSVRVSVNTANVTLGPQLMEVTVYRRHGRA
YVPIAQVKDVYVVTDQIPVFVTMFQKNDRNSSDETFLKDLPIMFDVLIHDPSHFLNYSTIN
YKWSFGDNTGLFVSTNHTVNHTYVLNGTFSLNLTVKAAAPGPCPPPPPPRPSKPTPSLGP
AGDNPLELSRIPDENCQINRYGHFQATITIVEGILEVNIIQMTDVLMPVPWPESSLIDFVVTC
QGSIPTEVCTIISDPTCEITQNTVCSPVDVDEMCLLTVRRTFNGSGTYCVNLTLGDDTSLAL
TSTLISVPDRDPASPLRMANSALISVGCLAIFVTVISLLVYKKHKEYNPIENSPGNVVRSKGL
SVFLNRAKAVFFPGNQEKDPLLKNQEFKGVS (SEQ ID NO. 90)

```
1   CAGATGCCAG AAGAACACTG TTGCTCTTGG TGGACGGGCC CAGAGGAATT
    CAGAGTTAAA
61  CCTTGAGTGC CTGCGTCCGT GAGAATTCAG CATGGAATGT CTCTACTATT
    TCCTGGGATT
121 TCTGCTCCTG GCTGCAAGAT GCCACTTGA TGCCGCCAAA CGATTTCATG
    ATGTGCTGGG
181 CAATGAAAGA CCTTCTGCTT ACATGAGGGA GCACAATCAA TTAAATGGCT
    GGTCTTCTGA
241 TGAAAATGAC TGGAATGAAA AACTCTACCC AGTGTGGAAG CGGGGAGACA
    TGAGGTGGAA
301 AAACTCCTGG AAGGGAGGCC GTGTGCAGGC GGTCCTGACC AGTGACTCAC
    CAGCCCTCGT
361 GGGCTCAAAT ATAACATTTG CGGTGAACCT GATATTCCCT AGATGCCAAA
    AGGAAGATGC
421 CAATGGCAAC ATAGTCTATG AGAAGAACTG CAGAAATGAG GCTGGTTTAT
    CTGCTGATCC
481 ATATGTTTAC AACTGGACAG CATGGTCAGA GGACAGTGAC GGGGAAAATG
    GCACCGGCCA
541 AAGCCATCAT AACGTCTTCC CTGATGGGAA ACCTTTTCCT CACCACCCCG
    GATGGAGAAG
```

FIG. 12Q

```
 601 ATGGAATTTC ATCTACGTCT TCCACACACT TGGTCAGTAT TTCCAGAAAT
TGGGACGATG
 661 TTCAGTGAGA GTTTCTGTGA ACACAGCCAA TGTGACACTT GGGCCTCAAC
TCATGGAAGT
 721 GACTGTCTAC AGAAGACATG GACGGGCATA TGTTCCCATC GCACAAGTGA
AAGATGTGTA
 781 CGTGGTAACA GATCAGATTC CTGTGTTTGT GACTATGTTC CAGAAGAACG
ATCGAAATTC
 841 ATCCGACGAA ACCTTCCTCA AAGATCTCCC CATTATGTTT GATGTCCTGA
TTCATGATCC
 901 TAGCCACTTC CTCAATTATT CTACCATTAA CTACAAGTGG AGCTTCGGGG
ATAATACTGG
 961 CCTGTTTGTT TCCACCAATC ATACTGTGAA TCACACGTAT GTGCTCAATG
GAACCTTCAG
1021 CCTTAACCTC ACTGTGAAAG CTGCAGCACC AGGACCTTGT CCGCCACCGC
CACCACCACC
1081 CAGACCTTCA AAACCCACCC CTTCTTTAGG ACCTGCTGGT GACAACCCCC
TGGAGCTGAG
1141 TAGGATTCCT GATGAAAACT GCCAGATTAA CAGATATGGC CACTTTCAAG
CCACCATCAC
1201 AATTGTAGAG GGAATCTTAG AGGTTAACAT CATCCAGATG ACAGACGTCC
TGATGCCGGT
1261 GCCATGGCCT GAAAGCTCCC TAATAGACTT TGTCGTGACC TGCCAAGGGA
GCATTCCCAC
1321 GGAGGTCTGT ACCATCATTT CTGACCCCAC CTGCGAGATC ACCCAGAACA
CAGTCTGCAG
1381 CCCTGTGGAT GTGGATGAGA TGTGTCTGCT GACTGTGAGA CGAACCTTCA
ATGGGTCTGG
1441 GACGTACTGT GTGAACCTCA CCCTGGGGGA TGACACAAGC CTGGCTCTCA
CGAGCACCCT
```

FIG. 12R

1501 GATTTCTGTT CCTGACAGAG ACCCAGCCTC GCCTTTAAGG ATGGCAAACA GTGCCCTGAT

1561 CTCCGTTGGC TGCTTGGCCA TATTTGTCAC TGTGATCTCC CTCTTGGTGT ACAAAAAACA

1621 CAAGGAATAC AACCCAATAG AAAATAGTCC TGGGAATGTG GTCAGAAGCA AAGGCCTGAG

1681 TGTCTTTCTC AACCGTGCAA AAGCCGTGTT CTTCCCGGGA AACCAGGAAA AGGATCCGCT

1741 ACTCAAAAAC CAAGAATTTA AAGGAGTTTC TTAAATTTCG ACCTTGTTTC TGAAGCTCAC

1801 TTTTCAGTGC CATTGATGTG AGATGTGCTG GAGTGGCTAT TAACCTTTTT TTCCTAAAGA

1861 TTATTGTTAA ATAGATATTG TGGTTTGGGG AAGTTGAATT TTTTATAGGT TAAATGTCAT

1921 TTTAGAGATG GGGAGAGGGA TTATACTGCA GGCAGCTTCA GCCATGTTGT GAAACTGATA

1981 AAAGCAACTT AGCAAGGCTT CTTTTCATTA TTTTTTATGT TTCACTTATA AAGTCTTAGG

2041 TAACTAGTAG GATAGAAACA CTGTGTCCCG AGAGTAAGGA GAGAAGCTAC TATTGATTAG

2101 AGCCTAACCC AGGTTAACTG CAAGAAGAGG CGGGATACTT TCAGCTTTCC ATGTAACTGT

2161 ATGCATAAAG CCAATGTAGT CCAGTTTCTA AGATCATGTT CCAAGCTAAC TGAATCCCAC

2221 TTCAATACAC ACTCATGAAC TCCTGATGGA ACAATAACAG GCCCAAGCCT GTGGTATGAT

2281 GTGCACACTT GCTAGACTCA GAAAAAATAC TACTCTCATA AATGGGTGGG AGTATTTTGG

2341 TGACAACCTA CTTTGCTTGG CTGAGTGAAG GAATGATATT CATATATTCA TTTATTCCAT

FIG. 12S

2401 GGACATTTAG TTAGTGCTTT TTATATACCA GGCATGATGC TGAGTGACAC
TCTTGTGTAT
2461 ATTTCCAAAT TTTTGTATAG TCGCTGCACA TATTTGAAAT CATATATTAA
GACTTTCCAA
2521 AGATGAGGTC CCTGGTTTTT CATGGCAACT TGATCAGTAA GGATTTCACC
TCTGTTTGTA
2581 ACTAAAACCA TCTACTATAT GTTAGACATG ACATTCTTTT TCTCTCCTTC
CTGAAAAATA
2641 AAGTGTGGGA AGAGACAAAA AAAAAAAAA //

(SEQ ID NO. 91)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 92)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTA (SEQ ID NO. 93)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT

FIG. 12T

CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 94)

TACGAAGGTGGAGGCGGAGTCGAAGGCGAAGGGGGAGGGCATGGCCCGGGCACTGCA
GTTTGCACGGTGAGGTTAAGGTTGAAGGTTCCATTGAGCACATAAGTGTGATTCAAAG
TGTGATTGTTGGAGACAAACAGGCCAGTGTTGTCCCCAAAGTTCCACTTGTAGGAAAT
GGCAGAGTCGTTGAGGA (SEQ ID NO. 95)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 96)

RRWRRSRRRRGRAWPGHCSLHGEVKVEGSIEHISVIQSVIVGDKQASVVPKVPLVGNGRV
VEEVAGIMNEDIEDDGEVSEEDLIRQVPVILLGHGHEYRDLICYHIHIFHL (SEQ ID NO. 97)

KVKDVYVITDQIPVFVTMSQKNDRNLSDEIFLRDLPIVFDVLIHDPSHFLNDSAISYKWNFG
DNTGLFVSNNHTLNHTYVLNGTFNLNLTVQTAVPGPCPPPSPSTPPPPS (SEQ ID NO. 98)

FIG. 12U

YEGGGGVEGEGGGHGPGTAVCTVRLRLKVPLST*V*FKV*LLETNRPVLSPKFHL*EMAES
LRKWLGS*MRTSKTMGRSLRKISSDKFLSFFWDMVTNTGI*SVITYTSFT (SEQ ID NO. 99)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIFPRCQKEDANGNIVYE
KNCRNEAGLSADPYVYNWTAWSEDSDGENGTGQSHHNVFPDGK
PFPHHPGWRRWNFIYVFHTLGQYFQKLGRCSVRVSVNTANVTLGPQLMEVTVYRRHGRA
YVPIAQVKDVYVVTDQIPVFVTMFQKNDRNSSDETFLKDLPIMFDVLIHDPSHFLNYSTIN
YKWSFGDNTGLFVSTNHTVNHTYVLNGTFSLNLTVKAAAPGPCPPPPPPRPSKPTPSLGP
AGDNPLELSRIPDENCQINRYGHFQATITIVEGILEVNIIQMTDVLMPVPWPESSLIDFVVTC
QGSIPTEVCTIISDPTCEITQNTVCSPVDVDEMCLLTVRRTFNGSGTYCVNLTLGDDTSLAL
TSTLISVPDRDPASPLRMANSALISVGCLAIFVTVISLLVYKKHKEYNPIENSPGNVVRSKGL
SVFLNRAKAVFFPGNQEKDPLLKNQEFKGVS        (SEQ ID NO. 100)

1    CAGATGCCAG  AAGAACACTG  TTGCTCTTGG  TGGACGGGCC  CAGAGGAATT
     CAGAGTTAAA
61   CCTTGAGTGC  CTGCGTCCGT  GAGAATTCAG  CATGGAATGT  CTCTACTATT
     TCCTGGGATT
121  TCTGCTCCTG  GCTGCAAGAT  TGCCACTTGA  TGCCGCCAAA  CGATTTCATG
     ATGTGCTGGG
181  CAATGAAAGA  CCTTCTGCTT  ACATGAGGGA  GCACAATCAA  TTAAATGGCT
     GGTCTTCTGA
241  TGAAAATGAC  TGGAATGAAA  AACTCTACCC  AGTGTGGAAG  CGGGGAGACA
     TGAGGTGGAA
301  AAACTCCTGG  AAGGGAGGCC  GTGTGCAGGC  GGTCCTGACC  AGTGACTCAC
     CAGCCCTCGT
361  GGGCTCAAAT  ATAACATTTG  CGGTGAACCT  GATATTCCCT  AGATGCCAAA
     AGGAAGATGC

FIG. 12V

```
421 CAATGGCAAC ATAGTCTATG AGAAGAACTG CAGAAATGAG GCTGGTTTAT
CTGCTGATCC
481 ATATGTTTAC AACTGGACAG CATGGTCAGA GGACAGTGAC GGGGAAAATG
GCACCGGCCA
541 AAGCCATCAT AACGTCTTCC CTGATGGGAA ACCTTTTCCT TACCACCCCG
GATGGAGAAG
601 ATGGAATTTC ATCTACGTCT TCCACACACT TGGTCAGTAT TTCCAGAAAT
TGGGACGATG
661 TTCAGTGAGA GTTTCTGTGA ACACAGCCAA TGTGACACTT GGCCTCAAC
TCATGGAAGT
721 GACTGTCTAC AGAAGACATG GACGGGCATA TGTTCCCATC GCACAAGTGA
AAGATGTGTA
781 CGTGGTAACA GATCAGATTC CTGTGTTTGT GACTATGTTC CAGAAGAACG
ATCGAAATTC
841 ATCCGACGAA ACCTTCCTCA AAGATCTCCC CATTATGTTT GATGTCCTGA
TTCATGATCC
901 TAGCCACTTC CTCAATTATT CTACCATTAA CTACAAGTGG AGCTTCGGGG
ATAATACTGG
961 CCTGTTTGTT TCCACCAATC ATACTGTGAA TCACACGTAT GTGCTCAATG
GAACCTTCAG
1021 CCTTAACCTC ACTGTGAAAG CTGCAGCACC AGGACCTTGT CCGCCACCGC
CACCACCACC
1081 CAGACCTTCA AAACCCACCC CTTCTTTAGG ACCTGCTGGT GACAACCCCC
TGGAGCTGAG
1141 TAGGATTCCT GATGAAAACT GCCAGATTAA CAGATATGGC CACTTTCAAG
CCACCATCAC
1201 AATTGTAGAG GGAATCTTAG AGGTTAACAT CATCCAGATG ACAGACGTCC
TGATGCCGGT
1261 GCCATGGCCT GAAAGCTCCC TAATAGACTT TGTCGTGACC TGCCAAGGGA
GCATTCCCAC
```

FIG. 12W

```
1321 GGAGGTCTGT ACCATCATTT CTGACCCCAC CTGCGAGATC ACCCAGAACA
CAGTCTGCAG
1381 CCCTGTGGAT GTGGATGAGA TGTGTCTGCT GACTGTGAGA CGAACCTTCA
ATGGGTCTGG
1441 GACGTACTGT GTGAACCTCA CCCTGGGGGA TGACACAAGC CTGGCTCTCA
CGAGCACCCT
1501 GATTTCTGTT CCTGACAGAG ACCCAGCCTC GCCTTTAAGG ATGGCAAACA
GTGCCCTGAT
1561 CTCCGTTGGC TGCTTGGCCA TATTTGTCAC TGTGATCTCC CTCTTGGTGT
ACAAAAAACA
1621 CAAGGAATAC AACCCAATAG AAAATAGCCC TGGGAATGTG GTCAGAAGCA
AAGGCCTGAG
1681 TGTCTTTCTC AACCGTGCAA AAGCCGTCTT CTTCCCGGGA AACCAGGAAA
AGGATCCGCT
1741 ACTCAAAAAC CAAGAATTTA AAGGAGTTTC TTAAATTTCG ACCTTGTTTC
TGAAGCTCAC
1801 TTTTCAGTGC CATTGATGTG AGATGTGCTG GAGTGGCTAT TAACCTTTTT
TTCCTAAAGA
1861 TTATTGTTAA ATAGATATTG TGGTTTGGGG AAGTTGAATT TTTTATAGGT
TAAATGTCAT
1921 TTTAGAGATG GGGAGAGGGA TTATACTGCA GGCAGCTTCA GCCATGTTGT
GAAACTGATA
1981 AAAGCAACTT AGCAAGGCTT CTTTTCATTA TTTTTTATGT TTCACTTATA
AAGTCTTAGG
2041 TAACTAGTAG GATAGAAACA CTGTGTCCCG AGAGTAAGGA GAGAAGCTAC
TATTGATTAG
2101 AGCCTAACCC AGGTTAACTG CAAGAAGAGG CGGGATACTT TCAGCTTTCC
ATGTAACTGT
2161 ATGCATAAAG CCAATGTAGT CCAGTTTCTA AGATCATGTT CCAAGCTAAC
TGAATCCCAC
```

FIG. 12X

2221 TTCAATACAC ACTCATGAAC TCCTGATGGA ACAATAACAG GCCCAAGCCT GTGGTATGAT

2281 GTGCACACTT GCTAGACTCA GAAAAAATAC TACTCTCATA AATGGGTGGG AGTATTTTGG

2341 TGACAACCTA CTTTGCTTGG CTGAGTGAAG GAATGATATT CATATATTCA TTTATTCCAT

2401 GGACATTTAG TTAGTGCTTT TTATATACCA GGCATGATGC TGAGTGACAC TCTTGTGTAT

2461 ATTTCCAAAT TTTTGTATAG TCGCTGCACA TATTGAAAT CATATATTAA GACTTTCCAA

2521 AGATGAGGTC CCTGGTTTTT CATGGCAACT TGATCAGTAA GGATTTCACC TCTGTTTGTA

2581 ACTAAAACCA TCTACTATAT GTTAGACATG ACATTCTTTT TCTCTCCTTC CTGAAAAATA

2641 AAGTGTGGGA AGAGACAAAA AAAAAAAAA //        (SEQ ID NO. 101)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIFPRCQKEDANGNIVYE
KNCRNEAGLSADPYVYNWTAWSEDSDGENGTGQSHHNVFPDGKPFPHHPGWRRWNFIY
VFHTLGQYFQKLGRCSVRVSVNTANVTLGPQLMEVTVYRRHGRAYVPIAQVKDVYVVT
DQIPVFVTMFQKNDRNSSDETFLKDLPIMFDVLIHDPSHFLNYSTINYKWSFGDNTGLFVS
TNHTVNHTYVLNGTFSLNLTVKAAAPGPCPPPPPPPRPSKPTPSLGPAGDNPLELSRIPDEN
CQINRYGHFQATITIVEGILEVNIIQMTDVLMPVPWPESSLIDFVVTCQGSIPTEVCTIISDPT
CEITQNTVCSPVDVDEMCLLTVRRTFNGSGTYCVNLTLGDDTSLALTSTLISVPDRDPASP
LRMANSALISVGCLAIFVTVISLLVYKKHKEYNPIENSPGNVVRSKGLSVFLNRAKAVFFPG
NQEKDPLLKNQEFKGVS* (SEQ ID NO. 102)

FIG. 12Y

CTGACCAGGAACCCACTCTTCTGTGCATGTATGTGAGCTGTGCAGAAGTATGTGGCTG
GGAACTGTTGTTCTCTAAGGATTATTGTAAAATGTATATCGTGGCTTAGGGAGTGTGG
TTAAATAGCATTTTAGAGAAGAAAAAAAAAAAAAAAAAAACTCGAGAGTACTTCTAG
AGCGGCCGCGGCGCCATCGATTTTCCACCCGGGTGGGGTACCAGGTAAGTGTACCCAA
TTCGCCTATAGTGAGT                                  (SEQ ID NO. 103)

AGGACAAGCCAAGGACACTCTAAGTCTTTGGCCTTCCCTCTGACCAGGAACCCACTCT
TCTGTGCATGTATGTGAGCTGTGCAGAAGTATGTGGCTGGGAACTGTTGTTCTCTAAG
GATTATTGTAAAATGTATATCGTGGCTTAGGGAGTGTGGTTAAATAGCATTTTAGAGA
AGACATGGGAAGACTTAGTGTTTCTTCCCATCTGTATTGTGGTTTTTACACTGTTCGTG
GGGTGGACACGCTGTGTCTGAAGGGGAGGTGGGGGTCACTGCTACTTAAGGTCCTAGG
TTAACTGGGGGAGATACCACAGATGCTCAGCTTTCCACATAACATGGGCATGAACCAG
CTAATCACACTGAA                                    (SEQ ID NO. 104)

GGATCCTTCTCCTGGTCTCCTCGGAAGAACGGGGCTTTCGCGTGACTGAGGAGAACAC
TCAGGCCCTTGCCCTTGACCGTGTTCCTGGGGCAGTTTCCTATTGGCTTGTACGCCTTG
TGTTTTTTGTACAGCAAGATGGTAACCATGGTGACAAGCACAGCCAGGCAGCCGATGG
AGATCAGGACACCATTCACTGCTCTCAGAGGGAGTCTGGGTCTTTGCCAGGGATAGAG
ATCAGGGTGCTGGTGAGGGCCAGGCTTCGATCATCTCCCAGAGTGAAATTCACACAGT
AGGTGCCAGACCCATTGAAGGCTCTTCTCACAGACAGCAGCACAGCCCATCCACAGCC
ACAGGGCTGCAGACCCGGTTCTGGGCGATCTGGCAGGTGGGGTCGGAGATGATCGTA
CAGGCTTCCATGGGGGTGGCCCCTTTGCAGGTCACAGTGAAGTCCATCAGGGAGTTGG
CAGGCTGCGGTGTGGGCATGGGGACATCTGCTATCTGCATGATGCTGACTTCCAGGATCC
                                                   (SEQ ID NO. 105)

TAGCAGATGTCCCCATGCCCACACCGCAGCCTGCCAACTCCCTGATGGACTTCACTGT
GACCTGCAAAGGGGCCACCCCCATGGAAGCCTGTACGATCATCTCCGACCCCACCTGC
CAGATCGCCCAGAACCGGGTCTGCAGCCCTGTGGCTGTGGATGGGCTGTGCTGCTGTC

FIG. 12Z

TGTGAGAAGAGCCTTCAATGGGTCTGGCACCTACTGTGTGAATTTCACTCTGGGAGAT

GATCGAAGCCTGGCCCTCACCAGCACCCTGATCTCTATCCCTGGCAAAGACCCAGACT

CCCTCTGAGAGCAGTGAAT (SEQ ID NO. 106)

GGATCCTTCTCCTGGTCTCCTCGGAAGAACGGGGCTTTCGCGTGACTGAGGAGAACAC

TCAGGCCCTTGCCCTTGACCGTGTTCCTGGGGCAGTTTCCTATTGGCTTGTACGCCTTG

TGTTTTTTGTACAGCAAGATGGTAACCATGGTGACAAGCACAGCCAGGCAGCCGATGG

AGATCAGGACACCATTCACTGCTCTCAGAGGGAGTCTGGGTCTTTGCCAGGGATAGAG

ATCAGGGTGCTGGTGAGGGCCAGGCTTCGATCATCTCCCAGAGTGAAATTCACACAGTA (SEQ ID NO. 107)

TTTTTTTTTTTTTTTTAGACTGCCTTTTAATGAGTAGAATATGTACACACGCACC

ATACACAAAGCCCGGGCCCATTATAATTTTGTCAGGAGCTCAGGCATGCTCAGTGAGT

TGGAAGGCAGATGAAGCATG

CCTTCAGGTGGTGATTAGCTGGGTTCATGCCCATGTTATCGTGGAAAGCTGAGGCATC

TGTGGTATCTCCCCCAGTTAACCTAGGACCTTAAGTAGCAGTGACCCACCTCCCTTCAG

ACACAGCG (SEQ ID NO. 108)

GGATCCTGGAAGTCAGCATCATGCAGATAGCAGATGTCCCCATGCCCACACCGCAGCC

TGCCAACTCCCTGATGGACTTCACTGTGACCTGCAAAGGGGCCACCCCCATGGAAGCC

TGTACGATCATCTCCGACCCCACCTGCCAGATCGCCCAGAACCGGGTCTGCAGCCCTG

TGGCTGTGGATGGGCTGTGCTGCTGTCTGTGAGAAGAGCCTTCAATGGGTCTGGCACC

TACTGTGTGAATTTCACTCTGGGAGATGATCGAAGCCT (SEQ ID NO. 109)

FIG. 12AA

TTTTTTTTTTTTTTTTTTTCTTCTCTAAAATGCTATTTAACCACACTCCCTAAGCCACGA
TATACATTTTACAATAATCCTTAGAGAACAACAGTTCCCAGCCACATACTTCTGCACA
GCTCACATACATGCACAGAAGAGTGGGTTCCTGGTCAGAGGGAAGGCCAAAGACTTA
GAGTGTCCTTGGCTTGTCTGGAGCAATGGATCCTTCTCCTGGTCTCCTCGGAAGAACG
GCTTT                                                                  (SEQ ID NO. 110)

AAACTGCAGTGCCCGGGCCATGCCCTCCCCCTTCGCCTTCGACTCCGCCTCCACCTTCA
ACTCCGCCCTCACCTCCGCCCTCACCTCTGCCCACATTATCAACACCTAGCCCCTCTTT
AATGCCTACTGGTTACAAATCCATGGAGCTGAGTGACATTTCCAATGAAAACTGCCGA
ATAAACAGATATGGCTACTTCAGAGCCACCATCACAATTGTAGAGGGGATCCTGGACG
CAGCATCATGCAGATAGCAGATGTCCCATGCCCACACCGCAGCCGTCCAACTCCTGAT
GGACTTCACTGTGACCTCAAGGGCACCCATGGAAGCTGTCAGA     (SEQ ID NO. 111)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTG           (SEQ ID NO. 112)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTGCCCACATTATCAACACCT
AGCCCCTCTTTAATGCCTACTGGTTACAAATCCATGGAGCTGAGTGACATTTCCAATG
AAAACTGCCGAATAAACAGATATGGCTACTTCAGAGCCACCATCACAATTGTAGAGG
GGATCCTGGAAGTCAGCATCATGCAGATAGCAGATGTCCCCATGCCCACACCGCAGCC
TGCCAACTCCCTGATGGACTTCACTGTGACCTGCAAAGGGGCCACCCCCATGGAAGCC
TGTACGATCATCTCCGACCCCACCTGCCAGATCGCCCAGAACCGGGTCTGCAGCCCTG

FIG. 12BB

TGCCTGTCGATGCCCTGTCCTCCTGTCTGTGAGAAGACCCTTCAATGCGTCTGCTACCTACTGTGTGAATTCACTCTCCGAGATGATCCAACCCT (SEQ ID NO. 113)

GGATCCCCTCTACAATTGTGATGGTGGCTCTGAAGTAGCCATATCTGTTTATTCGGCAG
TTTTCATTGGAAATGTCACTCAGCTCCATGGATTTGTAACCAGTAGGCATTAAAGAGG
GGCTAGGTGTTGATAATGTGGGCAGAGGTGAGGGCGGAGGTGAGGGCGGAGTTGAAG
GTGGAGGCGGAGTCGAAGGCGAAGGGGGAGGGCATGGCCCGGGCACTGCAGTTTGCA
CGGTGAGGTTAAGGTTGAAGGTTCCATTGAGCACATAAGTGTGATTCAAAGTGTGATT
GTTGGAGACAAACAGGCCAGTGTTGTCCCAAAGTTCCACTTGTAGGAATGGCAGAGTC
GTTGAGG (SEQ ID NO. 114)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTGCCCACATTATCAACACCT
AGCCCCTCTTTAATGCCTACTGGTTACAAATCCATGGAGCTGAGTGACATTTCCAATG
AAAACTGCCGAATAAACAGATATGGCTACTTCAGAGCCACCATCACAATTGTAGAGG
GGATCCTGGAAGTCAGCATCATGCAGATAGCAGATGTCCCCATGCCCACACCGCAGCC
TGCCAACTCCCTGATGGACTTCACTGTGACCTGCAAAGGGGCCACCCCCATGGAAGCC
TGTACGA (SEQ ID NO. 115)

GAAGGTGGAGGCGGAGTCGAAGGCGAAGGGGGAGGGCATGGCCCGGGCACTGCAGTT
TGCACGGTGAGGTTAAGGTTGAAGGTTCCATTGAGCACATAAGTGTGATTCAAAGTGT
GATTGTTGGAGACAAACAGGCCAGTGTTGTCCCCAAAGTTCCACTTGTAGGAAATGGC
AGAGTCGTTGAGGAAGTGGCTGGGATCATGAATGAGGACATCGAAGACGA (SEQ ID NO. 116)

FIG. 12CC

GAATTCGCACGAGGGGAGTCAGAGTCAAGCCCTGACTGGTTGCAGGCGCTCGGAGTC
AGCATGGAAAGTCTCTGCGGGGTCCTGGGATTTCTGCTGCTGGCTGCAGGACTGCCTC
TCCAGGCTGCCAAGCGATTTCGTGATGTGCTGGGCCATGAACAGTATCCCGATCACAT
GAGAGAGCACAACCAATTACGTGGCTGGTCTTCGGATGAAAATGAATGGGTTCCAATA
TCACTTTTGTGGTGAA (SEQ ID NO. 117)

GAATTCGGCACGAGGAAGGAGGCCGTGTGCAGGCAGTCCTGACCAGTGACTCACCGG
CTCTGGTGGGTTCCAATATCACTTTTGTGGTGAACCTGGTGTTCCCCAGATGCCAGAAG
GAAGATGCTAATGGCAATATCGTCTATGAAGAACTGCAGGAATGATTTGGGACTG
ACATCTGACCTGCATGTCTACAACTGGACTGCAGGGGCAGATGATGGTGACTGGGAAG
ATGGCACCT (SEQ ID NO. 118)

GAAGGTGGAGGCGGAGTCGAAGGCGAAGGGGGAGGGCATGGCCCGGGCACTGCAGTT
TGCACGGTGAGGTTAAGGTTGAAGGTTCCATTGAGCACATAAGTGTGATTCAAAGTGT
GATTGTTGGAGACAAACAGGCCAGTGTTGTCCCCAAAGTTCCACTTGTAGGAAATGGC
AGAGTCGTTGAGGAAGTGGCTGGGATCATGAATGAGGACATCGAAGACGATGGGGAG
GTCTCTGAGGAAGATCTCATCAGACAAGTT (SEQ ID NO. 119)

GAATTCGGCACGAGGTCAAGCCCTGACTGGTTGCAGGCGCTCGGAGTCAGCATGGAA
AGTCTCTGCGGGGTCCTGGGATTTCTGCTGCTGGCTGCAGGACTGCCTCTCCAGGCTGC
CAAGCGATTTCGTGATGTGCTGGGCCATGAACAGTATCCCGATCACATGAGAGAGCAC
AACCAATTACGTGGCTGGTCTTCGGATGAAAATGAATGGATGAACACCTTGTATCCA
(SEQ ID NO. 120)

FIG. 12DD

AAGGGGGAGGGCATGGCCCGGGCACTGCAGTTTGCACGGTGAGGTTAAGGTTGAAGG
TTCCATTGAGCACATAAGTGTGATTCAAAGTGTGATTGTTGGAGACAAACAGGCCAGT
GTTGTCCCCAAAGTTCCACTTGTAGGAAATGGCAGAGTCGTTGAGGAAGTGGCTGGGA
TCATGAATGAGGACATCGAAGACGATGGGGAGGTCTCTGAGGAAGATCTCATCAGAC
AAGTTCCTGTCATTCTTCTGGGACATGGTCACGAATACAGGGATCTGATCTGTTAT (SEQ ID NO. 121)

GAATTCGGCACGAGCCGACACTGTGACTCCTGGTGGATGGGACTGGGGAGTCAGAGT
CAAGCCCTGACTGGTTGCAGGCGCTCGGAGTCAGCATGGAAAGTCTCTGCGGGGTCCT
GGGATTTCTGCTGCTGGCTGCAGGACTGCCTCTCCAGGCTGCCAAGCGATTTCGTGAT
GTGCTGGGCCATGAACAGTATCCCGATCACATGAGAGAGCACAACCAATTA (SEQ ID NO. 122)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 123)

TACCATCGGAGAAAGAAGACCAAGCAAGGCTCAGGCAGCCACCGCCTGCTTCGCACT
GAGCCTCCTGACTCAGACTCAGAGTCCAGCACAGACGAAGAGGAATTTGGAGAATTG
GAAATCGCTCTCGTTTTGTCAAGGGAGACTATCCCGATGCTGCAAGATCTGCTGTCCCT
CTGGCCTTTGTCATCCTCGCGCCTGCGTTGTGGCCTCTGTGGGCTTGGTGTGGAGCAAA
TGGCTCTCAAGGAGGACTGAGTCTCAAGGAAATT (SEQ ID NO. 124)

FIG. 12EE

AGCTAAGGTCAGGAGGTGTCTGAAGAATTGGCTGATGCATGGCAGGGATGTTGTTGAC
CTGCTTTTAGAACAATACTTCCATTTAATTATAGCATATCTTATGTGTGTATTAAAGCA
GAGCCGATCTGGTGGGGCTCATTAAGTAAATGTACTTACTGCAAAAGGTTCAACTGGT
GACCCCAGTTTTCCCCAGAAGCAATATGATAGGACAGAGGCGACTCCTGCAAGTTGTC
TCAGACTTCACACATACATTGTGACATTCTCTGAGCATGTGCACTGTACATGATATGAC
ACTATCAA (SEQ ID NO. 125)

AGCTAAGGTCCACTACCTTGTGAAGATGTATAAACACCTGAAATGTAGAAGCGATCCG
TATGTCAAGATCGAGGGGAAGGACGCTGACGACTGGCTGTGTGTGGACTTTGGGAGTA
TGGTGATCCATTTGATGCTTCCAGAAACCAGAGAAACCTATGAATTAGAGAAACTATG
GACTCTACGTTCTTTTGATGACCTTAGCTAAGCCGAATCAGCACACTGGCGGCGTTACT
AGTGGATCGAGCTCGTACAGCTGATGCATAGCTTGAGTATCTATAGGTTACTAATAGC
TGGCTATCATGTCAAGCGTTC (SEQ ID NO. 126)

GCTGAGCTGCAGAGAGTAGCACATCCTTGCTAATTCAATAACTACCAGTTTTTATTGGT
GAAACATGAATCCAGATGGTATGGTTGCTCTCCTGGACTACCGTGAAGATGGTGTGAC
TCCATTCATGATTTTCTTTAAGGATGGCTTAGAGATGGAGAAATGTTAACAAATTGGA
TCTATCACCTGTCACCATAATTGGCTGCTGCTTACCATCCATACAACACCAGGACTTAG
GACAAATGGGACTGATGTCATCTTGAGCTTTTATTTTGACCTTAGCT
(SEQ ID NO. 127)

AGCTAAGGTCAGAGCCAATAGTATCATGAGAACTGAAGAAGTAATAAAGCAACTTCT
CCAGAAATTTAAGATTGAGAATAGCCCTCGGGATTTCGCTCTTTACATTATTTTTGGGA
CAGGAGAGCAGAGAAAGCTAAAGAAGACCGATGTCCACTGCTGCAGAGGTTACTACA
AGGACCATCCAAAAGCAATGCTCGGATCTCTCATGGATAAAGATGCAGAAGAATCAC
GAGAGATGTGGCTCGTACATTATTTCACTTTCTTCTGATCATACTCAAGATAGATGAGA
GAGAAT (SEQ ID NO. 128)

FIG. 12FF

TTGACTTCTGAGTCTAACACAGACACTGCAAGGGTTAATTTTCCAAGAGGTGGTTGTT
GTTGACGATAAATTCATTAAGAATTTTAAAAATTTAGTTAGATTTACCAAAGTCACTG
GAGACAAATTCAGAAGGCATATATACCTGCCAGTTTTGTGGACTACATTAATAGGGAG
GCTTTTATGTTTGATGTAATTCTTACAGTTCTAAGAATTAAGTTCCATTGCATGAGACC
TTAGCT (SEQ ID NO. 129)

AAGGTGAATCCCCGACGGCTCTGGGCCCGAGGAGAAGCGTCGCCGTGGCAAATTGGC
ACTGCAGGAGAAGCCCTCCACAGGTACTTGGAAAAACTGGTCTCTGAGGCCAAGGCC
AGCTCCGAGACATTCAGGACTTCTGGATCAGCCTCCAGGGACACTGTGCAGTGAGAAG
ATGGCCATGAGTCCTGCCAGTGAG (SEQ ID NO. 130)

AATTTTTTTTTCGACGGCCCAACGGGGGCTTGGTGGATGGAAATATGGTTTTGTGAGT
TATTGCACTACCTGGAATATCTATGCCTCTTATTTGCGTGTACTGTTGCTGCTGATCGT
TTGGTGCTGTGTGAGTGAACCTATGGCTTAGAAAAACGACTTTGTCTTAAACTGAGTG
GGTGTTCAGGG (SEQ ID NO. 131)

CACCTGATTTAAAGGAAAAGCATTCTGACGTAAGAAGCTGAAAGGCGGCCCTTGCGTG
CTTTGAACTTTCTTATACAGCACAGTCATCTGAAGCTTCCTGTGTGACCAAGACAAGA
ACGCGTGCACAAGACTGAGAAACAGCAAGAAACAACCCGGCATTCTACTTTCTCAAC
ACTATCATACTTTAAACCTTTCAC (SEQ ID NO. 132)

FIG. 12GG

CTAGCTTACGCTAGTCCCCCATGCATAAAGACTGATCGCTTTTCCTTAGAAAGGTGAG
AGGGTTAGGACAAGGCCGTGTGGTAACAACACCCGCAGCTCGAAAAACCAATGGCTT
GTTAACGTGTCAGTGAGGCACTGTACGGACGTCCATAGTCCACATCTTCAAATTCCCG
CAGAAGGCTTCCTATTCTTAAACTCTA (SEQ ID NO. 133)

CTACATTTCTGTATCCATTCCTCTGTTGAAGGCTCTGGTTCTTTCCAGCTTCTGGCTATT
ATAAATAAGGCTGCTATAAACACAGTGGAGGCATGTGTCCTTGTTATATTTTGGAGCA
TCTTTTGGGTATATGCCCAGAAGTGCTATAGCTGGTTCCTCAGGTAGTACTATGTCGAA
TTTTCTGAGGAACTGCCAGACTGATTTCCAGAGTGGTTGTACCAGCTTGCAATCCCACC
AGCAATAGAGGAGTGTTCCTCTTTCTCTATATTCTTGCCAACATCTGCTGTCACCTGAG
TGTTT (SEQ ID NO. 134)

TGGTAAAGGGGGAATGATGTCGAGGCCATCCTGGGCTGTAGAGCCAGGCCCTGGCTTG
GGGAGTGGGCATTGTTAACTTGTTGCTGACTTTGTGTTGACCCCTGCATCAGCAACTAT
TTCCTTAAATCCAGGATACAACTTGTTAAGTGTGACAGCTTTCCTTTACACACCATTTT
TGTGGGTGTATATATATATTTGACTTGGGGAGAATTATTTTTTACAAAAATACAAAAT
AGCTTTTAA (SEQ ID NO. 135)

AGCTAAGGTCCGGACTCTATGGCATGACCCCAAAAACATTGGCTGGAAAGATTACACT
GCCTACAGGTGGCACCTGATTCACAGGCCTAAGACAGGCTACATGAGAGTCTTAGTGC
ATGAAGGAAAGCAAGTCATGGCTGACTCAGGACCAATTTATGACCAAACCTACGCTG
GTGGACGGCTGGGCTGTTTGTCTTCTCCAAGAGATGGTCTATTCTCGGACCTCAAGTAT
GAGTGCAGAGATGCTAGAGAGCAGGCTCAGTCTCAGCA (SEQ ID NO. 136)

FIG. 12HH

TGACCTACGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGAGTCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT (SEQ ID NO. 137)

AATTTTTTTTTCGACGGCCCAACGGGGGCTTGGTGGATGGAAATATGGTTTTGTGAGT
TATTGCACTACCTGGAATATCTATGCCTCTTATTTGCGTGTACTGTTGCTGCTGATCGT
TTGGTGCTGTGTGAGTGAACCTATGGCTTAGAAAAACGACTTTGTCTTAAACTGAGTG
GGTGTTCAGGG (SEQ ID NO. 138)

CACCTGATTTAAAGGAAAAGCATTCTGACGTAAGAAGCTGAAAGGCGGCCCTTGCGTG
CTTTGAACTTTCTTATACAGCACAGTCATCTGAAGCTTCCTGTGTGACCAAGACAAGA
ACGCGTGCACAAGACTGAGAAACAGCAAGAAACAACCCGGCATTCTACTTTCTCAAC
ACTATCATACTTTAAACCTTTCAC (SEQ ID NO. 139)

CTAGCTTACGCTAGTCCCCCATGCATAAAGACTGATCGCTTTTCCTTAGAAAGGTGAG
AGGGTTAGGACAAGGCCGTGTGGTAACAACACCCGCAGCTCGAAAAACCAATGGCTT
GTTAACGTGTCAGTGAGGCACTGTACGGACGTCCATAGTCCACATCTTCAAATTCCCG
CAGAAGGCTTCCTATTCTTAAACTCTA (SEQ ID NO. 140)

CTACATTTCTGTATCCATTCCTCTGTTGAAGGCTCTGGTTCTTTCCAGCTTCTGGCTATT
ATAAATAAGGCTGCTATAAACACAGTGGAGGCATGTGTCCTTGTTATATTTTGGAGCA
TCTTTTGGGTATATGCCCAGAAGTGCTATAGCTGGTTCCTCAGGTAGTACTATGTCGAA

FIG. 12II

TTTTCTGAGGAACTGCCAGACTGATTTCCAGAGTGGTTGTACCAGCTTGCAATCCCACC
AGCAATAGAGGAGTGTTCCTCTTTCTCTATATTCTTGCCAACATCTGCTGTCACCTGAG
TGTTT (SEQ ID NO. 141)

TGGTAAAGGGGGAATGATGTCGAGGCCATCCTGGGCTGTAGAGCCAGGCCCTGGCTTG
GGGAGTGGGCATTGTTAACTTGTTGCTGACTTTGTGTTGACCCCTGCATCAGCAACTAT
TTCCTTAAATCCAGGATACAACTTGTTAAGTGTGACAGCTTTCCTTTACACACCATTTT
TGTGGGTGTATATATATTTGACTTGGGGAGAATTATTTTTTACAAAAATACAAAAT
AGCTTTTAA (SEQ ID NO. 142)

AGCTAAGGTCCGGACTCTATGGCATGACCCCAAAAACATTGGCTGGAAAGATTACACT
GCCTACAGGTGGCACCTGATTCACAGGCCTAAGACAGGCTACATGAGAGTCTTAGTGC
ATGAAGGAAAGCAAGTCATGGCTGACTCAGGACCAATTTATGACCAAACCTACGCTG
GTGGACGGCTGGGCTGTTTGTCTTCTCCAAGAGATGGTCTATTCTCGGACCTCAAGTAT
GAGTGCAGAGATGCTAGAGAGCAGGCTCAGTCTCAGCA (SEQ ID NO. 143)

TGACCTACGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGAGTCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT (SEQ ID NO. 144)

TGACCATCGATAAGTTTAATAACTACAGACTTTTCCCAAGACTACAAAAGCTTCTTGA
AAGTGACTACTTTAGATATTACAAGGTGAACTTGAAGAAGCCTTGTCCTTTCTGGAAT

FIG. 12JJ

GACATCAACCAGTGTGGAAGAAGAGACTGTGCCGTCAAACCCTGCCATTCTGATGAAG
TTCCTGATGGAATTAAGTCTGCCGAGCTACAAGTATTCTG
AGGAAGCCCAACCGCATTGAAGAATGTGAGCAAGCTGAGCG (SEQ ID NO. 145)

AACTCTGTGAACCGTGCCTTTCTCTGTGGAGGTGGAGGTGTCGGTTGAAGACAAGCGA
GGTCCTCCAAGGGGCTGTGTCTTATGTTGCCATCTCCCCTTGTAGCTTGGCTGCCCACC
CTCCAGACTGTGCGCCATGGCTCCAAGGCTGTGACCCGCCACTGGAGTCATGCACTTC
CAGCGGCAGAAGCTGATGCTATAACTGAGTATATTCCTCCAAACCTGCCATCAACCCG
AGA (SEQ ID NO. 146)

ACTTCTCCAGAGAATTTAAGATTGAGAATAGCCCTCGGGATTTCGCTCTTTACATTATT
TTTGGGACAGGAGAGCAGAGAAAGCTAAAGAAGACCGATGTCCCACTGCTGCAGAGG
TTACTACAAGGACCATCCAAAAGCAATGCTCGGATCTTCCTCATGGATAAAGATGCAG
AAGAAATCAGCAGAGATGTGGCTCCGTACATTAATTTCACTTTTCTTTCTTGGATCCAT
CCTTCAAGATTAGATGAAGAAGAGAAATGGAGATTGAGAGAATATGCAATCATACCGA
(SEQ ID NO. 147)

AGGGTTACTTCAGGCTAAGGCAATAGAAATCCATTTTAAGATGGTGTGCTAAAGGCTT
GATGGATGTTCATCGTCTGTCTAAAGGAGAATGAAGTCATCAACAGGATGTCAGGGGA
AAGTGAGATCATCGCAGAAAGTATCAACTTAGCACAAACACACAGGCATAGCTCCTG
CAAGAGGTGAATGCTGTCCCCAAATACCTGAGGAACTATCCCTTTGGGCAAGAAAATA
GACAAGTCCATGAAGTCTGGGTGA
(SEQ ID NO. 148)

GACCAGGTACACTTGAGCAAAGCACCCAGTATTTAATTCCTTACAGAAAGGAGAGGA
AAGGTCTGCAGTTGGACTGATGGTATGCTAACACCGCAAATGACTGTCATTTGATCTC

FIG. 12KK

AGAAGTTCAGGATTGATTGCTATGTTTTAGCTCTAATTGTGAGAAACAGTAGTCATTTT

AGTCTTAAATTTTGCCCTCAGGAAATTCAGGGAGACTGAGCCTTCCTTCCCCCACCTTC

GTAAAGCCGAATTCCAGCACACGGCGGCCGTTACTAGTGGATCCGAGCTCG (SEQ ID NO. 149)

TACAAGGTGGGATGGCAGGAACTGAAGGCTTCTGTAAATCCAGTTTTGGCTCTCTCTC

TGGTCTTTCTTTCTCTTCTGTTCTGTTTGGAAGGGTTTCTGGTCTTTCAGGAGGTATTTT

TTTAATTTCATGTTTTCTCTCTGTGGTACCTGCCCCTTGTTTGACGACAGGAGCTGATG

GAGGTGGCGGTTTCTTGGGTCTATTCCCTTCCTTGTCAAAGTCCGATGGAAGTAACTTC

ACGAAGTTGTCAGGAAACACGCCTCGTCTGCCATTGAGTTCTCCTTCCCACCAGCCTA

CGCGATGCAGTCTTATTGATGAGAGTCACTATATCTCCTTA    (SEQ ID NO. 150)

TCACCCATGACTTCTATGGACTTGTCTATTTTCTTGCCCAAAGGGATAGTTCCTCAGGT

ATTTGGGGACAGCATTCACCTCTTGCAGGAGCTATGCCTGTGTGTTTGTGCTAAGTTGA

TACTTTCTGCGATGATCTCACTTTCCCCTGACATCCTGTTGATGACTTCATTCTCCTTTA

GACAGACGATGAACATCCATCAGGCCTTTATGCACACCATCTTAAAATGGATTTCTAT

TGCCTTAGCCTGAAGTCC    (SEQ ID NO. 151)

CCCATAGAGATAGGTTTGCTCCAGAACCTGCAGCATTTGCACATCACAGGGAACAAGG

TGGACATTCTGCCAAAACAGTTGTTTAAGTGCGTGAAGTTGAGGACTTTGAACCTGGG

GCAGAACTGTATCGCCTCCCTGCCTGAGAAAATCAGTCAGCTCACCCAGCTCACTCAG

CTGGAGCTGAAGGGCAACTGCCTAGACCGCCTGCCAGCCCAGCTGGCAGTGTCGATGC

TCAAGAAGA    (SEQ ID NO. 152)

CAATAATCCAGGTAAAATAGAGTAAAATAGTCTGCTAGCAGCAAGTTCCTACCATACT

TTCAACAACACTCACGAGATACGGAATGATTACAGCATTAAGAATATTTCAGAAATGA

CAGGTAGGTGTGGTGGACAGGTGGCTCACATTCAAGACTCAAGTCTACTTAAAAAAGA

FIG. 12LL

AAATCTCACTAGCACTAGATTCTAGCTCCTTTGTTTCCCCCTTTCTTTTGGTTTCAAAG
GCGTTTCTACAACCCATAAGAGG (SEQ ID NO. 153)

GCCAAGCTATTATGACACTATAGATACTCAACGTATCGATCAACGTTGGTACCGAGCT
CGGATCCACTAGTAACGGCCGCCAGTGTGCTGGAATTCGGCTTGGATTGGTCAGAGCA
GTGTGCAATATGATCCAACTAAGTCTCCTCCCTTGGCCCCTCCCCAAAATGTTTGCAGT
GTTATTTTTGTGGGTTTTTTTTAACACCCTGACACCTGTTGTGGACATTGTCAACCTTT
GTAAGAAACCCAAATAAAATTGAAAAATAAAATAAAAGAAACCCATGAACATTC
GCACCACTTGTGGCTTCTGACTATCTTCCACAGAGGGAAGTTTAAAACCCAAACTTCC
AAAGGTTTGAACTACCTCAAGACACTTTCGCAGTGGAGTCGTAGACCAATCCCA (SEQ ID NO. 154)

TAAATAAATTAAAAAACTATTAAACCTAAAAACGTCCACCAAACCCTAAAACCATTAA
ACAACCAACAAACCCACTAACAATTAAACCTAAACCTCCATAAATAGGTGAAGGCTTT
AATGCTAACCCAAGACAACCAACCAAAAATAATGAACTTAAAACAAAAATA (SEQ ID NO. 155)

GGTAAAGGGGACCTGGAGAACGCCTTCCTGAACCTGGTCCAGTGCATCCAGAACAAG
CCCCTGTACTTCGCTGACCGGCTGTACGACTCCATGAAGGGCAAGGGGACTCGAGACA
AGGTCTGATTAGAATCATGGTCTCTCGCAGTGAAGTGGACATGCTGAAAATCAGATCT
GAATTCAAGAGGAATATGGCAAGTCCTGTACTACTACAT (SEQ ID NO. 156)

AGAGCAGCAGGCCAGCTGTACTTGGTTTGGCAAGAAAAGAAGCAGTACAAAGATAA
ATATTTGGCAAAGCACAACGCAGTGTTTGATCAATTAGATCTTGTCACATATGAAGAA
GTAGTCAAACTGCCAGCATTCAAAAGGAAAACATTAGTCTTATTAGGTGCACATGGTG
TTGGAAGAAGACACATAAAAAATACCCTCATCACAAAGCAC (SEQ ID NO. 157)

FIG. 12MM

TCGGTCATAGTAGTAAGGGAAATCTCCCAGGTAAGATGAATACTGCGGTAGGACGAA

CAATCCTCCAGGATGTTTGTTCCATATTAAACTGTTACGTGATATGTGCTTGAATATTC

TGTCCTGAATAATCTCTAGTGTAGTTAATACAATCTTCTCAACTGAAGAAAAATAAGC

CTCCCACAAGAACTGTGTCTGCTGTCTAAGTGCTAGGATTTTATCCTGATGAATAGACC

TGATTGTAGAAGGAATCTGTAATAGCAATCTCTCATCGCCTATGACCGAAAGCCGAAT

TCTGCAGATATCCATCACACTGGCCGGCCGCTCGAGCATCGATCTAGAGGG (SEQ ID NO. 158)

CTGCTTGATGACAAAGGGTGTAGTCTTCATCTTTTCCTGGATTATTTTGGAAGTGACAG

GTGGAAATTCCATCGTCACGTTTATGTGGTCTGTAAAGCCAACGATCTCAAATTCTGG

CGGCTCAAGAGGAGCGTTTGCAGGCACGATGTAGTCTGAGCAGCGGCACACGGTCAA

GTCCCCTCTGTGCACTATGACGATGGCGACGACGTAGCTCTCCATGCCCTCCAACCAC

TTATCTGTCACGTCACATGATGACTTCGTGGTATCTGAACAGTTCTTAACCTTCGTCAG

ATTTTCGTCTTT (SEQ ID NO. 159)

AAATCGTTGCTTCAGAAAGACTCAATAACACTTACTTGTGCCTGGCTGTGCTGACAGT

ACATTCTGTGTCATTTTCCTTCATGGGCGGAACAGTCCACAGAGCTCACCAACAAGTA

CTCCAAAACTGAGCAAGAGTTTAAGCTTCGAGATGCAACCAGATGAGCTTCTAGAAAA

GCCCATGTCTCCCATGCAGTACGCACGGTCTGGACTAGGGACAGCAGAGATGAATGGC

AAACTCATAGCTGCAGGTGGTTATAACAGAGAGGAATGTCTTCGAACAGTTGAATGCT

ATGATCCACATACAGATCACTGGTCCTTCCTTGCTCCATGAGAACATCAAGCAG (SEQ ID NO. 160)

CTTTCCGAAGAGCACACCCTCCTCTCAATGAGCTTGTGAGGTCTCTTTCTTCTCTTCCT

TCCAACGTGGTGCTAGCTCCAGGCGAGCGACGTGAGAGTGCCACCTGAGACAGACAC

CTTGGTCTCAGTTAGAAGGAAGATGCAGGTCTAAGAGGAATCCCCGCAGGTCTGTCTG

AGCTGTGATCAAGAATATTCCGCAATGTGCCTTTTCTGAGATCGTGTTAGCTCCAAAG

FIG. 12NN

CTTTTTCCTATCGCAGAGTGTTCAGTTTGTGTTTGTTTGTTTTTGTTTTGTTTTGTTTTTC

CCTTGGCGGATTTCCCGTGTGT (SEQ ID NO. 161)

CCTATTGAACGGTCTTGCAATGACGAGCATTCAGATGCTTAAGGAAAGCATTGCTGCT

ACAAATATTTCTATTTTAGAAAGGGTTTTTATGGACCAATGCCCCAGTTGTCAGTCAA

AGCCGTTGGTGTTTTCATTGTTTAAAATGTCACCTATAAAACGGGCATTATTTATGTTT

TTTTTCCCTTTGTTCATATTCTTTTGCATTCCTGATTATTGTATGTATCGTGTAAAGGAA

GTCTGTA (SEQ ID NO. 162)

CCTATTGAACGGTCTTGCAATGACGAGCATTCAGATGCTTAAGGAAAGCATTGCTGCT

ACAAATATTTCTATTTTAGAAAGGGTTTTTATGGACCAATGCCCCAGTTGTCAGTCAA

AGCCGTTGGTGTTTTCATTGTTTAAAATGTCACCTATAAAACGGGCATTATTTATGTTT

TTTTTCCCTTTGTTCATATTCTTTTGCATTCCTGATTATTGTATGTATCGTGTAAAGGAA

GTCTGTA (SEQ ID NO. 163)

CCTGGGTCCGTCCTCCAACCCCTCACGCCCAAACCCTCCGACTTTCACTTCTTGAAGTG

ATCGGAAAGGGCAGTTTTGGAAAGGTTCTTCTGGCTAGGCACAAGGCAGAAGAAGTA

TTCTATGCAGTCAAAGTTTTACAGAAGAAGCCATCCTGAAGAAGAAAGGAAGGAAGC

ATATTATGTCAGAGCGGAATGTTCTGTTGAAGAATGTGAAGCACCCTTTCCTGGTGGG

CCTTCACTTCTCATTCCAGACCGCTGACAAGCTCT (SEQ ID NO. 164)

GATGCTGAACACAAAAGAAAGAAGAAAAGGAAGAGGAGGAGCAAGAGAAGCTGAA

GGGAGGGAGCCTTGGCGAAAATCAGATCAAAGATGAAGATTAAAAAGGACAAAG

AGCCCAAAGAAGAGTCAAGAGCTTCTTGGATAGAAAGAAAGGATTTACAGAGTGAGG

CGCAGAATGGAGATTCATGACCCACAAACTTAAAC

FIG. 12OO (SEQ ID NO. 165)

AAAGCCAATTGGTAGAGAAATTGAAGACACAAATGCTGGATCAGGAAGAGCTTCTGG
CATCAACCAGAAGGGATCAAGATAATATGCAAGCTGAACTGAATCGCCTCCAAGCAG
AAAATGATGCTTCTAAAGAAGAGTAAAGAGTTTTACAGGCCTTAGAGGACTGCTGTTA
ATTATGATCAGAGTTCAGGAGTTAAGAC (SEQ ID NO. 166)

CTGCTTGATGTCCTGTGTAGCGAATGTCACAGCGTACAACATTGTTAGTGTAGTCTGAT
TCAGGCACCAGGTAGCTGGGGTTTACACTGACCTTTAGAATGTAGTTTCCAGGTTGTA
CATCTGTAATATCAATCCACTGGCAGTCTATGTCTGCCGCATAGGTGTCATAACATCCA
GGACTCAATCCCTGTGTGTGTGCAGTGCACGCAAAGGCCCTGTGGTACCCATAGTCAC
AGGACGTGTCCTCCAGACAGAAGCTTGCTTTGTGGCCTTCAGCCACTCTCCTCTGTGTG
TTGGCATCAACGAGAAGCCGAATTCTCGAGATATCCATCACACT (SEQ ID NO. 167)

CTGCTTGATGTCCTGTGTAGCGAATGTCACAGCGTACAACATTGTTAGTGTAGTCTGAT
TCAGGCACCAGGTAGCTGGGGTTTACACTGACCTTTAGAATGTAGTTTCCAGGTTGTA
CATCTGTAATATCAATCCACTGGCAGTCTATGTCTGCCGCATAGGTGTCATAACATCCA
GGACTCAATCCCTGTGTGTGTGCAGTGCACGCAAAGGCCCTGTGGTACCCATAGTCAC
AGGACGTGTCCTCCAGACAGAAGCTTGCTTTGTGGCCTTCAGCCACTCTCCTCTGTGTG
TTGGCATCAACGAGAAGCCGAATTCTCGAGATATCCATCACACT (SEQ ID NO. 168)

GATCTGACACTACAGCATGAGCGTTAGATTTCATAAAATTATTTTTCTTCTAAATGCTG
GAAACTCTAAGGGTTTATTCAGAAAAAAAACTGGCCAATTTTCAAATGGCTTAGAAGC
AGGGTTAATTAAGTATTGAATGAGCCACTGTGATATCCTGATGACACCCAGTCACAAT
GACAGTTTTGAAGCATACAACCAAAACAATTGAGATCTCAAAACTATTTTACATCACT
TATGGTAATGTTATGTAAAAATGAAAATGCTTTCTGTGGAAGTTACATTCTTTACCAGG
TCTTTAACATAAATTAACACGACGTCGAGTAAGCCTTTGTTCGGAAGACAAACTAGTT
TGTGAGTTCAGTCAGATCCCAGCT (SEQ ID NO. 169)

FIG. 12PP

AGTTGCCAGGACCACCACCATAGTTGCCAGGTTCATCATAAACAAATCCAACATCAAT

CTTAAATTCCCCCATCAGACAATCTGCCCTCAAAGAATGGGAATTATAAACCCGGATA

CTGATGATCTCATCCATGAGCTCAGAGGGTGTGATGTGCACATTGTAGAAAAATAACT

CGTCAAAAAACGGATTGTTCCCTCTCTTGATTCTCGTGCGATGCGTCTGACCACAGATG

TGAACTTTCACCACGGGCCTTATGTTGTTGCCGCATAACTGACGGCCCTCGATCACTCT

GACACGGATCTGGAAATCTGTGGCTTGTTGGACAGCATCCTT          (SEQ ID NO. 170)

AAGCCGTGTCCCAAAGAATGGATAGAGACGCGATCAGATGCGACAGTGCTGTGGAGA

AAGCCCAGGAACCTGCACAATTGCCCTGGTCCAATGGCTCGTGGATCAGGTTGGGCCA

CTTCTCTGAAGCTTCAAAGGCAGTGGGTAGCACTTCCCCTTGGCCCAGCACCGTATAA

ATCTCATTCATATTCATGACAGTGGAGGATGGGCGGATTGTGCCCAGGCGGTACGGAA

TGCCCTCATCCAGGGTCATGCCCCAGAAGGCACTGTGGTTCCCAGCCTGCCACCCGTA

GTTGCCTCGGTTGATGGCTTTAATCATGTCTGGTCACTAGACACGGCTTAAGCGAATCT

CGAGATATCCATCACACTGGCGGCGTCGAGAT            (SEQ ID NO. 171)

AAGCCGTGTCTGATGATGGAGGTAGTGGTGGGGGAGGAGGGACTGAGGGTCCTGAGG

TGGTGGCCCCTGGAACTGATCCCACATAGTTACCCACTGCTAGTTCTGACCCCGTGGA

CAACGTGCCAGAGGCCATGACTGGCAGTATGGCAATGTCCCCATCCCCTTTCTTCTTA

ATTTTAATGGTCCCTTGTTTCTCCAGTTCGTGAATCTTTTTTTCCAGGGTAGACTGTCTT

TGAATGGCTTCTTCCTTTTCTTTGACCATTTTTCTTAACGTGTGAACTTGGGTATTTGCA

TCTTTGTAGATTTCCGGACAACATCAGTTCCTTATTCCTCTGCATAAGTTGCTTTCAGTT (SEQ ID NO. 172)

CGAGTCAGACACATGAAAGCAAAACGCGGGCAGATAAAACGATCGCCTTACCTTCTA

GCAAAAATCTGAAGCTTGTGTCAGAAACAAAGACTCAGAAAGGTTTGTTTTCAGATGA

AGAAGACTCTGAGGATTTGTTTTCTTCTCAAAGTTCAAGTAAGCCAAAAAGTGCATCA

FIG. 12QQ

CTTTCATCCAGCCAGCCCCCAACATCAGTCTCCCTTTTGGTGATGAAGATGAAGAGG
ACAGTCTTTTTGGGAGTGCAGCAGCTAAGAAGCAGACTTCATCTCTACAACCTCAGAG
TCAAGAGAAAGCAAAGCCTTCCGAGCAGCCCTCAAAGAAGACATCTGCCTTGTTGTTC
AGA (SEQ ID NO. 173)

CGAGTCAGACTTAATTTAAAAACGAAACAAAACAAAAATAACATAGTTTAGAAATCA
AGGAGAAAGGACAGATAGTCTAAGAAAAAAGACAACACAAAAGAGGGGCAGGGCGG
CCAGCTTGCATCAGGGATCTTGGCTGGAGACCTGCTTTGAATAGGTTTCTTGCAGGTAT
TTCTTAAATGCTGTGGGGTTTTTCCAGAGTTCCGCAGCGTGTGTGTTCAAAGGGCTATC
GATGTTGGGTTCTCCTAGCAGGCTCTGGATAGAGAGCAAGATAGTCCTGACATCATAT
AGTGCAGACCACTTATCCTTGAGGATGTCCGGCAGATGTTGCCTGGGTGTCACGTTGG
GGTGGTAGCAGGGTGTGAGGAACTTCACTG (SEQ ID NO. 174)

CGAGTCAGACACTCCTGGCTCCTGGATTCTTTAGATGCCTCCATCAGACTGGGTACTTT
AGATGCCTCCATCAGACTACTTCGTCATTGTATTTCTCAGTTCGCTCAGGGCAAGCGGC
AGTCTCTGGGCTGCTGTGGCAGGTGCCACCACTGCATTTAAAAGTTAAAATTTCTTCA
AATATTCCCATCAAGGCCTTGTAGCCTCTGAGATTGGTTTACTATTTGCCCAGTTATTT
AAAGCTCTCTGCATTCCTTCCTGATTTAATATTGCTATGGCCAGGACAATGTGTAGAAG
TAAAAAGGATATCATATTTACAGGTGTAACGC (SEQ ID NO. 175)

FIG. 12RR

| DD-PCR PRIMER AND PCR SIZE (nt) | cDNA FROM CELL LINE | MOUSE HOMOLOGY (%nt) | HUMAN HOMOLOGY (%nt) | NORTHERN (SCREEN 1) | NORTHERN (P-MT) (SCREEN 1) | NORTHERN-CLONED DNA (P-MT) (SCREEN 2) |
|---|---|---|---|---|---|---|
| P17-6 cl10 (1100) | 151-1 LM1 | MUSCLE NICOTINIC ACETYLCHOLINE RECEPTOR APLHA (54.3%) | | | NO | 151-1LM1 UP, 151-1LMA DOWN |
| P19-6 cl2 (500) | 151-2 PA | | LYMPHOCYTE IgE RECEPTOR (52.6%) | | NO | 151-2LMA DOWN,DOWN |
| P21-6 cl3 (450) | 151-2 PA | HISTON H2b (94.2%) | | | 151-1LM1 DOWN,DOWN | 151-1LM1 DOWN,DOWN |
| P21-9 cl6 (500) | 151-1 PB | RATTUS NORVEGICUS THIOL-SPECIFIC ANTIOXIDANT mRNA(94.4%) | | | 151-1LM1 DOWN,DOWN 151-2LMA UP,UP | 151-1LM1 DOWN,DOWN 151-2LMA UP,UP |
| P21-17 cl9 (1000) | 148-1 LMD | MUS MUSCULUS PUTATIVE PROTEIN TYROSIN PHOSPHATASE mRNA(98.3%) | | | 148-1LMD UP,UP 151-1LM1 UP,UP | 148-1LMD UP,UP 151-1LM1 UP,UP |
| P22-5 cl3 (600) | 148-1 LMD | RAT DIHYDROPYRIDINE-SENSITIVE L-TYPE CALCIUM CHANNEL ALPHA-2 SUBUNIT GENE (92.5%) | | | 148-1LMD UP,UP | 148-1LMD UP,UP |

FIG. 13A-1

| | | | | |
|---|---|---|---|---|
| P22-6 cl4 (600) | 148-1 LMD | SAME AS P22-5 Cl3 | | 148-1LMD UP 151-1LM1 UP | 148-1LMD UP,UP |
| P22-9 cl3 (800) | 148-1 LMD | RAT KIDNEY ZN-PEPTIDASE AMINOPEPTIDASE N mRNA (90.5%) | | 148-1LMD UP,UP,UP | 148-1LMD UP,UP,UP |
| P24-6 cl3 (550) | 151-1 PB | | UBIQUITIN CARRIER PROTEIN (E2-EPF) mRNA (53.3%) | 151-1LM1 DOWN 151-2LMA UP 151-2LMB UP | 151-2LMA UP |
| P24-10 cl3 (1400) | 151-1 LM1 | RATTUS NORVEGICUS CALPAIN II 80 kDa SUBUNIT mRNA (93%) | | 151-1LM1 UP,UP | 151-1LM1 UP,UP |
| P25-1 cl3 (400) | 148-1 PA | M. MUSCULUS KERATINOCYTE GROWTH FACTOR Fgf-7 (99.4%) | | 148-1LMD DOWN 151-1LM1 DOWN,DOWN 151-2LMB UP,UP 151-2MMA UP | 148-1LMD DOWN 151-1LM1 DOWN 151-2LMB UP 151-2LMMA UP |
| P25-9 cl8 (1300) | 151-1 PB | M. MUSCULUS mRNA FOR INSULIN-LIKE GROWTH FACTOR BINDING PROTEIN-3 (98.1%) | | 148-1LMD UP 151-1LM1 DOWN,DOWN,DOWN 151-2LMA UP,UP,UP | 148-1LMD UP 151-1LM1 DOWN,DOWN,DOWN 151-2LMA UP,UP,UP |
| P2-27 (cl18-3) | 148-1 PA | RATTUS NORVEGICUS GLYPICAN mRNA (93.4%) | | | 148-1LMD DOWN P53(+)12 DOWN |

FIG. 13A-2

| CLONE # | cDNA FROM CELL LINES | DD PRIMER | PCR SIZE (nt) | MOUSE HOMOLOGY | HUMAN HOMOLOGY | NORTHERN BIG BIOT # | REGULATION TYPE | SEQUENCING PRIMER | SEQUENCING LENGTH |
|---|---|---|---|---|---|---|---|---|---|
| Cl 3#1<br>Cl 4#1<br>(SAME FRAG & ORIENTATION) | 151-2 LMB | P3 | | TYROSINE KINASE? VIP2 | CAVEOLIN (70%) | N123<br>148-1 UP<br>151-1 UP<br>151-2 UP | UP | -40 | 241<br>156 |
| Cl 5A#4 | 148-1 PA | P2 | | THROMBO-SPONDIN 100% | THROMBO-SPONDIN | N124<br>148-1 DOWN<br>151-1 DOWN<br>151-2 UP | DOWN | -40 | 233 |
| Cl 25#3 | 151-2 LMA | P5 | | | 53BP2 P53-BINDING PROTEIN (53.3%) | 148-1 DOWN<br>151-1 DOWN<br>151-2 UP | DOWN | | |
| Cl 29#3<br>Cl 28#1<br>(SAME FRAG; DIFFERENT ORIENTATION) | 148-1 LMD | P5 | 335<br>332 | | TGF-BETA 2 (53.0%)<br>Kvi-1<br>nmls(53.0%) | N119<br>148-1 UP<br>151-1 UP<br>151-2 UP | UP | T7 | 335<br>332 |
| Cl 54A#2 | 141-1 PA | P8 | | MUSCULUS RECEPTOR TYROSIN KINASE CYCLIN G | PROTO-ONCOGENE TYROSINE PROTEIN KINASE GENE | N126<br>148-1 DOWN (WEAK)<br>151-1 DOWN (WEAK)<br>151-2 UP (WEAK) | DOWN | Sp6 | 220 |

| | | | | | | |
|---|---|---|---|---|---|---|
| CI 63#4 | 151-2 LMA | P10 | | Y316 GENE (53.8%) 1AC GENE (53.8%) Rb SUSCEPTI-BILITY GENE (50%) | N127 | UP | Sp6 | 340 |
| CI 74#2 | 151-2 LMA | P11#3 | 86.8% SERUM & GLUCOCORTICOID REGULATED KINASE (sgk) | | N120 148-1 UP 151-1 DOWN 151-2 UP | | Sp6 | 320 |
| CI 75#1 | 151-2 LMA | P11#10 | 87% MATCH sgk | | | | Sp6 | 250 |
| CI 78B#4 MATCH THE SAME GENE BUT DIFF. FRAG. | 148-1 LMD | P12 | 92.2% MATCH sgk | PROTEIN KINASE C-L (57%) | | UP | Sp6 | 270 |

| DD-PCR PRIMER AND PCR SIZE (nt) | MOUSE HOMOLOGY (%nt) | HUMAN HOMOLOGY (%nt) | TGF-BETA STIMULATORY RESPONSE (12 hr.) | NORTHERN (P-MT) | CELL LINE |
|---|---|---|---|---|---|
| P11-2 cl5 (310) | LYSYL OXIDASE (100%) | | ⇑⇑⇑ | ⇓ | N132: 148-1 LMD, 151-1 LM1 DOWN, 151-2 LMB, 151-2 LMC UP |
| P20-23 cl9 (850) | ACTIN BINDING PROTEIN(100%) | | ⇑⇑ | ⇑⇑ | N142: 148-1 LMD, 151-2 LMA,LMB,MMA UP, 151-1 LM1 UNCHANGED |
| C129-3 (P5) (335) | | NMB(79.8%) | ⇓⇓ | ⇑⇑ | N119: 148-1 LMD 151-1 LM1, 151-2 LMA,LMB,LMC,MMA UP |
| P17-3 cl8 (1000) | UBIQUITIN ACTIVATING ENZYME E1(100%) | ALPHA ACTININ 3 mRNA (77.5%) | ⇑ | ⇓⇓ | N142: 151-2 LMA DOWN |
| P20-3 (400) | | | ⇑⇑ | | |
| P18-12 cl3 (1000) | RAT mRNA FOR P34 PROTEIN (89.6%) | | ⇑ | ⇑⇑ | 148-1IMD UP |
| P25-7 cl3 (1000) | M.MUSCULUS mRNA FOR P19-PROTEIN TYROSINE PHOSPHATASE (100%) | | ⇑ | | |
| P19-1 cl3 (310) | | POLYMORPHIC LOCI IN Xq28 (30%) | ⇑ | | |

FIG. 13C

| DD-PCR PRIMER AND PCR SIZE (nt) | MOUSE (RODENT) HOMOLOGY (%nt) | HUMAN HOMOLOGY (%nt) | SCREEN 1 P53 STIMULATORY RESPONSE (12h. OR 24h.) | SCREEN 2 CLONED DNA |
|---|---|---|---|---|
| P1-8 cl10 (1000) | | DYSTROPHIN GENE (50.4%) | P53(+)24 DOWN,DOWN | P53(+)24 DOWN,DOWN |
| P1-9 cl10 (500) | M.MUSCULUS mRNA FOR CYCLIN G (96.5%) | | P53(+)12 UP,UP P53(+)24 UP,UP,UP | P53(+)12 UP,UP,UP P53(+)24 UP,UP,UP |
| P7-4 cl1 (600) | RATTUS NORVEGLOUS SGK mRNA (51.3%), RAT LUNG DERIVED LOI C-ros-1 PROTO-ONCOGENE mRNA (48.4%) | NITRIC OXIDE SYNTHASE (47.1%) | 148-1LMD DOWN P53(+)12 UP,UP P53(+)24 UP,UP,UP | P53(+)12 UP P53(+)24 UP |
| P9-17 cl9 (500) | RAT mRNA FOR CYCLIN D1 (79.1%) | | P53(+)24 UP | P53(+)24 UP |
| P9-20 cl3 (850) | | H. SAPIENS LDLC mRNA (51.8%) | P53(+)12 DOWN P53(+)24 DOWN,DOWN | P53(+)24 DOWN |
| P11-23 cl2 (800) | SYRIAN HAMSTER GENE FOR CYTOCHROME P-4 (52.5%), RAT CARBOHYDRATE BINDING RECEPTOR GENE (50.6%) | | P53(+)24 UP,UP | P53(+)24 UP |
| P15-9 cl1 (600) | MOUSE (CLONE BALB11N) mRNA (47.2%) | PTGS2 GENE FOR PROSTAGLANDIN ENDOPEROXIDE SYNTHASE-2 (46.6%) | P53(+)24 DOWN | P53(+)24 DOWN,DOWN |
| P15-14 cl5 (500) | | | P53(+)12 UP P53(+)24 UP | P53(+)24 UP |
| P18-23 cl10 (500) | | | 148-1LMD DOWN P53(+)12 DOWN P53(+)24 DOWN | 148-1LMD DOWN P53(+)12 DOWN P53(+)24 DOWN |

FIG. 13D

SEQUENCE LISTING ( 1 ) GENERAL INFORMATION:

( i i i ) NUMBER OF SEQUENCES: 175

( 2 ) INFORMATION FOR SEQ ID NO:1:

( i ) SEQUENCE CHARACTERISTICS:
        ( A ) LENGTH: 9 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

TGACAATCG        9

( 2 ) INFORMATION FOR SEQ ID NO:2:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:2:

AGCTAAGGTC        10

( 2 ) INFORMATION FOR SEQ ID NO:3:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

TCTGCGATCC        10

( 2 ) INFORMATION FOR SEQ ID NO:4:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

ATACCGTTGC            10

( 2 ) INFORMATION FOR SEQ ID NO:5:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

TACGAAGGTG            10

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:6:

TGGATTGGTC            10

( 2 ) INFORMATION FOR SEQ ID NO:7:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:7:

CTTTCTACCC  10

(2) INFORMATION FOR SEQ ID NO:8:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:8:

GGAACCAATC  10

(2) INFORMATION FOR SEQ ID NO:9:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:9:

TGGTAAAGGG  10

(2) INFORMATION FOR SEQ ID NO:10:

(i) SEQUENCE CHARACTERISTICS:
    (A) LENGTH: 10 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:10:

TCGGTCATAG 10

( 2 ) INFORMATION FOR SEQ ID NO:11:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:11:

CTGCTTGATG 10

( 2 ) INFORMATION FOR SEQ ID NO:12:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:12:

GATCAAGTCC 10

( 2 ) INFORMATION FOR SEQ ID NO:13:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:13:

GATCCAGTAC 10

( 2 ) INFORMATION FOR SEQ ID NO:14:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:14:

GATCACGTAC                                          10

( 2 ) INFORMATION FOR SEQ ID NO:15:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:15:

GATCTGACAC                                          10

( 2 ) INFORMATION FOR SEQ ID NO:16:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:16:

TTAGCACCTC                                          10

( 2 ) INFORMATION FOR SEQ ID NO:17:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:17:

ACCTGCATGC    10

( 2 ) INFORMATION FOR SEQ ID NO:18:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:18:

GCTATACTGC    10

( 2 ) INFORMATION FOR SEQ ID NO:19:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:19:

AGTTGCCAGG    10

( 2 ) INFORMATION FOR SEQ ID NO:20:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:20:

AAGCCGTGTC    10

( 2 ) INFORMATION FOR SEQ ID NO:21:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

TCAACGCTCA 10

(2) INFORMATION FOR SEQ ID NO:22:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

TGTTCGAATC 10

(2) INFORMATION FOR SEQ ID NO:23:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

CGAGTCAGAC 10

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

( x i ) SEQUENCE DESCRIPTION: SEQ ID NO:24:

TATGAGTCCG                                                                                                          10

( 2 ) INFORMATION FOR SEQ ID NO:25:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:25:

GTGTTTCATT AGTTCCCCAC CTTGAC                                                                                        26

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:26:

AGAGCAAGAA TAAGTCAGAA GCCG                                                                                          24

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:27:

ACAGACCGTG CTTCCACCTC GTC                                                                                           23

( 2 ) INFORMATION FOR SEQ ID NO:28:

( i ) SEQUENCE CHARACTERISTICS:
        ( A ) LENGTH: 23 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:28:

CCTCATCTCC TGGGTCCCTT TCA 23

( 2 ) INFORMATION FOR SEQ ID NO:29:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:29:

GTCCGCGCCA TGGCCATATA 20

( 2 ) INFORMATION FOR SEQ ID NO:30:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:30:

ATGGGAGGCT GCCAGTCCTA ACCC 24

( 2 ) INFORMATION FOR SEQ ID NO:31:

( i ) SEQUENCE CHARACTERISTICS:
        ( A ) LENGTH: 234 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:31:

```
AATTTTTTT   TTCGACGGCC   CAACGGAATT   TTTTTTTCG   ACGGCCCAAC   GGAATTTTTT       60
TTTTCGACGG   CCCAACGGGA   ATTCGGCTTA   GCTAAGGTCA   CCCAGACTTC   ATGGACTTGT     120
CTATTTCTT    GCCCAAAGGG   ATAGTTCCTC   AGGTATTTGG   GGACAGCATT   CACCTCTTGC    180
AGGAGCTATG   CCTGTGTGTT   TGTGCTAAGT   TGATACTTTC   TGCGATGATC   TCAC          234
```

( 2 ) INFORMATION FOR SEQ ID NO:32:

( i ) SEQUENCE CHARACTERISTICS:
        ( A ) LENGTH: 266 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:32:

```
TACCATCGGA   GAAAGAAGAC   CAAGCAAGGC   TCAGGCAGCC   ACCGCCTGCT   TCGCACTGAG      60
CCTCCTGACT   CAGACTCAGA   GTCCAGCACA   GACGAAGAGG   AATTTGGAGA   ATTGGAAATC     120
GCTCTCGTTT   TGTCAAGGGA   GACTATCCCG   ATGCTGCAAG   ATCTGCTGTC   CCTCTGGCCT     180
TTGTCATCCT   CGCGCCTGCG   TTGTGGCCTC   TGTGGGCTTG   GTGTGGAGCA   AATGGCTCTC     240
AAGGAGGACT   GAGTCTCAAG   GAAATT                                                266
```

( 2 ) INFORMATION FOR SEQ ID NO:33:

( i ) SEQUENCE CHARACTERISTICS:
        ( A ) LENGTH: 300 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:33:

```
AGCTAAGGTC   AGGAGGTGTC   TGAAGAATTG   GCTGATGCAT   GGCAGGGATG   TTGTTGACCT      60
GCTTTTAGAA   CAATACTTCC   ATTTAATTAT   AGCATATCTT   ATGTGTGTAT   TAAAGCAGAG     120
CCGATCTGGT   GGGGCTCATT   AAGTAAATGT   ACTTACTGCA   AAAGGTTCAA   CTGGTGACCC     180
CAGTTTTCCC   CAGAAGCAAT   ATGATAGGAC   AGAGGCGACT   CCTGCAAGTT   GTCTCAGACT     240
TCACACATAC   ATTGTGACAT   TCTCTGAGCA   TGTGCACTGT   ACATGATATG   ACACTATCAA     300
```

( 2 ) INFORMATION FOR SEQ ID NO:34:

( i ) SEQUENCE CHARACTERISTICS:
        ( A ) LENGTH: 312 base pairs
        ( B ) TYPE: nucleic acid
        ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:34:

```
AGCTAAGGTC CACTACCTTG TGAAGATGTA TAAACACCTG AAATGTAGAA GCGATCCGTA      60
TGTCAAGATC GAGGGGAAGG ACGCTGACGA CTGGCTGTGT GTGGACTTTG GGAGTATGGT     120
GATCCATTTG ATGCTTCCAG AAACCAGAGA AACCTATGAA TTAGAGAAAC TATGGACTCT     180
ACGTTCTTTT GATGACCTTA GCTAAGCCGA ATCAGCACAC TGGCGGCGTT ACTAGTGGAT     240
CGAGCTCGTA CAGCTGATGC ATAGCTTGAG TATCTATAGG TTACTAATAG CTGGCTATCA     300
TGTCAAGCGT TC                                                         312
```

( 2 ) INFORMATION FOR SEQ ID NO:35:

( i ) SEQUENCE CHARACTERISTICS:
        ( A ) LENGTH: 281 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:35:

```
AGCTAAGGTC AAAATAAAAG CTCAAGATGA CATCAGTCCC ATTTGTCCTA AGTCCTGGTG      60
TTGTATGGAT GGTAAGCAGC AGCCAATTAT GGTGACAGGT GATAGATCCA ATTTGTTAAC     120
ATTTCTCCAT CTCTAAGCCA TCCTTAAAGA AAATCATGAA TGGAGTCACA CCATCTTCAC     180
GGTAGTCCAG GAGAGCAACC ATACCATCTG GATTCATGTT TCACCAATAA AAACTGGTAG     240
TTATTGAATT AGCAAGGATG TGCTACTCTC TGCAGCTCAG C                         281
```

( 2 ) INFORMATION FOR SEQ ID NO:36:

( i ) SEQUENCE CHARACTERISTICS:
        ( A ) LENGTH: 240 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:36:

```
AGCTAAGGTC TCATGCAATG GAACTTAATT CTTAGAACTG TAAGAATTAC ATCAAACATA      60
```

```
AAAGCCTCCC  TATTAATGTA  GTCCACAAAA  CTGGCAGGTA  TATATGCCTT  CTGAATTTGT      120

CTCCAGTGAC  TTTGGTAAAT  CTAACTAAAT  TTTAAAAAT   TCTTAATGAA  TTTATCGTCA      180

ACAACAACCA  CCTCTTGGAA  AATTAACCCT  TGCAGTGTCT  GTGTTAGACT  CAGAAGTCAA      240
```

( 2 ) INFORMATION FOR SEQ ID NO:37:

( i ) SEQUENCE CHARACTERISTICS:
        ( A ) LENGTH: 203 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:37:

```
GAATTCGGCT  TAGCTAAGGT  CAGCGTGAAG  TTTAAGCAGA  CATGAGTCTG  AAACAGTCTC       60

ATGACACATC  TGATAGGATT  TTTTAAGACT  GCCTGGCTTA  GTCTTACTGC  TGTTAGTGTA      120

TATTAGGTGT  TGTACACATT  ATAAAGAAAA  TTATGTCTCA  TTATCTTGTT  TAAGTCAAGG      180

AAAATAGAGA  ACTTTGGTCA  AAT                                                 203
```

( 2 ) INFORMATION FOR SEQ ID NO:38:

( i ) SEQUENCE CHARACTERISTICS:
        ( A ) LENGTH: 194 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:38:

```
GAATTCGGCT  TAGCTAAGGT  CAGCGTGAAG  TTTAAGCAGA  CATGAGTCTG  AAACAGTCTC       60

ATGACACATC  TGATAGGATT  TTTTAAGACT  GCCTGGCTTA  GTCTTACTGC  TGTTAGTGTA      120

TATTAGGTGT  TGTACACATT  ATAAAGAAAA  TTATGTCTCA  TTATCTTGTT  TAAGTCAAGG      180

AAAATAGAGA  ACTT                                                            194
```

( 2 ) INFORMATION FOR SEQ ID NO:39:

( i ) SEQUENCE CHARACTERISTICS:
        ( A ) LENGTH: 230 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:39:

| | | | | | |
|---|---|---|---|---|---|
| GAATTCGGCT | TAGCTAAGGT | CAAAATACAC | GGATTGCAAT | CACTTTTCTA | AACAAAAGAA | 60 |
| ACAAAGTAAC | TGCTGAGGTT | AGCAAAGATG | AGTTCTCGTC | ATACTGCCTT | GTACTGTTTT | 120 |
| GTGAACTGTG | TTATTAAAAA | TCTGAGCTTA | ACAAAATCTT | TACAAGTCAC | CTCATGAAAA | 180 |
| CAGCATTTGG | CCAATAAGAG | TTTAATTCCA | CACCAGTGAG | ACCTTAGCCT | | 230 |

( 2 ) INFORMATION FOR SEQ ID NO:40:

( i ) SEQUENCE CHARACTERISTICS:
  ( A ) LENGTH: 242 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:40:

| | | | | | |
|---|---|---|---|---|---|
| GAATTCGGCT | TTCTGCGATC | CACTCTTTGA | AGCTATTGGC | AAGATATTCA | GCAACATCCG | 60 |
| CATCAGCACG | CAGAAAGAGA | TATGAGGGAC | ATTTCAAGGA | TGAAAGGTTT | TTTTCCCCCC | 120 |
| TTACTATTTC | CTTGGTGCCA | ATTCCAAGTT | GCTCTCGCAG | CAGCAAATTT | ATGAATGGTT | 180 |
| TGTCTTGATC | AAGAACAAAG | AATTCATTCC | CACCATTCTC | ATATATACTA | CTTTCTCTTC | 240 |
| TT | | | | | | 242 |

( 2 ) INFORMATION FOR SEQ ID NO:41:

( i ) SEQUENCE CHARACTERISTICS:
  ( A ) LENGTH: 240 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:41:

| | | | | | |
|---|---|---|---|---|---|
| GAATTCGGCT | TTCTGCGATC | CACTCTTTGA | AGCTATTGGC | AAGATATTCA | GCAACATCCG | 60 |
| CATCAGCACG | CAGAAAGAGA | TATGAGGGAC | ATTTCAAGGA | TGAAAGGTTT | TTTTCCCCCC | 120 |
| TTACTATTTC | CTTGGTGCCA | ATTCCAAGTT | GCTCTCGCAG | CAGCAAATTT | ATGAATGGTT | 180 |
| TGTCTTGATC | AAGAACAAAG | AATTCATTCC | ACCATTCTCA | TATATCTACG | TCTCTTCTAG | 240 |

( 2 ) INFORMATION FOR SEQ ID NO:42:

( i ) SEQUENCE CHARACTERISTICS:
  ( A ) LENGTH: 154 base pairs
  ( B ) TYPE: nucleic acid
  ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:42:

| GAATTCGGCT | TTCTGCGATC | CTAGAGCAGG | TAAGTGAAGA | AGGCCAGTAA | GTTTTAAGGA | 60 |
| TGGCCTTGTT | GCCTTCTATC | AAGTTCTCTG | GGACTTTGTA | ATTTTGATTA | CTACTATTGA | 120 |
| TACATGGTTA | TGGTCAGAAG | GCCTCTTCTC | CCTT | | | 154 |

( 2 ) INFORMATION FOR SEQ ID NO:43:

( i ) SEQUENCE CHARACTERISTICS:
( A ) LENGTH: 270 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:43:

| AGCTAAGGTC | CGGACTCTAT | GGCATGACCC | CAAAAACATT | GGCTGGAAAG | ATTACACTGC | 60 |
| CTACAGGTGG | CACCTGATTC | ACAGGCCTAA | GACAGGCTAC | ATGAGAGTCT | TAGTGCATGA | 120 |
| AGGAAAGCAA | GTCATGGCTG | ACTCAGGACC | AATTTATGAC | CAAACCTACG | CTGGTGGACG | 180 |
| GCTGGGCTGT | TTGTCTTCTC | CAAGAGATGG | TCTATTCTCG | GACCTCAAGT | ATGAGTGCAG | 240 |
| AGATGCTAGA | GAGCAGGCTC | AGTCTCAGCA | | | | 270 |

( 2 ) INFORMATION FOR SEQ ID NO:44:

( i ) SEQUENCE CHARACTERISTICS:
( A ) LENGTH: 285 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:44:

| TGACCATCGA | GTGCATCAGC | CTCATCGGGC | TGGCCGTCGG | GAAGGAGAAA | TTCATGCAGG | 60 |
| ATGCTTCAGA | TGTGATGCAG | CTATTGTTGA | AGACACAGAC | AGACTTCAAT | GATATGGAAG | 120 |
| ATGACGACCC | CCAGATTTCT | TACATGATCT | CAGCATGGGC | CAGGATGTGC | AAAATCTTGG | 180 |
| GAAAGAATTC | CAGCAGTACC | TTCCCGTGGT | TATGGGGCCG | CTGATGAAGA | CTGCTTCAAT | 240 |

TAAGTCCTGA GTGCCTCTAG ACACCAGGAC ATGAGATATG AGGTA                          285

( 2 ) INFORMATION FOR SEQ ID NO:45:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:45:

TGACCATCGT GTAGTTGGTG TGCTTGTTGT CGAAGATGAG GGCCTCCTGG ATGAGCTGGT          60

GCTGCTGCTC CAGCAGGTCC AGGCTGGGCT TGTAGTCCAC GATGCTGCGC TCGTACTGCT          120

TCAGGTGGCT CAGCTGGTCT TCCAGAGTCC CGTTCATCTC AATGGAGATG CGCCCGATCT         180

CCTCCATCTT AGTCTGGATC CACGGCCCCA CCATATTGGC TTGGCTGGCG AACTGTCGGC         240

GAAGGCTGCA TTGGATTGCT                                                     260

( 2 ) INFORMATION FOR SEQ ID NO:46:

( i ) SEQUENCE CHARACTERISTICS:
        ( A ) LENGTH: 283 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:46:

TGACCATCGA ACACCCCAAC ACTCTCCACT ACCTGCCATT TCTTCCAGCC TTATCCACAC          60

CACCCCGTTT CTCCTGAAGA CTGATTTGCT TAGCAACTGC ACTGAGCCAA CCCTGAAGAC         120

ACATGATTAT TGGTTGGGCT CCATTAAACA ACAAGCCTAG TGCTTGGGAA GGGGGGTGGG         180

GAGGGGAAGA GACGTGAGAA GCATGTTGGC GTAGACCTTG AGGCATGGAT GAAGCATCTG        240

CCGGCCTGAC CTGGTACAGG TGGCATCTGC ACTGCAGCAA GGC                           283

( 2 ) INFORMATION FOR SEQ ID NO:47:

( i ) SEQUENCE CHARACTERISTICS:
        ( A ) LENGTH: 277 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

(v i) ORIGINAL SOURCE:

(x i) SEQUENCE DESCRIPTION: SEQ ID NO:47:

| | | | | | | |
|---|---|---|---|---|---|---|
| TGACCATCGA | AGTGCAAAGG | AAATGACTTG | ATTTCATGAA | GTATCTCCAG | AAGTAACGCT | 60 |
| TTGTTTTCTG | CATCCTGAAC | TTTATTCCCA | GTGAAGAGCT | GAAAATCTGG | ACGCTCAAAA | 120 |
| AATGGAAGCA | CTTTGGAGAG | AGCCCTTAAC | TCTATCAGGT | ACAGGAAGTA | CAAGTTCCTC | 180 |
| AGCCTTCGTG | GGCCTTCTCC | TTCAGTCAGA | ATCCATCAAA | GGTGCTGGAA | CTCTGTGACA | 240 |
| TTGTGACCCA | TTCTTTCAGC | CAGTATCTGT | AAGATAC | | | 277 |

(2) INFORMATION FOR SEQ ID NO:48:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:48:

| | | | | | | |
|---|---|---|---|---|---|---|
| GGGAACGAAT | GATCTGGAAC | TGTGGCTTGT | AGACAACCCA | AATATCTTAG | GTAGGTAAGA | 60 |
| AATTCCAGCA | TCACACTATA | TAGGAAATAC | TGTGCGAAAC | TGACAGTTAA | CTGTGCACAA | 120 |
| AGTTCAATGG | CTTCAAAATA | ATGTATAAAG | GATAAGAAGA | AACCAGTTTA | CCATTTGGT | 180 |
| ATTATTTTGG | TTGCTTTGTA | TAACTTCAAT | AATTT | | | 215 |

(2) INFORMATION FOR SEQ ID NO:49:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:49:

| | | | | | | |
|---|---|---|---|---|---|---|
| GGGAACGAAT | GATCTGGAAC | TGTGGCTTGT | AGACAACCCA | AATATCTTAG | GTAGGTAAGA | 60 |
| AATTCCAGCA | TCACACTATA | TAGGAAATAC | TGTGCGAAAC | TGACAGTTAA | CTGTGCACAA | 120 |
| AGTTCAATGG | CTTCAAAATA | ATGTATAAAG | GATAAGAAGA | AACCAGTTTA | CCATTTGGT | 180 |
| ATTATTTTGG | TTGCTTTGTA | TAACTTCAAT | AATTT | | | 215 |

(2) INFORMATION FOR SEQ ID NO:50:

(i) SEQUENCE CHARACTERISTICS:
        (A) LENGTH: 10 base pairs
        (B) TYPE: nucleic acid
        (C) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:50:

GACGTAAGCC                                                                                              10

( 2 ) INFORMATION FOR SEQ ID NO:51:

( i ) SEQUENCE CHARACTERISTICS:
        ( A ) LENGTH: 189 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:51:

CCACAAAGCA  AGCTTCTGTC  TGGAGTACAG  CTCCTGTGAC  TATGGGTACC  ACAGGGCCTT     60

TGCGTGCACT  GCACACACAC  AGGGATTGAG  TCCTGGATGT  TATGACACCT  ATGCGGCAGA    120

CATAGACTGC  CAGTGGATTG  ATATTACAGA  TGTACAACCT  GGAAACTACA  TTCTAAAGGT    180

CAGTGTAAA                                                                 189

( 2 ) INFORMATION FOR SEQ ID NO:52:

( i ) SEQUENCE CHARACTERISTICS:
        ( A ) LENGTH: 227 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:52:

CTATCAATGA  AGGGGGAGAT  CACTGGGTAA  GTTCGAATGC  CCTCAGGCAA  GGTGGCCCAG     60

CCTTCCATTA  CTGAATTCAA  AGATGGCACT  GTTACTGTAC  GTTACTCACC  CAGTGAAGCT    120

GGCCTGCATG  AAATGGACAT  TCGCTATGAC  AATATGCATA  TCCCAGGAAG  CCCTCTGCAG    180

TTCTATGTTG  ATTATGTCAA  CTGTGGCCAC  ATCACTGCTT  ATGGTCC                   227

( 2 ) INFORMATION FOR SEQ ID NO:53:

( i ) SEQUENCE CHARACTERISTICS:
        ( A ) LENGTH: 373 base pairs
        ( B ) TYPE: nucleic acid (C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:53:

| | | | | | | |
|---|---|---|---|---|---|---|
| TTAGCACCTC | GACCACGAAA | TGAGGAAGAT | GCAACAGACG | TGGTGGGCCT | GGCTCAGGCT | 60 |
| GTAAACGCTC | GGTCCCCACC | TTCAGTAAAA | CAGAACAGCT | TGGATGAAGA | CCTTATTCGG | 120 |
| AAGCTAGCTT | ATGTTGCTGC | TGGGGACCTG | GCACCCATAA | ATGCTTTCAT | TGGGGGCCTT | 180 |
| GCTGCCCAGG | AAGTCATGAA | GGCCTGCTCT | GGAAAGTTTA | TGCCCATCAT | GCAGTGGTTG | 240 |
| TACTTTGATG | CTCTTGAATG | TCTCCAGAA | CGGACAAAGA | GGCTCTGACA | GAGGAGAGTG | 300 |
| CCTCCCACGT | CAGAACCGTT | ACGATGGGCA | GGTAGCTGTA | TTGGTCAGAC | TTCAGGAGAA | 360 |
| GCTGAGAAGC | AAA | | | | | 373 |

(2) INFORMATION FOR SEQ ID NO:54:

(i) SEQUENCE CHARACTERISTICS:
(A) LENGTH: 257 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:54:

| | | | | | | |
|---|---|---|---|---|---|---|
| TTAGCACCTC | CAATGGCTGG | GTACCAGCCA | GCCGCAATGT | CCGCTCCACA | AATTTGGAGT | 60 |
| CTGTGAGGTA | CTGATTAACA | TTTTCTGCTG | GCTGCTTGAA | AAGGCCTTCA | AATTCATCCC | 120 |
| GGGCCCACTG | AAGAGTGTGT | TCGATGGCAT | TGGGAAAGTT | TTTCAGGGTA | CAAATGGGGA | 180 |
| TGGATTTCTC | TGGTGGATCC | TGGCTAGACG | TGATGGATTC | TGTCAGGAAG | GGGATTACCA | 240 |
| CCTGCACGTT | GCCCTTT | | | | | 257 |

(2) INFORMATION FOR SEQ ID NO:55:

(i) SEQUENCE CHARACTERISTICS:
(A) LENGTH: 298 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:55:

```
TTAGCACCTC ACACTCACAT GCCCTTCTAC ATAGAGACTG GTTAAACAGC CCTCCCTCCC    60

TTGTCCCGAC TTGACTTCCA GGCCCCTCTG CTTTCCTCTC ACAACCACAC CAGGTCTGAT   120

GGAGTCCAGT GCCTGCAGTG ACCCAACATA GACTGCACTT TCACCTACCT ACTGGATGGT   180

CCTGCAGCCC AGACGGCTGC TCTTCTTTCT CATGGAGTTT CTCTCCTGCC TGAGATATGC   240

TATCTGGTCT GCCCCTGTGT AGCTCCCATG GGATCCCTTA AAATCGATCC TTTTTTAA    298
```

( 2 ) INFORMATION FOR SEQ ID NO:56:

( i ) SEQUENCE CHARACTERISTICS:
        ( A ) LENGTH: 337 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:56:

```
TTAGCACCTC GTGAGGAGAC TGTTGTCCAC AGGCCAGCTA GTGGTACCCT ACTGAGAAGT    60

TGGGTTTTGG TTTTGTTTCC CTTGAAGGGT CGCTGTTAGA GGATGGAAGT AACTTCTAAT   120

TCTTGATCTG TTTGTTGGTC TTGTTTTCAG TACTTTTTGC CAGTTGTATA CACTTGGAGA   180

GGGAATTTGT ATGCCTGTAA TCTTGTTCTT GAGGTCAGAA ATTCAAAACA TTGGGAGCTT   240

TTGTTGTAAA GGTTAAACTG TGAATCCATA TAGCAAATGC AGATCCTTTT ACAGTGTAAA   300

CCACATTTCC TGCCTCAGCC TAAAGCACTG GTCATTT                            337
```

( 2 ) INFORMATION FOR SEQ ID NO:57:

( i ) SEQUENCE CHARACTERISTICS:
        ( A ) LENGTH: 333 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:57:

```
ACCTGCATGC CTAAAGGAGT AGGCTTAGGG GTGGGGAGAG AGAAGGCATA GGCTTTTCTA    60

GTTATACAAA GCTGTGTAAG GCAAGGTTCC TTTCTACTAA ATGGTCAGCT GTCACTACAT   120

TTATACTTTT GTATGTCATA AACCCTTTCT TTCATTCCTC CCTGGGTAAC CAGGACAATC   180

GGAGGGCAGT GTGTTACTGG GATTAGAGGA CTAGCAATAC TGGGTAACCC GCCTAAGCTG   240

GAAGGTGACG TAATACGTTT CTTTAAAGAT TCAGTCAGTC AAGCAGTTTA GCAATATCAA   300

AATGTCTGGC TGTTTGGTCC AGTGTACACT GTT                                333
```

( 2 ) INFORMATION FOR SEQ ID NO:58:

(i) SEQUENCE CHARACTERISTICS:
(A) LENGTH: 296 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:58:

```
GCTATCTGCG AAACTACAGA AAGGAAGACA GCTTGGCCCA GCGCGGTGAA GTTCAGAATT    60
CACTAGGTAG TTGTTGTTGG TTGACTTGGA GGTAGCTGGG TAATCAACAG CTTTCACTTT   120
AGATTCAATG TGAACCGCAG AGTTACTCAT GACCAAGAGT CTGGCAAACT CATTAATGCT   180
GTTTAATACT TGTTTGATAT TTTTCACCT TTTGAGCCCT TTTCCCAAAG AATTCAATAT    240
CAGTTTAGTA GCAACAGTAC AGTTGCCATT TAAATTGGTT TAGTTGCAGT ATAGCA       296
```

(2) INFORMATION FOR SEQ ID NO:59:

(i) SEQUENCE CHARACTERISTICS:
(A) LENGTH: 296 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:59:

```
GCTATCTGCG AAACTACAGA AAGGAAGACA GCTTGGCCCA GCGCGGTGAA GTTCAGAATT    60
CACTAGGTAG TTGTTGTTGG TTGACTTGGA GGTAGCTGGG TAATCAACAG CTTTCACTTT   120
AGATTCAATG TGAACCGCAG AGTTACTCAT GACCAAGAGT CTGGCAAACT CATTAATGCT   180
GTTTAATACT TGTTTGATAT TTTTCACCT TTTGAGCCCT TTTCCCAAAG AATTCAATAT    240
CAGTTTAGTA GCAACAGTAC AGTTGCCATT TAAATTGGTT TAGTTGCAGT ATAGCA       296
```

(2) INFORMATION FOR SEQ ID NO:60:

(i) SEQUENCE CHARACTERISTICS:
(A) LENGTH: 273 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:60:

```
GCTATACTGC AACTAAACCA ATTTAAATGG CAACTGTACT GTTGCTACTA AACTGATATT    60
GAATTCTTTG GGAAAAGGGC TCAAAAGGTG AAAAAATATC AACAAGTAT TAAACAGCAT   120
TAATGAGTTT GCCAGACTCT TGGTCATGAG TAACTCTGCG GTTCACATTG AATCTAAAGT   180
GAAAGCTGTT GATTACCCAG CTACCTCCAA GTCAACCAAC AACAACTACC TAGTGAATTC   240
TGAACTTCAC CGCGCTGGGC CAAGCTGTCT TCC                                273
```

(2) INFORMATION FOR SEQ ID NO:61:

(i) SEQUENCE CHARACTERISTICS:
        (A) LENGTH: 322 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:61:

```
GCTATACTGC CCACCACATT GCCACACTCG GAATGACATT TCTATATTTT CACCTCCCCA    60
GATTTCCATT TCTTCATCGT AACTTCCAAT GTGCTCAAAA TATTTTTTAG ATATAGAAAA   120
AAGGCCTCCT GCAAAGGTGG GGGTCTTAAT TGGGTAGGTT TCATCTTTCC TTCTTTGCTT   180
CTCATGATCA GGAAGTGACT CCCAGCCAAA GGAAAGGCTC CAGTCAAAAT TTCCACGGTT   240
ATGGTTGCTT CCGTACGGAG AAGGCTTGTT GAATTCAAAT GTGTTAGAT CTATGGATGC    300
GATGTCTGGA CTCACCACGG CA                                            322
```

(2) INFORMATION FOR SEQ ID NO:62:

(i) SEQUENCE CHARACTERISTICS:
        (A) LENGTH: 262 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:62:

```
GCTATACTGC TGAAGGAGAT CATTTGGTG GATGATGCTA GTGTAGACGA CTACCTGCAT    60
GAAAAGCTGG AGGAATACAT AAAACAGTTT TCTATTGTGA AATAGTCAG GCAGCAAGAA   120
AGGAAAGGCC TGATCACCGC GCGGTTGCTA GGGGCAGCTG TAGCAACTGC CGAGACGCTC   180
ACGTTCTTAG ATGCTCACTG TGAGTGCTTC TATGGCTGGC TGGAACCTCT GCTGGCCAGG   240
ATAGCTGAGA ACTACACTGC CG                                            262
```

(2) INFORMATION FOR SEQ ID NO:63:

(i) SEQUENCE CHARACTERISTICS:
        (A) LENGTH: 295 base pairs
        (B) TYPE: nucleic acid ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:63:

```
AGTTGCCAGG GGGCAGCTCA CGGCGCAGCT CATCCTCTGT GATGTAATTC TTATCTCCAG    60
CCAGGATCTT GAAGGAAGCC ATGACCTGAT CTGCAGTATC AGTATCTGCC GTCTCTCGGG   120
ACATAAAGTC GATGAAGGCC TGGAACGTCA CTACCCCCAA GCGGTTGGGG TCTACAATGC   180
TCATGATTCG GGCAAACTCT GCCTCTCCCA TGTTGTAACC CATGGAGATA AGGCAGGCGC   240
GGAAATCGTC TGTGTCCATC ATGCCCGTCT TCTTCCGGTC AAAGTGGTTG AAAGA        295
```

( 2 ) INFORMATION FOR SEQ ID NO:64:

( i ) SEQUENCE CHARACTERISTICS:
        ( A ) LENGTH: 287 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:64:

```
AAGCCGTGTC GCTGAACTGG GAGGACACAC TGCTCACCCT AGAAGGCTCT GGCTGACCCT    60
CCGCCCGGTT AAACAGGGAC TTTGTGGCCA TGTGCTGGCG ACACAGGTCC TGGTACTCAA   120
AAGTAGTGTC ACCATGGGCC CCCTCCGGCC CCAGCGCTGC CAGGCGTCCT TATCCCGCTG   180
TCTCGAATGA TGGCGCATAC CAAGGCCACT GAAAGCCACT AGCAGCCCAG CGACGCCTGC   240
CAGGGCCACT AGAGTAAGCA GCACTGAGCG CATGGAGAT ATGCCAT                  287
```

( 2 ) INFORMATION FOR SEQ ID NO:65:

( i ) SEQUENCE CHARACTERISTICS:
        ( A ) LENGTH: 332 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:65:

```
AAGCCGTGTC TGGACGTCCG TGTGTCCGGC TCTTGCTCAC GCAGTCATGG CCTCCGGAAC    60
GCGCAAATCG GAAAGTCGGC TCCTGACTTC ACGGCCACAG CGGTGGTGGA TGGTGCCTTC   120
```

-continued

| | | | | | |
|---|---|---|---|---|---|
| AAGGAAATCA | AGCTTTCGGA | CTACAGAGGG | AAGTACGTTG | TCCTCTTTTT | CTACCCACTG | 180 |
| GACTTCACTT | TTGTTTGCCC | CACGGAGATC | ATCGCTTTTA | GCGACCATGC | TGAGGACTTC | 240 |
| CGAAAGCTAG | GCTGCGAGGT | GCTGGGAGTG | TCTGTGGACT | CTCAGTTCAC | CCACCTGGCG | 300 |
| TGGATCAATA | CCCCACGGAA | AGAGGGAGGC | TT | | | 332 |

( 2 ) INFORMATION FOR SEQ ID NO:66:

( i ) SEQUENCE CHARACTERISTICS:
        ( A ) LENGTH: 331 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:66:

| | | | | | |
|---|---|---|---|---|---|
| AAGCCGTGTC | GGAGGGCACC | AAGGCTGTCA | CCAAGTACAC | CAGCTCCAAG | TGAGTGCTCA | 60 |
| AGACTCAGCT | CTTAACCCAA | AGGCTCTTTT | CAGAGCCACT | CAAGACTTCA | AAATTGGAGC | 120 |
| TTTAATGCTG | ACTTAGTGAC | TACCGGGAAA | ATAACTGACT | TCATCTGCAG | GATTGTGTAC | 180 |
| AAACACTTAT | GGTTAGTAA | ATCGAAAAGA | TAGACATTGC | CCATCAGTTC | TGTCTGGTCC | 240 |
| ACTTAAATAT | GCTTTTTCT | TAGAAGTTCT | AAGAACCCTG | TCAATAACCT | ATCTAGGTCC | 300 |
| AGTCCTTGAG | TTCAAAGGCC | AAATACCAAT | G | | | 331 |

( 2 ) INFORMATION FOR SEQ ID NO:67:

( i ) SEQUENCE CHARACTERISTICS:
        ( A ) LENGTH: 359 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:67:

| | | | | | |
|---|---|---|---|---|---|
| CAACGCTCAG | GATGTAAGCT | GTTTCCAGCA | CCTGGTTCAA | GCGAATGTAA | GAAATAAGAA | 60 |
| GGTGTTGAAA | GATGCCGTGA | ATAACATTAC | AGCAAAGGGG | ATCACAGATT | ACAAGAAAGG | 120 |
| CTTTAGCTTT | GCCTTCGAAC | AGCTACTTAA | TTATAATGTT | TCCAGAGCTA | ATTGCAATAA | 180 |
| GATTATCATG | TTATTCACGG | ATGGAGGAGA | AGAGAGAGCC | CAGGAGATAT | TTGCCAAATA | 240 |
| CAATAAAGAC | AAAAAAGTCC | GTGTGTTTAC | ATTTTCCGTC | GGTCAACATA | ATTATGACAG | 300 |
| AGGACCTATT | CAGTGGATGG | CTTGTGAAAT | AAAGGTTACT | ATTATGAGAT | TCCTCCATT | 359 |

( 2 ) INFORMATION FOR SEQ ID NO:68:

( i ) SEQUENCE CHARACTERISTICS:
        ( A ) LENGTH: 317 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:68:

| | | | | | | |
|---|---|---|---|---|---|---|
| TCAACGCTCA | TCACACCAAG | AATCAACTGG | TTCTTCAAGT | TTGTCTTATT | TTCAGATTGG | 60 |
| CCAGTGACGT | TGAAGACTGG | TAGAGTTCCA | GTAATGACAA | GTCCCAGTTC | CAGGGCATCC | 120 |
| AAATACACAT | TTGTCCATTG | AACTTGCTTC | GCTTTGTCAC | CAGCTAAAAC | CATTGGTCTT | 180 |
| CCCAGAACAT | CTAGATATTC | CTGAGTATTG | ATTCTTATTG | CACCAATGGA | GGGAATCTCA | 240 |
| TAATAGTAAC | CTTTATTTTC | ACAAGCCATC | CACTGAATAG | GTCTCTGTCA | TAATTATGTT | 300 |
| GACCGACGGA | AATGTAA | | | | | 317 |

( 2 ) INFORMATION FOR SEQ ID NO:69:

( i ) SEQUENCE CHARACTERISTICS:
( A ) LENGTH: 317 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:69:

| | | | | | | |
|---|---|---|---|---|---|---|
| TAACGCTCAG | GAGAAGAATA | GGAATGCAGA | GAACTCTGCC | ACAGCCCCCA | CGCTCCCGGG | 60 |
| CAGCACCTCA | GCCACCACCG | CAACCACCAC | CCTGCTGTA | GATGAAAGCA | AGCCTTGGAA | 120 |
| CCAGTATCGC | TTGCCTAAGA | CTCTTATACC | TGACTCCTAC | CGGGTGATCT | TGAGACCCTA | 180 |
| CCTCACCCCC | AACAATCAGG | GCCTGTACAT | CTTCCAAGGC | AACAGTACTG | TTCGCTTTAC | 240 |
| CTGCAACCAG | ACCACGGATG | TCATTATCAT | CCACAGCAAA | AAGCTCAACT | ACACCCTCAA | 300 |
| AGGAAACCAC | AGGGTGG | | | | | 317 |

( 2 ) INFORMATION FOR SEQ ID NO:70:

( i ) SEQUENCE CHARACTERISTICS:
( A ) LENGTH: 287 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:70:

| | | | | | |
|---|---|---|---|---|---|
| CGAGTCAGAC | GGCTTCAGCA | TCGAGACCTG | TAAGATCATG | GTGGACATGC | TGGATGAAGA | 60
| TGGGAGTGGC | AAGCTTGGCC | TGAAGGAGTT | CTACATCCTC | TGGACGAAGA | TTCAGAAATA | 120
| CCAAAAAATC | TACCGGGAAA | TCGATGTGGA | CAGGTCTGGA | ACTATGAATT | CCTACGAGAT | 180
| GCGGAAAGCA | CTGGAAGAAG | CAGGTTTCAA | GCTGCCCTGT | CAACTCCATC | AAGTCATCGT | 240
| TGCCCGGTTT | GCAGACGACG | AGCTAATCAT | CGACTTTGAC | AATTTTG | | 287

( 2 ) INFORMATION FOR SEQ ID NO:71:

( i ) SEQUENCE CHARACTERISTICS:
( A ) LENGTH: 311 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:71:

| | | | | | |
|---|---|---|---|---|---|
| CGAGTCAGAC | AACCTGTTCA | AGTGGGGTGG | GGACCATCCA | CGGAGCAGCC | GGCACCGTAT | 60
| ATGAAGACCT | GAGGTACAAA | CTCTCCCTAG | AGTTCCCCAG | CGGCTACCCT | TACAACGCAC | 120
| CCACAGTGAA | GTTCCTCACA | CCCTGCTACC | ACCCCAACGT | GGACACCCAG | GCAACATCT | 180
| GCCTGGACAT | CCTCAAGGAT | AAGTGGTCTG | CACTATATGA | TGTCAGGACT | ATCTTGCTCT | 240
| CTATCCAGAG | CCTGCTAGGA | GAACCCAACA | TCGATAGCCT | TTGAACACAC | ACGCTGCGGA | 300
| ACTCTGGAAA | A | | | | | 311

( 2 ) INFORMATION FOR SEQ ID NO:72:

( i ) SEQUENCE CHARACTERISTICS:
( A ) LENGTH: 352 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:72:

| | | | | | |
|---|---|---|---|---|---|
| TATGAGTCCG | GAGCGACGGC | TACGAGTGTG | AACTGTTCCA | GCCCCGAGCG | ACACACCAGA | 60
| AGTTATGACT | ACATGGAAGG | AGGGGATATA | AGGGTGAGAA | GACTGTTCTG | TCGCACCCAG | 120
| TGGTACCTGA | GGATTGACAA | ACGAGGCAAA | GTGAAAGGGA | CCCAGGAGAT | GAAGAACAGC | 180
| TACAACATCA | TGGAAATCAG | GACCGTGGCA | GTTGGAATTG | TGGCAATCAA | AGGGGTGGAA | 240
| AGTGAATACT | ATCTTGCCAT | GAACAAGGAA | GGGAAACTCT | ATGCAAAGAA | AGAATGCAAT | 300
| GAGGATTGCA | ACTTCAAAGA | ACTGATTCTG | GAAAACCATT | ATAACACCTA | TG | 352

( 2 ) INFORMATION FOR SEQ ID NO:73:

( i ) SEQUENCE CHARACTERISTICS:
   ( A ) LENGTH: 317 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:73:

| | | | | | | |
|---|---|---|---|---|---|---|
| TATGAGTCCG | AGGAGGAGCA | CAATGCTGGG | AGTGTGGAAA | GCCAGGTTGT | CCCCAGCACA | 60 |
| CACCGAGTGA | CCGATTCCAA | GTTCCATCCA | CTCCATGCCA | AGATGGATGT | CATCAAAAAA | 120 |
| GGCCACGCCA | GGGACAGCCA | GCGCTACAAA | GTTGACTATG | AGTCTCAAAG | CACAGACACC | 180 |
| CAGAACTTCT | CCTCCGAGTC | TAAGCGGGAG | ACAGAATACG | GTCCCTGCCG | CAGAGAAATG | 240 |
| GAGGACACAC | TGAATCATCT | GAAGTTCCTC | AATGTGCTGA | GTCCAGAGTC | TCACATCCAA | 300 |
| ACTGTGACAA | GAAGGGG | | | | | 317 |

( 2 ) INFORMATION FOR SEQ ID NO:74:

( i ) SEQUENCE CHARACTERISTICS:
   ( A ) LENGTH: 247 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:74:

| | | | | | | |
|---|---|---|---|---|---|---|
| TCGCCCGGGA | CTTCATGCGA | TTGAGAAGAT | TGTCTACCAA | ATATAGAACA | GAAAAGATTT | 60 |
| ATCCCACAGC | CACTGGAGAA | AAAGAAGAAA | ATGTTAAAAA | GAACAGATAT | AAGGACATAC | 120 |
| TGCCATTTGA | TCACAGCCGA | GTTAAGTTGA | CTTTGAAGAC | TCCATCCCAA | GATTCAGATT | 180 |
| ATATCAATGC | AAATTTTATT | AAGGGTGTGT | ATGGGCCAAA | AGCATATGTG | GCAACCCAAG | 240 |
| GGCCTTT | | | | | | 247 |

( 2 ) INFORMATION FOR SEQ ID NO:75:

( i ) SEQUENCE CHARACTERISTICS:
   ( A ) LENGTH: 256 base pairs
   ( B ) TYPE: nucleic acid
   ( C ) STRANDEDNESS: single
   ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:75:

```
TGTGGAAAGC CAGGTTGTCC CCAGCACACA CCGAGTGACC GATTCCAAGT TCCATCCACT        60
CCATGCCAAG ATGGATGTCA TCAAAAAAGG CCACGCCAGG GACAGCCAGC GCTACAAAGT       120
TGACTATGAG TCTCAAAGCA CAGACACCCA GAACTTCTCC TCCGAGTCTA AGCGGGAGAC       180
AGAATACGGT CCCTGCCGCA GAGAAATGGA GGACACACTG AATCATCTGA AGTTCCTCAA       240
TGTGCTGAGT CCAGAG                                                      256
```

( 2 ) INFORMATION FOR SEQ ID NO:76:

( i ) SEQUENCE CHARACTERISTICS:
        ( A ) LENGTH: 383 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:76:

```
TGACCATCGA AGTGCAAAGG AAATGACTTG ATTTCATGAA GTATCTCCAG AAGTAACGCT        60
TTGTTTTCTG CATCCTGAAC TTTATTCCCA GTGAAGAGCT GAAAATCTGG ACGCTCAAAA       120
AATGGAAGCA CTTTGGAGAG AGCCCTTAAC TCTATCAGGT ACAGGAAGTA CAAGTTCCTC       180
AGCCTTCGTG GGCCTTCTCC TTCAGTCAGA ATCCCATCAA AGCGCTGCTG GAACTCTGTG       240
ACATTGTGAC CCCATTTCTT TTCCAGCCAA GTATCTTGTA AAAGATACCT TGCACTCAAA       300
TGCACATTAA TGCTTGCGTG CAGGCCAGAT ATAAGTCTGT AGAATCGCTC TTTCTACACA       360
GAGGCCTTCT AGCCAGTTGT AAA                                              383
```

( 2 ) INFORMATION FOR SEQ ID NO:77:

( i ) SEQUENCE CHARACTERISTICS:
        ( A ) LENGTH: 400 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:77:

```
CTGCTTGATG CTAAGCCCGG CAGCCTGTGT TTCATCTACA GGATGCACAA CATAAAAGAA        60
AAGATCTGAT TCCCGCAGGT TCTCTTCTGA CCTACACACA CACACACTAA AATAACATTT       120
AAAAATATGT GCCAAATTAT ATTTGTTCGG GTGCCACCTT CCACCAGCTT ACCACTACGG       180
TAGAACTGTC AAATTCATCT CCCTGAATTT GTCTTAAAGG GGTGTCCATG CACAGGCCCA       240
AGAGTCACCT CCAATGAAAT AAATGTAATA CTGAAGTATG CCATGATGTT TGTTGTTTTC       300
TTTCATCGTA AGCCTGTAAG CAGGAAAAAT AGTAATAGAT AGAATAGAGA CTTACCAGTG       360
```

```
GTCGATGGCC TGGTCAGTCT GTGCGGTGAC TAGGACCAGG                    400
```

( 2 ) INFORMATION FOR SEQ ID NO:78:

( i ) SEQUENCE CHARACTERISTICS:
        ( A ) LENGTH: 343 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:78:

```
ACCTGCATGC CGAGTGTGAC GCCTTTGAGG AGAAGATCCA GGCTGCCGGA GGGATCGAAC    60
TCTTTGTCGG AGGCATTGGC CCCGATGGAC ACATTGCCTT CAATGAGCCA GGCTCCAGCC   120
TGGTGTCCAG GACCCGTGTG AAGACTCTGG TTATGGACAC CATCCTGGCC AACGCTAGGT   180
TCTTTGATGG TGATCTTGCC AAGGTGCCCA CCATGGCCCT GACAGTGGGT GTCGGCACTG   240
TCATGGATGC TAAAGAGGTG ATGATCCTCA TCACAGGCGC TCACAAGGCC TTTGCTCTGT   300
ACAAAGCCAT CGATGGAGGC GTGAACCACA TGTGGACGGT GTG                     343
```

( 2 ) INFORMATION FOR SEQ ID NO:79:

( i ) SEQUENCE CHARACTERISTICS:
        ( A ) LENGTH: 337 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:79:

```
GCTATACTGC AATGTTAGGG GAATGAACGC GTTTTCCTAC TGCACTGGGG ACTTTTAGAT    60
AGGTTAATGA AAGGCCTTTT ATTCTGTTAC TGGACACGAA AACTTTGTCT AATTTCTTAT   120
ACTCTATTGT ACGTTTACAG TCGCAGCACT AAAATGGAAG ACATCAAACA TTTTTAACAG   180
AAAAAAAAAA AGATGTAAAA ACTAACTAAG GACTATTTAT TGATAATGTT TTGCTACTCC   240
TGTCAGACAA TGGCTATAAA CTGAATTAGG CAGTCTTAAA AAAAAAAAA GAAAAAAAAG    300
AAAAAAGAAA AAAAGAAAAG AAAAGAAAAA AAACTGG                            337
```

( 2 ) INFORMATION FOR SEQ ID NO:80:

( i ) SEQUENCE CHARACTERISTICS:
        ( A ) LENGTH: 371 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:80:

| AGCTAAGGTC | GGGTACTCTG | ATACTTCAGA | GTTTAAAATC | ATCAGCCCTT | GTAGATCTAT | 60 |
| TCCTAAATCT | TATGAAAATG | CTCAGATGTT | TACACAGCTG | TGAAACAGGG | TCAGTTCAGA | 120 |
| TCGCTGATGG | CTTGAGAATG | TGTTCTTGT  | TGACATCAGG | AACTGGAAAT | GTTTACTTCC | 180 |
| CGTCATTTAT | GAGTCATCAA | GTATCTCGGC | TCTTTTAAGA | GCGCAAGATA | AAACAAGCTT | 240 |
| AAACCAGGTG | ATAAGAGCAG | AGTCCACTTG | AGTCTGAGCT | CACCCGAGAA | CTTGCTATCG | 300 |
| AGGACATTTG | GAATGGGAGT | GTGCAGGCTT | CCTTCAGTTA | CTGAATGAGT | CCATCTGCTA | 360 |
| GTCACCTTGA | C          |            |            |            |            | 371 |

(2) INFORMATION FOR SEQ ID NO:81:

(i) SEQUENCE CHARACTERISTICS:
 (A) LENGTH: 319 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:81:

| AGCTAAGGTC | CAGGGGGCAA | AGCGGTGACG | TGTGCACATC | GATATGAGAA | ACGGCAGCAC | 60 |
| GTCAACACGA | AGCAGGAGTC | GCGGGATATC | TTTGGAAGAT | GTTATGTCCT | AAGTCAGAAT | 120 |
| CTCAGAATTG | AAGATGATAT | GGACGGAGGA | GACTGGAGTT | TCTGCGATGG | CCGGTTGAGA | 180 |
| GGCCATGAAA | AGTTTGGCTC | CTGTCAGCAA | GGAGTAGCGG | CTACTTTCAC | TAAGGACTTT | 240 |
| CATTACATTG | TTTTGGAGC  | CCCAGGGACT | TACAACTGGA | AAGGGATCGT | CGTGTAGAAC | 300 |
| AAAAGAATAA | CACTTTTTT  |            |            |            |            | 319 |

(2) INFORMATION FOR SEQ ID NO:82:

(i) SEQUENCE CHARACTERISTICS:
 (A) LENGTH: 368 base pairs
 (B) TYPE: nucleic acid
 (C) STRANDEDNESS: single
 (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:82:

| AAGCCGTGTC | TGTGCTCAAG | GAAGAAACCC | ACTGGACCAA | CTTCTGTCAG | AAAGGAAAAC | 60 |

```
CTTGTTCAAA  GTTTCAGGAC  CCTGTTCTTT  GCTTATTTGC  ACATGGTCAC  CTTGGTCTGA   120

GCTAGCCACC  ATTGTCACCC  ACAGCTGCAA  AGAAAGCAGA  CCTTAGGAAA  CACTGTCACG   180

GCTGAGTGTG  ACTGCCTTGT  TCATCCCCTG  GACTGGTACT  GTGTTGCCTG  CAGTACCATT   240

GGGATCCCAT  AGCAAGAGAG  GGAGAGGGAG  ATGTTAGTTA  GCCTTTGCTA  CGAACCAAGC   300

TGTCCCAAGT  CTCAACAGCT  AAACAGGTAT  TCATTTACCA  TGATTCTATG  GTTAGCTAAG   360

CTCTTGAG                                                                  368
```

(2) INFORMATION FOR SEQ ID NO:83:

(i) SEQUENCE CHARACTERISTICS:
        (A) LENGTH: 340 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:83:

```
CTTTCTACCC  TGGAGGATGT  GCTTGAGGCA  CACTGCTCCT  GTGCTCTCCA  CTTGAGGCAT   60

AAGCCCAGTC  AGTTGTGCAT  AGATGATTAA  CCTCTGACCC  CTAAAGATGG  TAAGTTGCTC   120

TGGAGAAAGC  ATTTTAACAG  ACAAACCAGG  AGGCAAATCC  CAACTTAGAG  AGATGTTATC   180

CACTGCACAC  TGTAGAGCAA  ACTTGAGAGA  CCCAAGAGCC  TTGGTCTGCA  TCCTGTCCTT   240

GCCTGTGATA  AACACTCGAG  TACCCCCTGA  TACCGGGCGA  TATTTTGAT   TAACTGGTCG   300

AGGCTCCTTG  TCCAATTCCA  AAAGAGAACA  TCTGTGTTTC                            340
```

(2) INFORMATION FOR SEQ ID NO:84:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:84:

```
TGGTAAAGGG  CATCTGTAAA  TACACTCTAT  GAGGAAATTA  AAACTTGAAC  ATGGCAGTCT   60

GACATTGCAA  AACAAAACAA  AACAAAACTG  ACCCTCCAAT  AGCAGCGAAA  ACAACGTGAA   120

AGATACAAAG  CAATGAGAAT  CTGGTTCTGA  ACGCCTGGGA  TCCTGGGAGT  CATCGGTAGC   180

AGCGCCATGA  GAGGAGCCGT  GGCCTGTCCC  ATGTGGTCCC  ACCTTCACCT  CTTCCCTCAC   240

ATCCCTCTTA  AG                                                            252
```

(2) INFORMATION FOR SEQ ID NO:85:

(i) SEQUENCE CHARACTERISTICS:

( A ) LENGTH: 348 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:85:

| | | | | | | |
|---|---|---|---|---|---|---|
| TGGTAAAGGG | GGCAAGGGCA | AAGGCACGGG | AGACAGAGGC | CACTGCATCT | GTACCCACAT | 60 |
| CAGACATGTT | TGTCCATTTT | CTCTCATTTG | GCCTTAGACC | ATTGGCAAGA | GTAAATGCTC | 120 |
| TTAGTCCCGT | TATCTAGAAA | TTTCTTCCTT | TGGGGAGAAC | CACTTATAGA | CAATATCAGC | 180 |
| TCTCTACAAA | TAACACGAAA | GGTCGTAACA | CAGCAAGTGA | CCAGAAAGTG | CCCGTCCTTG | 240 |
| CGGCTCTGAT | CCACGTGGCT | CTCCGTAGAC | AAATTGTTTT | TTCTTGTAGG | GATATCTGTT | 300 |
| TTGCTTCTGA | ACTTTCTTAC | AAGTGTTTGG | GACTCTTCGG | GTGGCGTT | | 348 |

( 2 ) INFORMATION FOR SEQ ID NO:86:

( i ) SEQUENCE CHARACTERISTICS:
( A ) LENGTH: 351 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:86:

| | | | | | | |
|---|---|---|---|---|---|---|
| TGGTAAAGGG | TCAAGTGTTC | GATCAGAGTG | GAGCTCCATT | ACCGAATGTA | ATCGTGGAAG | 60 |
| TCCAAGACAG | AAAGCATATC | TGCCCGTTTA | GAACCAACAA | GCTTGGAGAA | TACTATCTGC | 120 |
| TTCTGCTGCC | CGGGTCCTAC | GTGATCAATG | TTACAGTCCC | TGGACACGAC | TCCTACCTCA | 180 |
| CGAAGCTTAC | TATTCCAGGG | AAATCCCAGC | CCTTCAGTGC | TCTTAAAAAG | GATTTTCACC | 240 |
| TCCCGCTGCG | ATGGCAGCCG | GATTCCATCT | CCGTATCCAA | TCCTTCGTGC | CGATGATTCC | 300 |
| GCTGTACAAA | TTCATGCCAA | GCCACTCGGC | TGCCACAAAG | CCTAGTCTGG | G | 351 |

( 2 ) INFORMATION FOR SEQ ID NO:87:

( i ) SEQUENCE CHARACTERISTICS:
( A ) LENGTH: 242 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:87:

| | | | | | |
|---|---|---|---|---|---|
| GAATTCGGCT | TTCTGCGATC | CACTCTTTGA | AGCTATTGGC | AAGATATTCA | GCAACATCCG | 60
| CATCAGCACG | CAGAAAGAGA | TATGAGGGAC | ATTTCAAGGA | TGAAAGGTTT | TTTTCCCCCC | 120
| TTACTATTTC | CTTGGTGCCA | ATTCCAAGTT | GCTCTCGCAG | CAGCAAATTT | ATGAATGGTT | 180
| TGTCTTGATC | AAGAACAAAG | AATTCATTCC | CACCATTCTC | ATATATACTA | CTTTCTCTTC | 240
| TT | | | | | | 242

( 2 ) INFORMATION FOR SEQ ID NO:88:

( i ) SEQUENCE CHARACTERISTICS:
        ( A ) LENGTH: 240 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:88:

| | | | | | |
|---|---|---|---|---|---|
| GAATTCGGCT | TTCTGCGATC | CACTCTTTGA | AGCTATTGGC | AAGATATTCA | GCAACATCCG | 60
| CATCAGCACG | CAGAAAGAGA | TATGAGGGAC | ATTTCAAGGA | TGAAAGGTTT | TTTTCCCCCC | 120
| TTACTATTTC | CTTGGTGCCA | ATTCCAAGTT | GCTCTCGCAG | CAGCAAATTT | ATGAATGGTT | 180
| TGTCTTGATC | AAGAACAAAG | AATTCATTCC | ACCATTCTCA | TATATCTACG | TCTCTTCTAG | 240

( 2 ) INFORMATION FOR SEQ ID NO:89:

( i ) SEQUENCE CHARACTERISTICS:
        ( A ) LENGTH: 687 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:89:

| | | | | | |
|---|---|---|---|---|---|
| ACGAGGGGAA | ACCTCCTCAG | AGCCTGCAGC | CAGCCACGCG | CCAGCATGTC | TGGGGGCAAA | 60
| TACGTAGACT | CCGAGGGACA | TCTCTACACT | GTTCCCATCC | GGGAACAGGG | CAACATCTAC | 120
| AAGCCCAACA | ACAAGGCCAT | GGCAGACGAG | GTGACTGAGA | AGCAAGTGTA | TGACGCGCAC | 180
| ACCAAGGAGA | TTGACCTGGT | CAACCGCGAC | CCCAAGCATC | TCAACGACGA | CGTGGTCAAG | 240
| ATTGACTTTG | AAGATGTGAT | TGCAGAACCA | GAAGGGACAC | ACAGTTTCGA | CGGCATCTGG | 300
| AAGGCCAGCT | TCACCACCTT | CACTGTGACA | AAATATTGGT | TTTACCGCTT | GTTGTCTACG | 360
| ATCTTCGGCA | TCCCAATGGC | ACTCATCTGG | GGCATTTACT | TTGCCATTCT | CTCCTTCCTG | 420
| CACATCTGGG | CGGTTGTACC | GTGCATCAAG | AGCTTCCTGA | TTGAGATTCA | GTGCATCAGC | 480
| CGCGTCTACT | CCATCTACGT | CCATACCTTC | TGCGATCCAC | TCTTTGAAGC | TATTGGCAAG | 540

ATATTCAGCA ACATCCGCAT CAGCACGCAG AAAGAGATAT GAGGGACATT TCAAGGATGA    600

AAGGTTTTTT TCCCCCCTTA CTATTTCCTT GGTGCCAATT CCAAGTTGCT CTCGCAGCAG    660

CAAATTTATG AATGGTTTGT CTTGATC                                        687

( 2 ) INFORMATION FOR SEQ ID NO:90:

( i ) SEQUENCE CHARACTERISTICS:
        ( A ) LENGTH: 560 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:90:

| Met | Glu | Cys | Leu | Tyr | Tyr | Phe | Leu | Gly | Phe | Leu | Leu | Leu | Ala | Ala | Arg |
|---|---|---|---|---|---|---|---|---|---|---|---|---|---|---|---|
| 1 | | | | 5 | | | | | 10 | | | | | 15 | |
| Leu | Pro | Leu | Asp | Ala | Ala | Lys | Arg | Phe | His | Asp | Val | Leu | Gly | Asn | Glu |
| | | | 20 | | | | 25 | | | | | 30 | | | |
| Arg | Pro | Ser | Ala | Tyr | Met | Arg | Glu | His | Asn | Gln | Leu | Asn | Gly | Trp | Ser |
| | | 35 | | | | | 40 | | | | | 45 | | | |
| Ser | Asp | Glu | Asn | Asp | Trp | Asn | Glu | Lys | Leu | Tyr | Pro | Val | Trp | Lys | Arg |
| | 50 | | | | | 55 | | | | | 60 | | | | |
| Gly | Asp | Met | Arg | Trp | Lys | Asn | Ser | Trp | Lys | Gly | Gly | Arg | Val | Gln | Ala |
| 65 | | | | | 70 | | | | | 75 | | | | | 80 |
| Val | Leu | Thr | Ser | Asp | Ser | Pro | Ala | Leu | Val | Gly | Ser | Asn | Ile | Thr | Phe |
| | | | | 85 | | | | | 90 | | | | | 95 | |
| Ala | Val | Asn | Leu | Ile | Phe | Pro | Arg | Cys | Gln | Lys | Glu | Asp | Ala | Asn | Gly |
| | | | 100 | | | | | 105 | | | | | 110 | | |
| Asn | Ile | Val | Tyr | Glu | Lys | Asn | Cys | Arg | Asn | Glu | Ala | Gly | Leu | Ser | Ala |
| | | 115 | | | | | 120 | | | | | 125 | | | |
| Asp | Pro | Tyr | Val | Tyr | Asn | Trp | Thr | Ala | Trp | Ser | Glu | Asp | Ser | Asp | Gly |
| | 130 | | | | | 135 | | | | | 140 | | | | |
| Glu | Asn | Gly | Thr | Gly | Gln | Ser | His | His | Asn | Val | Phe | Pro | Asp | Gly | Lys |
| 145 | | | | | 150 | | | | | 155 | | | | | 160 |
| Pro | Phe | Pro | His | His | Pro | Gly | Trp | Arg | Arg | Trp | Asn | Phe | Ile | Tyr | Val |
| | | | | 165 | | | | | 170 | | | | | 175 | |
| Phe | His | Thr | Leu | Gly | Gln | Tyr | Phe | Gln | Lys | Leu | Gly | Arg | Cys | Ser | Val |
| | | | 180 | | | | | 185 | | | | | 190 | | |
| Arg | Val | Ser | Val | Asn | Thr | Ala | Asn | Val | Thr | Leu | Gly | Pro | Gln | Leu | Met |
| | | 195 | | | | | 200 | | | | | 205 | | | |
| Glu | Val | Thr | Val | Tyr | Arg | Arg | His | Gly | Arg | Ala | Tyr | Val | Pro | Ile | Ala |
| | 210 | | | | | 215 | | | | | 220 | | | | |
| Gln | Val | Lys | Asp | Val | Tyr | Val | Val | Thr | Asp | Gln | Ile | Pro | Val | Phe | Val |
| 225 | | | | | 230 | | | | | 235 | | | | | 240 |
| Thr | Met | Phe | Gln | Lys | Asn | Asp | Arg | Asn | Ser | Ser | Asp | Glu | Thr | Phe | Leu |
| | | | | 245 | | | | | 250 | | | | | 255 | |
| Lys | Asp | Leu | Pro | Ile | Met | Phe | Asp | Val | Leu | Ile | His | Asp | Pro | Ser | His |
| | | | 260 | | | | | 265 | | | | | 270 | | |
| Phe | Leu | Asn | Tyr | Ser | Thr | Ile | Asn | Tyr | Lys | Trp | Ser | Phe | Gly | Asp | Asn |

|     |     |     |     |     | 275 |     |     |     |     | 280 |     |     |     |     | 285 |     |     |
|-----|-----|-----|-----|-----|-----|-----|-----|-----|-----|-----|-----|-----|-----|-----|-----|-----|-----|

Thr Gly Leu Phe Val Ser Thr Asn His Thr Val Asn His Thr Tyr Val
    290                    295              300

Leu Asn Gly Thr Phe Ser Leu Asn Leu Thr Val Lys Ala Ala Ala Pro
305                  310                 315                 320

Gly Pro Cys Pro Pro Pro Pro Pro Pro Arg Pro Ser Lys Pro Thr
               325                 330             335

Pro Ser Leu Gly Pro Ala Gly Asp Asn Pro Leu Glu Leu Ser Arg Ile
            340               345             350

Pro Asp Glu Asn Cys Gln Ile Asn Arg Tyr Gly His Phe Gln Ala Thr
          355             360               365

Ile Thr Ile Val Glu Gly Ile Leu Glu Val Asn Ile Ile Gln Met Thr
    370                 375              380

Asp Val Leu Met Pro Val Pro Trp Pro Glu Ser Ser Leu Ile Asp Phe
385                  390                 395                 400

Val Val Thr Cys Gln Gly Ser Ile Pro Thr Glu Val Cys Thr Ile Ile
               405                 410             415

Ser Asp Pro Thr Cys Glu Ile Thr Gln Asn Thr Val Cys Ser Pro Val
          420               425              430

Asp Val Asp Glu Met Cys Leu Leu Thr Val Arg Arg Thr Phe Asn Gly
         435              440             445

Ser Gly Thr Tyr Cys Val Asn Leu Thr Leu Gly Asp Asp Thr Ser Leu
    450                 455              460

Ala Leu Thr Ser Thr Leu Ile Ser Val Pro Asp Arg Asp Pro Ala Ser
465                  470                 475                 480

Pro Leu Arg Met Ala Asn Ser Ala Leu Ile Ser Val Gly Cys Leu Ala
               485                 490             495

Ile Phe Val Thr Val Ile Ser Leu Leu Val Tyr Lys Lys His Lys Glu
          500               505              510

Tyr Asn Pro Ile Glu Asn Ser Pro Gly Asn Val Val Arg Ser Lys Gly
        515                 520              525

Leu Ser Val Phe Leu Asn Arg Ala Lys Ala Val Phe Phe Pro Gly Asn
    530                 535              540

Gln Glu Lys Asp Pro Leu Leu Lys Asn Gln Glu Phe Lys Gly Val Ser
545                  550                 555                 560

( 2 ) INFORMATION FOR SEQ ID NO:91:

( i ) SEQUENCE CHARACTERISTICS:
        ( A ) LENGTH: 2669 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:91:

| CAGATGCCAG | AAGAACACTG | TTGCTCTTGG | TGGACGGGCC | CAGAGGAATT | CAGAGTTAAA | 60 |
| CCTTGAGTGC | CTGCGTCCGT | GAGAATTCAG | CATGGAATGT | CTCTACTATT | TCCTGGGATT | 120 |
| TCTGCTCCTG | GCTGCAAGAT | TGCCACTTGA | TGCCGCCAAA | CGATTTCATG | ATGTGCTGGG | 180 |

```
CAATGAAAGA CCTTCTGCTT ACATGAGGGA GCACAATCAA TTAAATGGCT GGTCTTCTGA    240
TGAAAATGAC TGGAATGAAA AACTCTACCC AGTGTGGAAG CGGGGAGACA TGAGGTGGAA    300
AAACTCCTGG AAGGGAGGCC GTGTGCAGGC GGTCCTGACC AGTGACTCAC CAGCCCTCGT    360
GGGCTCAAAT ATAACATTTG CGGTGAACCT GATATTCCCT AGATGCCAAA AGGAAGATGC    420
CAATGGCAAC ATAGTCTATG AGAAGAACTG CAGAAATGAG GCTGGTTTAT CTGCTGATCC    480
ATATGTTTAC AACTGGACAG CATGGTCAGA GGACAGTGAC GGGGAAAATG GCACCGGCCA    540
AAGCCATCAT AACGTCTTCC CTGATGGGAA ACCTTTTCCT CACCACCCCG GATGGAGAAG    600
ATGGAATTTC ATCTACGTCT TCCACACACT TGGTCAGTAT TTCCAGAAAT TGGGACGATG    660
TTCAGTGAGA GTTTCTGTGA ACACAGCCAA TGTGACACTT GGGCCTCAAC TCATGGAAGT    720
GACTGTCTAC AGAAGACATG GACGGGCATA TGTTCCCATC GCACAAGTGA AAGATGTGTA    780
CGTGGTAACA GATCAGATTC CTGTGTTTGT GACTATGTTC CAGAAGAACG ATCGAAATTC    840
ATCCGACGAA ACCTTCCTCA AAGATCTCCC CATTATGTTT GATGTCCTGA TTCATGATCC    900
TAGCCACTTC CTCAATTATT CTACCATTAA CTACAAGTGG AGCTTCGGGG ATAATACTGG    960
CCTGTTTGTT TCCACCAATC ATACTGTGAA TCACACGTAT GTGCTCAATG GAACCTTCAG   1020
CCTTAACCTC ACTGTGAAAG CTGCAGCACC AGGACCTTGT CCGCCACCGC CACCACCACC   1080
CAGACCTTCA AAACCCACCC CTTCTTTAGG ACCTGCTGGT GACAACCCCC TGGAGCTGAG   1140
TAGGATTCCT GATGAAAACT GCCAGATTAA CAGATATGGC CACTTTCAAG CCACCATCAC   1200
AATTGTAGAG GGAATCTTAG AGGTTAACAT CATCCAGATG ACAGACGTCC TGATGCCGGT   1260
GCCATGGCCT GAAAGCTCCC TAATAGACTT TGTCGTGACC TGCCAAGGGA GCATTCCCAC   1320
GGAGGTCTGT ACCATCATTT CTGACCCCAC CTGCGAGATC ACCCAGAACA CAGTCTGCAG   1380
CCCTGTGGAT GTGGATGAGA TGTGTCTGCT GACTGTGAGA CGAACCTTCA ATGGGTCTGG   1440
GACGTACTGT GTGAACCTCA CCCTGGGGGA TGACACAAGC CTGGCTCTCA CGAGCACCCT   1500
GATTTCTGTT CCTGACAGAG CCCAGCCTC GCCTTTAAGG ATGGCAAACA GTGCCCTGAT   1560
CTCCGTTGGC TGCTTGGCCA TATTTGTCAC TGTGATCTCC CTCTTGGTGT ACAAAAAACA   1620
CAAGGAATAC AACCCAATAG AAAATAGTCC TGGGAATGTG GTCAGAAGCA AAGGCCTGAG   1680
TGTCTTTCTC AACCGTGCAA AAGCCGTGTT CTTCCCGGGA AACCAGGAAA AGGATCCGCT   1740
ACTCAAAAAC CAAGAATTTA AAGGAGTTTC TTAAATTTCG ACCTTGTTTC TGAAGCTCAC   1800
TTTTCAGTGC CATTGATGTG AGATGTGCTG GAGTGGCTAT TAACCTTTTT TTCCTAAAGA   1860
TTATTGTTAA ATAGATATTG TGGTTTGGGG AAGTTGAATT TTTTATAGGT TAAATGTCAT   1920
TTTAGAGATG GGGAGAGGGA TTATACTGCA GGCAGCTTCA GCCATGTTGT GAAACTGATA   1980
AAAGCAACTT AGCAAGGCTT CTTTTCATTA TTTTTTATGT TTCACTTATA AAGTCTTAGG   2040
TAACTAGTAG GATAGAAACA CTGTGTCCCG AGAGTAAGGA GAGAAGCTAC TATTGATTAG   2100
AGCCTAACCC AGGTTAACTG CAAGAAGAGG CGGGATACTT TCAGCTTTCC ATGTAACTGT   2160
ATGCATAAAG CCAATGTAGT CCAGTTTCTA AGATCATGTT CCAAGCTAAC TGAATCCCAC   2220
TTCAATACAC ACTCATGAAC TCCTGATGGA ACAATAACAG GCCCAAGCCT GTGGTATGAT   2280
GTGCACACTT GCTAGACTCA GAAAAAATAC TACTCTCATA AATGGGTGGG AGTATTTTGG   2340
TGACAACCTA CTTTGCTTGG CTGAGTGAAG GAATGATATT CATATATTCA TTTATTCCAT   2400
GGACATTTAG TTAGTGCTTT TTATATACCA GGCATGATGC TGAGTGACAC TCTTGTGTAT   2460
ATTTCCAAAT TTTTGTATAG TCGCTGCACA TATTTGAAAT CATATATTAA GACTTTCCAA   2520
AGATGAGGTC CCTGGTTTTT CATGGCAACT TGATCAGTAA GGATTTCACC TCTGTTTGTA   2580
```

| ACTAAAACCA | TCTACTATAT | GTTAGACATG | ACATTCTTTT | TCTCTCCTTC | CTGAAAAATA | 2640 |
| AAGTGTGGGA | AGAGACAAAA | AAAAAAAA | | | | 2669 |

( 2 ) INFORMATION FOR SEQ ID NO:92:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:92:

| AAGGTGAAAG | ATGTGTATGT | GATAACAGAT | CAGATCCCTG | TATTCGTGAC | CATGTCCAG | 60 |
| AAGAATGACA | GGAACTTGTC | TGATGAGATC | TTCCTCAGAG | ACCTCCCCAT | CGTCTTCGAT | 120 |
| GTCCTCATTC | ATGATCCCAG | CCACTTCCTC | AACGACTCTG | CCATTTCCTA | CAAGTGGAAC | 180 |
| TTTGGGGACA | ACACTGGCCT | GTTTGTCTCC | AACAATCACA | CTTGAATCA | CACTTATGTG | 240 |
| CTCAATGGAA | CCTTCAACCT | TAACCTCACC | GTGCAAACTG | CAGTGCCCGG | GCCATGCCCT | 300 |
| CCCCCTTCGC | CTTCGACTCC | GCCTCCACCT | TCGTA | | | 335 |

( 2 ) INFORMATION FOR SEQ ID NO:93:

( i ) SEQUENCE CHARACTERISTICS:
        ( A ) LENGTH: 262 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:93:

| AAGGTGAAAG | ATGTGTATGT | GATAACAGAT | CAGATCCCTG | TATTCGTGAC | CATGTCCAG | 60 |
| AAGAATGACA | GGAACTTGTC | TGATGAGATC | TTCCTCAGAG | ACCTCCCCAT | CGTCTTCGAT | 120 |
| GTCCTCATTC | ATGATCCCAG | CCACTTCCTC | AACGACTCTG | CCATTTCCTA | CAAGTGGAAC | 180 |
| TTTGGGGACA | ACACTGGCCT | GTTTGTCTCC | AACAATCACA | CTTGAATCA | CACTTATGTG | 240 |
| CTCAATGGAA | CCTTCAACCT | TA | | | | 262 |

( 2 ) INFORMATION FOR SEQ ID NO:94:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:94:

| AAGGTGAAAG | ATGTGTATGT | GATAACAGAT | CAGATCCCTG | TATTCGTGAC | CATGTCCCAG | 60 |
| GAGAATGACA | GGAACTTGTC | TGATGAGATC | TTCCTCAGAG | ACCTCCCCAT | CGTCTTCGAT | 120 |
| GTCCTCATTC | ATGATCCCAG | CCACTTCCTC | AACGACTCTG | CCATTTCCTA | CAAGTGGAAC | 180 |
| TTTGGGGACA | ACACTGGCCT | GTTTGTCTCC | AACAATCACA | CTTGAATCA  | CACTTATGTG | 240 |
| CTCAATGGAA | CCTTCAACCT | TAACCTCACC | GTGCAAACTG | CAGTGCCCGG | GCCATGCCCT | 300 |
| CCCCCTTCGC | CTTCGACTCC | GCCTCCACCT | TCGTA      |            |            | 335 |

( 2 ) INFORMATION FOR SEQ ID NO:95:

( i ) SEQUENCE CHARACTERISTICS:
  ( A ) LENGTH: 190 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:95:

| TACGAAGGTG | GAGGCGGAGT | CGAAGGCGAA | GGGGGAGGGC | ATGGCCCGGG | CACTGCAGTT | 60 |
| TGCACGGTGA | GGTTAAGGTT | GAAGGTTCCA | TTGAGCACAT | AAGTGTGATT | CAAAGTGTGA | 120 |
| TTGTTGGAGA | CAAACAGGCC | AGTGTTGTCC | CCAAAGTTCC | ACTTGTAGGA | AATGGCAGAG | 180 |
| TCGTTGAGGA |            |            |            |            |            | 190 |

( 2 ) INFORMATION FOR SEQ ID NO:96:

( i ) SEQUENCE CHARACTERISTICS:
  ( A ) LENGTH: 335 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:96:

| AAGGTGAAAG | ATGTGTATGT | GATAACAGAT | CAGATCCCTG | TATTCGTGAC | CATGTCCCAG | 60 |
| AAGAATGACA | GGAACTTGTC | TGATGAGATC | TTCCTCAGAG | ACCTCCCCAT | CGTCTTCGAT | 120 |
| GTCCTCATTC | ATGATCCCAG | CCACTTCCTC | AACGACTCTG | CCATTTCCTA | CAAGTGGAAC | 180 |
| TTTGGGGACA | ACACTGGCCT | GTTTGTCTCC | AACAATCACA | CTTGAATCA  | CACTTATGTG | 240 |
| CTCAATGGAA | CCTTCAACCT | TAACCTCACC | GTGCAAACTG | CAGTGCCCGG | GCCATGCCCT | 300 |

CCCCCTTCGC CTTCGACTCC GCCTCCACCT TCGTA 335

(2) INFORMATION FOR SEQ ID NO:97:

(i) SEQUENCE CHARACTERISTICS:
        (A) LENGTH: 74 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:97:

```
Arg Arg Trp Arg Arg Ser Arg Arg Arg Gly Arg Ala Trp Gly His
 1               5                  10                  15

Cys Ser His Gly Val Lys Val Gly Ser His Ser Val Ser Val Gly
             20                  25                  30

Asp Lys Ala Ser Val Val Lys Val Val Gly Asn Gly Arg Val Val Val
             35                  40                  45

Ala Gly Met Asn Asp Asp Asp Gly Val Ser Asp Arg Val Val Gly His
     50                  55                  60

Gly His Tyr Arg Asp Cys Tyr His His His
 65                  70
```

(2) INFORMATION FOR SEQ ID NO:98:

(i) SEQUENCE CHARACTERISTICS:
        (A) LENGTH: 71 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO:98:

```
Lys Val Lys Asp Val Tyr Val Thr Asp Val Val Thr Met Ser Lys Asn
 1               5                  10                  15

Asp Arg Asn Ser Asp Arg Asp Val Asp Val His Asp Ser His Asn Asp
             20                  25                  30

Ser Ala Ser Tyr Lys Trp Asn Gly Asp Asn Thr Gly Val Ser Asn Asn
             35                  40                  45

His Thr Asn His Thr Tyr Val Asn Gly Thr Asn Asn Thr Val Thr Ala
     50                  55                  60

Val Gly Cys Ser Ser Thr Ser
 65                  70
```

(2) INFORMATION FOR SEQ ID NO:99:

(i) SEQUENCE CHARACTERISTICS:
        (A) LENGTH: 75 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:99:

| Tyr | Gly | Gly | Gly | Gly | Val | Gly | Gly | Gly | His | Gly | Gly | Thr | Ala | Val |
|---|---|---|---|---|---|---|---|---|---|---|---|---|---|---|
| 1 | | | | 5 | | | | | 10 | | | | | 15 |
| Cys | Thr | Val | Arg | Arg | Lys | Val | Ser | Thr | Val | Lys | Val | Thr | Asn | Arg | Val |
| | | | 20 | | | | | 25 | | | | | 30 | | |
| Ser | Lys | His | Met | Ala | Ser | Arg | Lys | Trp | Gly | Ser | Met | Arg | Thr | Ser | Lys |
| | | 35 | | | | | 40 | | | | | 45 | | | |
| Thr | Met | Gly | Arg | Ser | Arg | Lys | Ser | Ser | Asp | Lys | Ser | Trp | Asp | Met | Val |
| | 50 | | | | | 55 | | | | | 60 | | | | |
| Thr | Asn | Thr | Gly | Ser | Val | Thr | Tyr | Thr | Ser | Thr |
| 65 | | | | | 70 | | | | | 75 |

( 2 ) INFORMATION FOR SEQ ID NO:100:

( i ) SEQUENCE CHARACTERISTICS:
( A ) LENGTH: 376 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:100:

| Met | Cys | Tyr | Tyr | Gly | Ala | Ala | Arg | Asp | Ala | Ala | Lys | Arg | His | Asp | Val |
|---|---|---|---|---|---|---|---|---|---|---|---|---|---|---|---|
| 1 | | | | 5 | | | | | 10 | | | | | 15 | |
| Gly | Asn | Arg | Ser | Ala | Tyr | Met | Arg | His | Asn | Asn | Gly | Trp | Ser | Ser | Asp |
| | | | 20 | | | | | 25 | | | | | 30 | | |
| Asn | Asp | Trp | Asn | Lys | Tyr | Val | Trp | Lys | Arg | Gly | Asp | Met | Arg | Trp | Lys |
| | | 35 | | | | | 40 | | | | | 45 | | | |
| Asn | Ser | Trp | Lys | Gly | Gly | Arg | Val | Ala | Val | Thr | Ser | Asp | Ser | Ala | Val |
| | 50 | | | | | 55 | | | | | 60 | | | | |
| Gly | Ser | Asn | Thr | Ala | Val | Asn | Arg | Cys | Lys | Asp | Ala | Asn | Gly | Asn | Val |
| 65 | | | | | 70 | | | | 75 | | | | | | 80 |
| Tyr | Lys | Asn | Cys | Arg | Asn | Ala | Gly | Ser | Ala | Asp | Tyr | Val | Tyr | Asn | Trp |
| | | | | 85 | | | | | 90 | | | | | 95 | |
| Thr | Ala | Trp | Ser | Asp | Ser | Asp | Gly | Asn | Gly | Thr | Gly | Ser | His | His | Asn |
| | | | | 100 | | | | | 105 | | | | | 110 | |
| Val | Asp | Gly | Lys | His | His | Gly | Trp | Arg | Arg | Trp | Asn | Tyr | Val | His | Thr |
| | | | 115 | | | | | 120 | | | | | 125 | | |
| Gly | Tyr | Lys | Gly | Arg | Cys | Ser | Val | Arg | Val | Ser | Val | Asn | Thr | Ala | Asn |
| | 130 | | | | | 135 | | | | | 140 | | | | |
| Val | Thr | Gly | Met | Val | Thr | Val | Tyr | Arg | Arg | His | Gly | Arg | Ala | Tyr | Val |

-continued

```
145                          150                          155                          160
Ala  Val  Lys  Asp  Val  Tyr  Val  Val  Thr  Asp  Val  Val  Thr  Met  Lys  Asn
                    165                      170                      175
Asp  Arg  Asn  Ser  Ser  Asp  Thr  Lys  Asp  Met  Asp  Val  His  Asp  Ser  His
               180                      185                      190
Asn  Tyr  Ser  Thr  Asn  Tyr  Lys  Trp  Ser  Gly  Asp  Asn  Thr  Gly  Val  Ser
          195                      200                      205
Thr  Asn  His  Thr  Val  Asn  His  Thr  Tyr  Val  Asn  Gly  Thr  Ser  Asn  Thr
     210                      215                      220
Val  Lys  Ala  Ala  Ala  Gly  Cys  Arg  Ser  Lys  Thr  Ser  Gly  Ala  Gly  Asp
225                      230                      235                           240
Asn  Ser  Arg  Asp  Asn  Cys  Asn  Arg  Tyr  Gly  His  Ala  Thr  Thr  Val  Gly
                    245                      250                      255
Val  Asn  Met  Thr  Asp  Val  Met  Val  Trp  Ser  Ser  Asp  Val  Val  Thr  Cys
               260                      265                      270
Gly  Ser  Thr  Val  Cys  Thr  Ser  Asp  Thr  Cys  Thr  Asn  Thr  Val  Cys  Ser
          275                      280                      285
Val  Asp  Val  Asp  Met  Cys  Thr  Val  Arg  Arg  Thr  Asn  Gly  Ser  Gly  Thr
     290                      295                      300
Tyr  Cys  Val  Asn  Thr  Gly  Asp  Asp  Thr  Ser  Ala  Thr  Ser  Thr  Ser  Val
305                      310                      315                           320
Asp  Arg  Asp  Ala  Ser  Arg  Met  Ala  Asn  Ser  Ala  Ser  Val  Gly  Cys  Ala
                    325                      330                      335
Val  Thr  Val  Ser  Val  Tyr  Lys  Lys  His  Lys  Tyr  Asn  Asn  Ser  Gly  Asn
               340                      345                      350
Val  Val  Arg  Ser  Lys  Gly  Ser  Val  Asn  Arg  Ala  Lys  Ala  Val  Gly  Asn
          355                      360                      365
Lys  Asp  Lys  Asn  Lys  Gly  Val  Ser
370                      375
```

( 2 ) INFORMATION FOR SEQ ID NO:101:

( i ) SEQUENCE CHARACTERISTICS:
        ( A ) LENGTH: 2669 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:101:

```
CAGATGCCAG  AAGAACACTG  TTGCTCTTGG  TGGACGGGCC  CAGAGGAATT  CAGAGTTAAA    60
CCTTGAGTGC  CTGCGTCCGT  GAGAATTCAG  CATGGAATGT  CTCTACTATT  TCCTGGGATT   120
TCTGCTCCTG  GCTGCAAGAT  GCCACTTGA   TGCCGCCAAA  CGATTTCATG  ATGTGCTGGG   180
CAATGAAAGA  CCTTCTGCTT  ACATGAGGGA  GCACAATCAA  TTAAATGGCT  GGTCTTCTGA   240
TGAAAATGAC  TGGAATGAAA  AACTCTACCC  AGTGTGGAAG  CGGGGAGACA  TGAGGTGGAA   300
AAACTCCTGG  AAGGGAGGCC  GTGTGCAGGC  GGTCCTGACC  AGTGACTCAC  CAGCCCTCGT   360
GGGCTCAAAT  ATAACATTTG  CGGTGAACCT  GATATTCCCT  AGATGCCAAA  AGGAAGATGC   420
CAATGGCAAC  ATAGTCTATG  AGAAGAACTG  CAGAAATGAG  GCTGGTTTAT  CTGCTGATCC   480
```

```
ATATGTTTAC AACTGGACAG CATGGTCAGA GGACAGTGAC GGGGAAAATG GCACCGGCCA      540
AAGCCATCAT AACGTCTTCC CTGATGGGAA ACCTTTTCCT CACCACCCCG GATGGAGAAG      600
ATGGAATTTC ATCTACGTCT TCCACACACT TGGTCAGTAT TTCCAGAAAT TGGGACGATG      660
TTCAGTGAGA GTTTCTGTGA ACACAGCCAA TGTGACACTT GGGCCTCAAC TCATGGAAGT      720
GACTGTCTAC AGAAGACATG GACGGGCATA TGTTCCCATC GCACAAGTGA AAGATGTGTA      780
CGTGGTAACA GATCAGATTC CTGTGTTTGT GACTATGTTC CAGAAGAACG ATCGAAATTC      840
ATCCGACGAA ACCTTCCTCA AAGATCTCCC CATTATGTTT GATGTCCTGA TTCATGATCC      900
TAGCCACTTC CTCAATTATT CTACCATTAA CTACAAGTGG AGCTTCGGGG ATAATACTGG      960
CCTGTTTGTT TCCACCAATC ATACTGTGAA TCACACGTAT GTGCTCAATG GAACCTTCAG     1020
CCTTAACCTC ACTGTGAAAG CTGCAGCACC AGGACCTTGT CCGCCACCGC CACCACCACC     1080
CAGACCTTCA AAACCCACCC CTTCTTTAGG ACCTGCTGGT GACAACCCCC TGGAGCTGAG     1140
TAGGATTCCT GATGAAAACT GCCAGATTAA CAGATATGGC CACTTTCAAG CCACCATCAC     1200
AATTGTAGAG GGAATCTTAG AGGTTAACAT CATCCAGATG ACAGACGTCC TGATGCCGGT     1260
GCCATGGCCT GAAAGCTCCC TAATAGACTT TGTCGTGACC TGCCAAGGGA GCATTCCCAC     1320
GGAGGTCTGT ACCATCATTT CTGACCCCAC CTGCGAGATC ACCAGAACA CAGTCTGCAG      1380
CCCTGTGGAT GTGGATGAGA TGTGTCTGCT GACTGTGAGA CGAACCTTCA ATGGGTCTGG     1440
GACGTACTGT GTGAACCTCA CCCTGGGGGA TGACACAAGC CTGGCTCTCA CGAGCACCCT     1500
GATTTCTGTT CCTGACAGAG ACCCAGCCTC GCCTTTAAGG ATGGCAAACA GTGCCCTGAT     1560
CTCCGTTGGC TGCTTGGCCA TATTTGTCAC TGTGATCTCC CTCTTGGTGT ACAAAAAACA     1620
CAAGGAATAC AACCCAATAG AAAATAGTCC TGGGAATGTG GTCAGAAGCA AAGGCCTGAG     1680
TGTCTTTCTC AACCGTGCAA AAGCCGTGTT CTTCCCGGGA AACCAGGAAA GGATCCGCT      1740
ACTCAAAAAC CAAGAATTTA AGGAGTTTC TTAAATTTCG ACCTTGTTTC TGAAGCTCAC      1800
TTTTCAGTGC CATTGATGTG AGATGTGCTG GAGTGGCTAT TAACCTTTTT TTCCTAAAGA    1860
TTATTGTTAA ATAGATATTG TGGTTTGGGG AAGTTGAATT TTTTATAGGT TAAATGTCAT    1920
TTTAGAGATG GGGAGAGGGA TTATACTGCA GGCAGCTTCA GCCATGTTGT GAAACTGATA   1980
AAAGCAACTT AGCAAGGCTT CTTTTCATTA TTTTTTATGT TTCACTTATA AAGTCTTAGG    2040
TAACTAGTAG GATAGAAACA CTGTGTCCCG AGAGTAAGGA GAGAAGCTAC TATTGATTAG   2100
AGCCTAACCC AGGTTAACTG CAAGAAGAGG CGGGATACTT TCAGCTTTCC ATGTAACTGT    2160
ATGCATAAAG CCAATGTAGT CCAGTTTCTA AGATCATGTT CCAAGCTAAC TGAATCCCAC   2220
TTCAATACAC ACTCATGAAC TCCTGATGGA ACAATAACAG GCCCAAGCCT GTGGTATGAT   2280
GTGCACACTT GCTAGACTCA GAAAAAATAC TACTCTCATA AATGGGTGGG AGTATTTTGG   2340
TGACAACCTA CTTTGCTTGG CTGAGTGAAG GAATGATATT CATATATTCA TTTATTCCAT    2400
GGACATTTAG TTAGTGCTTT TTATATACCA GGCATGATGC TGAGTGACAC TCTTGTGTAT    2460
ATTTCCAAAT TTTTGTATAG TCGCTGCACA TATTTGAAAT CATATATTAA GACTTTCCAA   2520
AGATGAGGTC CCTGGTTTTT CATGGCAACT TGATCAGTAA GGATTTCACC TCTGTTTGTA   2580
ACTAAAACCA TCTACTATAT GTTAGACATG ACATTCTTTT TCTCTCCTTC CTGAAAAATA   2640
AAGTGTGGGA AGAGACAAAA AAAAAAAA                                       2669
```

( 2 ) INFORMATION FOR SEQ ID NO:102:

( i ) SEQUENCE CHARACTERISTICS:
        ( A ) LENGTH: 376 amino acids ( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( v i ) ORIGINAL SOURCE:

( x i ) SEQUENCE DESCRIPTION: SEQ ID NO:102:

```
Met Cys Tyr Tyr Gly Ala Ala Arg Asp Ala Ala Lys Arg His Asp Val
 1               5                  10                  15
Gly Asn Arg Ser Ala Tyr Met Arg His Asn Asn Gly Trp Ser Ser Asp
             20                  25                  30
Asn Asp Trp Asn Lys Tyr Val Trp Lys Arg Gly Asp Met Arg Trp Lys
         35                  40                  45
Asn Ser Trp Lys Gly Gly Arg Val Ala Val Thr Ser Asp Ser Ala Val
     50                  55                  60
Gly Ser Asn Thr Ala Val Asn Arg Cys Lys Asp Ala Asn Gly Asn Val
 65                  70                  75                  80
Tyr Lys Asn Cys Arg Asn Ala Gly Ser Ala Asp Tyr Val Tyr Asn Trp
                 85                  90                  95
Thr Ala Trp Ser Asp Ser Asp Gly Asn Gly Thr Gly Ser His His Asn
            100                 105                 110
Val Asp Gly Lys His His Gly Trp Arg Arg Trp Asn Tyr Val His Thr
        115                 120                 125
Gly Tyr Lys Gly Arg Cys Ser Val Arg Val Ser Val Asn Thr Ala Asn
    130                 135                 140
Val Thr Gly Met Val Thr Val Tyr Arg Arg His Gly Arg Ala Tyr Val
145                 150                 155                 160
Ala Val Lys Asp Val Tyr Val Val Thr Asp Val Val Thr Met Lys Asn
                165                 170                 175
Asp Arg Asn Ser Ser Asp Thr Lys Asp Met Asp Val His Asp Ser His
            180                 185                 190
Asn Tyr Ser Thr Asn Tyr Lys Trp Ser Gly Asp Asn Thr Gly Val Ser
        195                 200                 205
Thr Asn His Thr Val Asn His Thr Tyr Val Asn Gly Thr Ser Asn Thr
    210                 215                 220
Val Lys Ala Ala Ala Gly Cys Arg Ser Lys Thr Ser Gly Ala Gly Asp
225                 230                 235                 240
Asn Ser Arg Asp Asn Cys Asn Arg Tyr Gly His Ala Thr Thr Val Gly
                245                 250                 255
Val Asn Met Thr Asp Val Met Val Trp Ser Ser Asp Val Thr Cys
            260                 265                 270
Gly Ser Thr Val Cys Thr Ser Asp Thr Cys Thr Asn Thr Val Cys Ser
    275                 280                 285
Val Asp Val Asp Met Cys Thr Val Arg Arg Thr Asn Gly Ser Gly Thr
290                 295                 300
Tyr Cys Val Asn Thr Gly Asp Asp Thr Ser Ala Thr Ser Thr Ser Val
305                 310                 315                 320
Asp Arg Asp Ala Ser Arg Met Ala Asn Ser Ala Ser Val Gly Cys Ala
                325                 330                 335
Val Thr Val Ser Val Tyr Lys Lys His Lys Tyr Asn Asn Ser Gly Asn
```

|     |     | 340 |     |     |     |     | 345 |     |     |     |     | 350 |     |     |
| --- | --- | --- | --- | --- | --- | --- | --- | --- | --- | --- | --- | --- | --- | --- |
| Val | Val | Arg | Ser | Lys | Gly | Ser | Val | Asn | Arg | Ala | Lys | Ala | Val | Gly | Asn |
|     |     | 355 |     |     |     |     | 360 |     |     |     |     | 365 |     |     |
| Lys | Asp | Lys | Asn | Lys | Gly | Val | Ser |
|     |     | 370 |     |     |     |     | 375 |

( 2 ) INFORMATION FOR SEQ ID NO:103:

( i ) SEQUENCE CHARACTERISTICS:
        ( A ) LENGTH: 247 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:103:

```
CTGACCAGGA ACCCACTCTT CTGTGCATGT ATGTGAGCTG TGCAGAAGTA TGTGGCTGGG    60
AACTGTTGTT CTCTAAGGAT TATTGTAAAA TGTATATCGT GGCTTAGGGA GTGTGGTTAA   120
ATAGCATTTT AGAGAAGAAA AAAAAAAAA AAAAAACTCG AGAGTACTTC TAGAGCGGCC   180
GCGGCGCCAT CGATTTTCCA CCCGGGTGGG GTACCAGGTA AGTGTACCCA ATTCGCCTAT   240
AGTGAGT                                                             247
```

( 2 ) INFORMATION FOR SEQ ID NO:104:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:104:

```
AGGACAAGCC AAGGACACTC TAAGTCTTTG GCCTTCCCTC TGACCAGGAA CCCACTCTT    60
TGTGCATGTA TGTGAGCTGT GCAGAAGTAT GTGGCTGGGA ACTGTTGTTC TCTAAGGATT   120
ATTGTAAAAT GTATATCGTG GCTTAGGGAG TGTGGTTAAA TAGCATTTTA GAGAAGACAT   180
GGGAAGACTT AGTGTTTCTT CCCATCTGTA TTGTGGTTTT TACACTGTTC GTGGGGTGGA   240
CACGCTGTGT CTGAAGGGGA GGTGGGGGTC ACTGCTACTT AAGGTCCTAG GTTAACTGGG   300
GGAGATACCA CAGATGCTCA GCTTCCACA TAACATGGGC ATGAACCAGC TAATCACACT   360
GAA                                                                 363
```

( 2 ) INFORMATION FOR SEQ ID NO:105:

( i ) SEQUENCE CHARACTERISTICS:
        ( A ) LENGTH: 524 base pairs
        ( B ) TYPE: nucleic acid (C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:105:

| | | | | | | |
|---|---|---|---|---|---|---|
| GGATCCTTCT | CCTGGTCTCC | TCGGAAGAAC | GGGGCTTTCG | CGTGACTGAG | GAGAACACTC | 60 |
| AGGCCCTTGC | CCTTGACCGT | GTTCCTGGGG | CAGTTTCCTA | TTGGCTTGTA | CGCCTTGTGT | 120 |
| TTTTTGTACA | GCAAGATGG | AACCATGGTG | ACAAGCACAG | CCAGGCAGCC | GATGGAGATC | 180 |
| AGGACACCAT | TCACTGCTCT | CAGAGGGAGT | CTGGGTCTTT | GCCAGGGATA | GAGATCAGGG | 240 |
| TGCTGGTGAG | GGCCAGGCTT | CGATCATCTC | CCAGAGTGAA | ATTCACACAG | TAGGTGCCAG | 300 |
| ACCCATTGAA | GGCTCTTCTC | ACAGACAGCA | GCACAGCCCA | TCCACAGCCA | CAGGGCTGCA | 360 |
| GACCCGGTTC | TGGGCGATCT | GGCAGGTGGG | GTCGGAGATG | ATCGTACAGG | CTTCCATGGG | 420 |
| GGTGGCCCCT | TTGCAGGTCA | CAGTGAAGTC | CATCAGGGAG | TTGGCAGGCT | GCGGTGTGGG | 480 |
| CATGGGGACA | TCTGCTATCT | GCATGATGCT | GACTTCCAGG | ATCC | | 524 |

(2) INFORMATION FOR SEQ ID NO:106:

(i) SEQUENCE CHARACTERISTICS:
(A) LENGTH: 309 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:106:

| | | | | | | |
|---|---|---|---|---|---|---|
| TAGCAGATGT | CCCCATGCCC | ACACCGCAGC | CTGCCAACTC | CCTGATGGAC | TTCACTGTGA | 60 |
| CCTGCAAAGG | GGCCACCCCC | ATGGAAGCCT | GTACGATCAT | CTCCGACCCC | ACCTGCCAGA | 120 |
| TCGCCCAGAA | CCGGGTCTGC | AGCCCTGTGG | CTGTGGATGG | GCTGTGCTGC | TGTCTGTGAG | 180 |
| AAGAGCCTTC | AATGGGTCTG | GCACCTACTG | TGTGAATTTC | ACTCTGGGAG | ATGATCGAAG | 240 |
| CCTGGCCCTC | ACCAGCACCC | TGATCTCTAT | CCCTGGCAAA | GACCCAGACT | CCCTCTGAGA | 300 |
| GCAGTGAAT | | | | | | 309 |

(2) INFORMATION FOR SEQ ID NO:107:

(i) SEQUENCE CHARACTERISTICS:
(A) LENGTH: 292 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:107:

```
GGATCCTTCT CCTGGTCTCC TCGGAAGAAC GGGGCTTTCG CGTGACTGAG GAGAACACTC      60
AGGCCCTTGC CCTTGACCGT GTTCCTGGGG CAGTTTCCTA TTGGCTTGTA CGCCTTGTGT     120
TTTTTGTACA GCAAGATGGT AACCATGGTG ACAAGCACAG CCAGGCAGCC GATGGAGATC     180
AGGACACCAT TCACTGCTCT CAGAGGGAGT CTGGGTCTTT GCCAGGGATA GAGATCAGGG     240
TGCTGGTGAG GGCCAGGCTT CGATCATCTC CCAGAGTGAA ATTCACACAG TA            292
```

(2) INFORMATION FOR SEQ ID NO:108:

(i) SEQUENCE CHARACTERISTICS:
  (A) LENGTH: 263 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:108:

```
TTTTTTTTT TTTTTTTAG ACTGCCTTTT TAATGAGTAG AATATGTACA CACACGCACC      60
ATACACAAAG CCCGGGCCCA TTATAATTTT GTCAGGAGCT CAGGCATGCT CAGTGAGTTG     120
GAAGGCAGAT GAAGCATGCC TTCAGGTGGT GATTAGCTGG GTTCATGCCC ATGTTATCGT     180
GGAAAGCTGA GGCATCTGTG GTATCTCCCC CAGTTAACCT AGGACCTTAA GTAGCAGTGA     240
CCCACCTCCC TTCAGACACA GCG                                             263
```

(2) INFORMATION FOR SEQ ID NO:109:

(i) SEQUENCE CHARACTERISTICS:
  (A) LENGTH: 270 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:109:

```
GGATCCTGGA AGTCAGCATC ATGCAGATAG CAGATGTCCC CATGCCCACA CCGCAGCCTG      60
CCAACTCCCT GATGGACTTC ACTGTGACCT GCAAAGGGGC CACCCCCATG GAAGCCTGTA     120
CGATCATCTC CGACCCCACC TGCCAGATCG CCCAGAACCG GTCTGCAGC CCTGTGGCTG      180
TGGATGGGCT GTGCTGCTGT CTGTGAGAAG AGCCTTCAAT GGGTCTGGCA CCTACTGTGT     240
GAATTTCACT CTGGGAGATG ATCGAAGCCT                                       270
```

( 2 ) INFORMATION FOR SEQ ID NO:110:

( i ) SEQUENCE CHARACTERISTICS:
        ( A ) LENGTH: 239 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:110:

```
TTTTTTTTT  TTTTTTTTC  TTCTCTAAAA  TGCTATTTAA  CCACACTCCC  TAAGCCACGA   60
TATACATTTT  ACAATAATCC  TTAGAGAACA  ACAGTTCCCA  GCCACATACT  TCTGCACAGC  120
TCACATACAT  GCACAGAAGA  GTGGGTTCCT  GGTCAGAGGG  AAGGCCAAAG  ACTTAGAGTG  180
TCCTTGGCTT  GTCTGGAGCA  ATGGATCCTT  CTCCTGGTCT  CCTCGGAAGA  ACGGGCTTT   239
```

( 2 ) INFORMATION FOR SEQ ID NO:111:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:111:

```
AAACTGCAGT  GCCCGGGCCA  TGCCCTCCCC  CTTCGCCTTC  GACTCCGCCT  CCACCTTCAA   60
CTCCGCCCTC  ACCTCCGCCC  TCACCTCTGC  CCACATTATC  AACACCTAGC  CCCTCTTTAA  120
TGCCTACTGG  TTACAAATCC  ATGGAGCTGA  GTGACATTTC  CAATGAAAAC  TGCCGAATAA  180
ACAGATATGG  CTACTTCAGA  GCCACCATCA  CAATTGTAGA  GGGGATCCTG  GACGCAGCAT  240
CATGCAGATA  GCAGATGTCC  CATGCCCACA  CCGCAGCCGT  CCAACTCCTG  ATGGACTTCA  300
CTGTGACCTC  AAGGGCACCC  ATGGAAGCTG  TCAGA                               335
```

( 2 ) INFORMATION FOR SEQ ID NO:112:

( i ) SEQUENCE CHARACTERISTICS:
        ( A ) LENGTH: 217 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:112:

| | | | | | | |
|---|---|---|---|---|---|---|
| CCTCAACGAC | TCTGCCATTT | CCTACAAGTG | GAACTTTGGG | GACAACACTG | GCCTGTTTGT | 60 |
| CTCCAACAAT | CACACTTTGA | ATCACACTTA | TGTGCTCAAT | GGAACCTTCA | ACCTTAACCT | 120 |
| CACCGTGCAA | ACTGCAGTGC | CCGGGCCATG | CCCTCCCCCT | TCGCCTTCGA | CTCCGCCTCC | 180 |
| ACCTTCAACT | CCGCCCTCAC | CTCCGCCCTC | ACCTCTG | | | 217 |

( 2 ) INFORMATION FOR SEQ ID NO:113:

( i ) SEQUENCE CHARACTERISTICS:
        ( A ) LENGTH: 620 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:113:

| | | | | | | |
|---|---|---|---|---|---|---|
| CCTCAACGAC | TCTGCCATTT | CCTACAAGTG | GAACTTTGGG | GACAACACTG | GCCTGTTTGT | 60 |
| CTCCAACAAT | CACACTTTGA | ATCACACTTA | TGTGCTCAAT | GGAACCTTCA | ACCTTAACCT | 120 |
| CACCGTGCAA | ACTGCAGTGC | CCGGGCCATG | CCCTCCCCCT | TCGCCTTCGA | CTCCGCCTCC | 180 |
| ACCTTCAACT | CCGCCCTCAC | CTCCGCCCTC | ACCTCTGCCC | ACATTATCAA | CACCTAGCCC | 240 |
| CTCTTTAATG | CCTACTGGTT | ACAAATCCAT | GGAGCTGAGT | GACATTTCCA | ATGAAAACTG | 300 |
| CCGAATAAAC | AGATATGGCT | ACTTCAGAGC | CACCATCACA | ATTGTAGAGG | GGATCCTGGA | 360 |
| AGTCAGCATC | ATGCAGATAG | CAGATGTCCC | CATGCCCACA | CCGCAGCCTG | CCAACTCCCT | 420 |
| GATGGACTTC | ACTGTGACCT | GCAAAGGGGC | CACCCCCATG | GAAGCCTGTA | CGATCATCTC | 480 |
| CGACCCCACC | TGCCAGATCG | CCCAGAACCG | GGTCTGCAGC | CCTGTGGCTG | TGGATGGGCT | 540 |
| GTGCTGCTGT | CTGTGAGAAG | AGCCTTCAAT | GGGTCTGGCA | CCTACTGTGT | GAATTTCACT | 600 |
| CTGGGAGATG | ATGCAAGCCT | | | | | 620 |

( 2 ) INFORMATION FOR SEQ ID NO:114:

( i ) SEQUENCE CHARACTERISTICS:
        ( A ) LENGTH: 354 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:114:

| | | | | | | |
|---|---|---|---|---|---|---|
| GGATCCCCTC | TACAATTGTG | ATGGTGGCTC | TGAAGTAGCC | ATATCTGTTT | ATTCGGCAGT | 60 |
| TTTCATTGGA | AATGTCACTC | AGCTCCATGG | ATTTGTAACC | AGTAGGCATT | AAAGAGGGGC | 120 |
| TAGGTGTTGA | TAATGTGGGC | AGAGGTGAGG | GCGGAGGTGA | GGGCGGAGTT | GAAGGTGGAG | 180 |

| GCGGAGTCGA | AGGCGAAGGG | GGAGGGCATG | GCCCGGGCAC | TGCAGTTTGC | ACGGTGAGGT | 240 |
| TAAGGTTGAA | GGTTCCATTG | AGCACATAAG | TGTGATTCAA | AGTGTGATTG | TTGGAGACAA | 300 |
| ACAGGCCAGT | GTTGTCCCAA | AGTTCCACTT | GTAGGAATGG | CAGAGTCGTT | GAGG | 354 |

( 2 ) INFORMATION FOR SEQ ID NO:115:

( i ) SEQUENCE CHARACTERISTICS:
        ( A ) LENGTH: 473 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:115:

| CCTCAACGAC | TCTGCCATTT | CCTACAAGTG | GAACTTTGGG | GACAACACTG | GCCTGTTTGT | 60 |
| CTCCAACAAT | CACACTTTGA | ATCACACTTA | TGTGCTCAAT | GGAACCTTCA | ACCTTAACCT | 120 |
| CACCGTGCAA | ACTGCAGTGC | CCGGGCCATG | CCCTCCCCCT | TCGCCTTCGA | CTCCGCCTCC | 180 |
| ACCTTCAACT | CCGCCCTCAC | CTCCGCCCTC | ACCTCTGCCC | ACATTATCAA | CACCTAGCCC | 240 |
| CTCTTTAATG | CCTACTGGTT | ACAAATCCAT | GGAGCTGAGT | GACATTTCCA | ATGAAAACTG | 300 |
| CCGAATAAAC | AGATATGGCT | ACTTCAGAGC | CACCATCACA | ATTGTAGAGG | GGATCCTGGA | 360 |
| AGTCAGCATC | ATGCAGATAG | CAGATGTCCC | CATGCCCACA | CCGCAGCCTG | CCAACTCCCT | 420 |
| GATGGACTTC | ACTGTGACCT | GCAAAGGGGC | CACCCCCATG | GAAGCCTGTA | CGA | 473 |

( 2 ) INFORMATION FOR SEQ ID NO:116:

( i ) SEQUENCE CHARACTERISTICS:
        ( A ) LENGTH: 223 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:116:

| GAAGGTGGAG | GCGGAGTCGA | AGGCGAAGGG | GGAGGGCATG | GCCCGGGCAC | TGCAGTTTGC | 60 |
| ACGGTGAGGT | TAAGGTTGAA | GGTTCCATTG | AGCACATAAG | TGTGATTCAA | AGTGTGATTG | 120 |
| TTGGAGACAA | ACAGGCCAGT | GTTGTCCCCA | AAGTTCCACT | TGTAGGAAAT | GGCAGAGTCG | 180 |
| TTGAGGAAGT | GGCTGGGATC | ATGAATGAGG | ACATCGAAGA | CGA | | 223 |

( 2 ) INFORMATION FOR SEQ ID NO:117:

( i ) SEQUENCE CHARACTERISTICS:
        ( A ) LENGTH: 247 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:117:

| GAATTCGCAC | GAGGGGAGTC | AGAGTCAAGC | CCTGACTGGT | TGCAGGCGCT | CGGAGTCAGC | 60 |
| ATGGAAAGTC | TCTGCGGGGT | CCTGGGATTT | CTGCTGCTGG | CTGCAGGACT | GCCTCTCCAG | 120 |
| GCTGCCAAGC | GATTTCGTGA | TGTGCTGGGC | CATGAACAGT | ATCCCGATCA | CATGAGAGAG | 180 |
| CACAACCAAT | TACGTGGCTG | GTCTTCGGAT | GAAAATGAAT | GGGTTCCAAT | ATCACTTTTG | 240 |
| TGGTGAA | | | | | | 247 |

( 2 ) INFORMATION FOR SEQ ID NO:118:

( i ) SEQUENCE CHARACTERISTICS:
( A ) LENGTH: 240 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:118:

| GAATTCGGCA | CGAGGAAGGA | GGCCGTGTGC | AGGCAGTCCT | GACCAGTGAC | TCACCGGCTC | 60 |
| TGGTGGGTTC | CAATATCACT | TTTGTGGTGA | ACCTGGTGTT | CCCCAGATGC | CAGAAGGAAG | 120 |
| ATGCTAATGG | CAATATCGTC | TATGAGAAGA | ACTGCAGGAA | TGATTTGGGA | CTGACATCTG | 180 |
| ACCTGCATGT | CTACAACTGG | ACTGCAGGGG | CAGATGATGG | TGACTGGGAA | GATGGCACCT | 240 |

( 2 ) INFORMATION FOR SEQ ID NO:119:

( i ) SEQUENCE CHARACTERISTICS:
( A ) LENGTH: 260 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:119:

| GAAGGTGGAG | GCGGAGTCGA | AGGCGAAGGG | GGAGGGCATG | GCCCGGGCAC | TGCAGTTTGC | 60 |
| ACGGTGAGGT | TAAGGTTGAA | GGTTCCATTG | AGCACATAAG | TGTGATTCAA | AGTGTGATTG | 120 |
| TTGGAGACAA | ACAGGCCAGT | GTTGTCCCCA | AAGTTCCACT | TGTAGGAAAT | GGCAGAGTCG | 180 |
| TTGAGGAAGT | GGCTGGGATC | ATGAATGAGG | ACATCGAAGA | CGATGGGGAG | GTCTCTGAGG | 240 |

AAGATCTCAT CAGACAAGTT 260

( 2 ) INFORMATION FOR SEQ ID NO:120:

( i ) SEQUENCE CHARACTERISTICS:
        ( A ) LENGTH: 231 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:120:

GAATTCGGCA CGAGGTCAAG CCCTGACTGG TTGCAGGCGC TCGGAGTCAG CATGGAAAGT 60

CTCTGCGGGG TCCTGGGATT TCTGCTGCTG GCTGCAGGAC TGCCTCTCCA GGCTGCCAAG 120

CGATTTCGTG ATGTGCTGGG CCATGAACAG TATCCCGATC ACATGAGAGA GCACAACCAA 180

TTACGTGGCT GGTCTTCGGA TGAAAATGAA TGGATGAACA CCTTGTATCC A 231

( 2 ) INFORMATION FOR SEQ ID NO:121:

( i ) SEQUENCE CHARACTERISTICS:
        ( A ) LENGTH: 286 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:121:

AAGGGGGAGG GCATGGCCCG GGCACTGCAG TTTGCACGGT GAGGTTAAGG TTGAAGGTTC 60

CATTGAGCAC ATAAGTGTGA TTCAAAGTGT GATTGTTGGA GACAAACAGG CCAGTGTTGT 120

CCCCAAAGTT CCACTTGTAG GAAATGGCAG AGTCGTTGAG GAAGTGGCTG GGATCATGAA 180

TGAGGACATC GAAGACGATG GGGAGGTCTC TGAGGAAGAT CTCATCAGAC AAGTTCCTGT 240

CATTCTTCTG GGACATGGTC ACGAATACAG GGATCTGATC TGTTAT 286

( 2 ) INFORMATION FOR SEQ ID NO:122:

( i ) SEQUENCE CHARACTERISTICS:
        ( A ) LENGTH: 224 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:122:

| | | | | | | |
|---|---|---|---|---|---|---|
| GAATTCGGCA | CGAGCCGACA | CTGTGACTCC | TGGTGGATGG | GACTGGGGAG | TCAGAGTCAA | 60 |
| GCCCTGACTG | GTTGCAGGCG | CTCGGAGTCA | GCATGGAAAG | TCTCTGCGGG | GTCCTGGGAT | 120 |
| TTCTGCTGCT | GGCTGCAGGA | CTGCCTCTCC | AGGCTGCCAA | GCGATTTCGT | GATGTGCTGG | 180 |
| GCCATGAACA | GTATCCCGAT | CACATGAGAG | AGCACAACCA | ATTA | | 224 |

( 2 ) INFORMATION FOR SEQ ID NO:123:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:123:

| | | | | | | |
|---|---|---|---|---|---|---|
| AAGGTGAAAG | ATGTGTATGT | GATAACAGAT | CAGATCCCTG | TATTCGTGAC | CATGTCCCAG | 60 |
| AAGAATGACA | GGAACTTGTC | TGATGAGATC | TTCCTCAGAG | ACCTCCCCAT | CGTCTTCGAT | 120 |
| GTCCTCATTC | ATGATCCCAG | CCACTTCCTC | AACGACTCTG | CCATTTCCTA | CAAGTGGAAC | 180 |
| TTTGGGGACA | ACACTGGCCT | GTTTGTCTCC | AACAATCACA | CTTTGAATCA | CACTTATGTG | 240 |
| CTCAATGGAA | CCTTCAACCT | TAACCTCACC | GTGCAAACTG | CAGTGCCCGG | GCCATGCCCT | 300 |
| CCCCCTTCGC | CTTCGACTCC | GCCTCCACCT | TCGTA | | | 335 |

( 2 ) INFORMATION FOR SEQ ID NO:124:

( i ) SEQUENCE CHARACTERISTICS:
        ( A ) LENGTH: 266 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:124:

| | | | | | | |
|---|---|---|---|---|---|---|
| TACCATCGGA | GAAAGAAGAC | CAAGCAAGGC | TCAGGCAGCC | ACCGCCTGCT | TCGCACTGAG | 60 |
| CCTCCTGACT | CAGACTCAGA | GTCCAGCACA | GACGAAGAGG | AATTTGGAGA | ATTGGAAATC | 120 |
| GCTCTCGTTT | TGTCAAGGGA | GACTATCCCG | ATGCTGCAAG | ATCTGCTGTC | CCTCTGGCCT | 180 |
| TTGTCATCCT | CGCGCCTGCG | TTGTGGCCTC | TGTGGGCTTG | GTGTGGAGCA | AATGGCTCTC | 240 |
| AAGGAGGACT | GAGTCTCAAG | GAAATT | | | | 266 |

( 2 ) INFORMATION FOR SEQ ID NO:125:

( i ) SEQUENCE CHARACTERISTICS:

(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:125:

| | | | | | | |
|---|---|---|---|---|---|---|
| AGCTAAGGTC | AGGAGGTGTC | TGAAGAATTG | GCTGATGCAT | GGCAGGGATG | TTGTTGACCT | 60 |
| GCTTTTAGAA | CAATACTTCC | ATTTAATTAT | AGCATATCTT | ATGTGTGTAT | TAAAGCAGAG | 120 |
| CCGATCTGGT | GGGGCTCATT | AAGTAAATGT | ACTTACTGCA | AAAGGTTCAA | CTGGTGACCC | 180 |
| CAGTTTTCCC | CAGAAGCAAT | ATGATAGGAC | AGAGGCGACT | CCTGCAAGTT | GTCTCAGACT | 240 |
| TCACACATAC | ATTGTGACAT | TCTCTGAGCA | TGTGCACTGT | ACATGATATG | ACACTATCAA | 300 |

(2) INFORMATION FOR SEQ ID NO:126:

(i) SEQUENCE CHARACTERISTICS:
(A) LENGTH: 312 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:126:

| | | | | | | |
|---|---|---|---|---|---|---|
| AGCTAAGGTC | CACTACCTTG | TGAAGATGTA | TAAACACCTG | AAATGTAGAA | GCGATCCGTA | 60 |
| TGTCAAGATC | GAGGGGAAGG | ACGCTGACGA | CTGGCTGTGT | GTGGACTTTG | GGAGTATGGT | 120 |
| GATCCATTTG | ATGCTTCCAG | AAACCAGAGA | AACCTATGAA | TTAGAGAAAC | TATGGACTCT | 180 |
| ACGTTCTTTT | GATGACCTTA | GCTAAGCCGA | ATCAGCACAC | TGGCGGCGTT | ACTAGTGGAT | 240 |
| CGAGCTCGTA | CAGCTGATGC | ATAGCTTGAG | TATCTATAGG | TTACTAATAG | CTGGCTATCA | 300 |
| TGTCAAGCGT | TC | | | | | 312 |

(2) INFORMATION FOR SEQ ID NO:127:

(i) SEQUENCE CHARACTERISTICS:
(A) LENGTH: 281 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:127:

```
GCTGAGCTGC AGAGAGTAGC ACATCCTTGC TAATTCAATA ACTACCAGTT TTTATTGGTG      60

AAACATGAAT CCAGATGGTA TGGTTGCTCT CCTGGACTAC CGTGAAGATG GTGTGACTCC     120

ATTCATGATT TTCTTTAAGG ATGGCTTAGA GATGGAGAAA TGTTAACAAA TTGGATCTAT     180

CACCTGTCAC CATAATTGGC TGCTGCTTAC CATCCATACA ACACCAGGAC TTAGGACAAA     240

TGGGACTGAT GTCATCTTGA GCTTTTATTT TGACCTTAGC T                         281
```

(2) INFORMATION FOR SEQ ID NO:128:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:128:

```
AGCTAAGGTC AGAGCCAATA GTATCATGAG AACTGAAGAA GTAATAAAGC AACTTCTCCA      60

GAAATTTAAG ATTGAGAATA GCCCTCGGGA TTTCGCTCTT TACATTATTT TTGGGACAGG     120

AGAGCAGAGA AAGCTAAAGA AGACCGATGT CCACTGCTGC AGAGGTTACT ACAAGGACCA     180

TCCAAAAGCA ATGCTCGGAT CTCTCATGGA TAAAGATGCA GAAGAATCAC GAGAGATGTG     240

GCTCGTACAT TATTTCACTT TCTTCTGATC ATACTCAAGA TAGATGAGAG AGAAT          295
```

(2) INFORMATION FOR SEQ ID NO:129:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:129:

```
TTGACTTCTG AGTCTAACAC AGACACTGCA AGGGTTAATT TTCCAAGAGG TGGTTGTTGT      60

TGACGATAAA TTCATTAAGA ATTTTAAAA ATTTAGTTAG ATTACCAAA GTCACTGGAG       120

ACAAATTCAG AAGGCATATA TACCTGCCAG TTTTGTGGAC TACATTAATA GGGAGGCTTT     180

TATGTTTGAT GTAATTCTTA CAGTTCTAAG AATTAAGTTC CATTGCATGA GACCTTAGCT     240
```

(2) INFORMATION FOR SEQ ID NO:130:

(i) SEQUENCE CHARACTERISTICS:
        (A) LENGTH: 196 base pairs
        (B) TYPE: nucleic acid
        (C) STRANDEDNESS: single
        (D) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:130:

```
AAGGTGAATC CCCGACGGCT CTGGGCCCGA GGAGAAGCGT CGCCGTGGCA AATTGGCACT        60
GCAGGAGAAG CCCTCCACAG GTACTTGGAA AAACTGGTCT CTGAGGCCAA GGCCAGCTCC       120
GAGACATTCA GGACTTCTGG ATCAGCCTCC AGGGACACTG TGCAGTGAGA AGATGGCCAT       180
GAGTCCTGCC AGTGAG                                                      196
```

( 2 ) INFORMATION FOR SEQ ID NO:131:

( i ) SEQUENCE CHARACTERISTICS:
        ( A ) LENGTH: 187 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:131:

```
AATTTTTTTT TTCGACGGCC CAACGGGGGC TTGGTGGATG GAAATATGGT TTTGTGAGTT        60
ATTGCACTAC CTGGAATATC TATGCCTCTT ATTTGCGTGT ACTGTTGCTG CTGATCGTTT       120
GGTGCTGTGT GAGTGAACCT ATGGCTTAGA AAAACGACTT TGTCTTAAAC TGAGTGGGTG       180
TTCAGGG                                                                187
```

( 2 ) INFORMATION FOR SEQ ID NO:132:

( i ) SEQUENCE CHARACTERISTICS:
        ( A ) LENGTH: 197 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:132:

```
CACCTGATTT AAAGGAAAAG CATTCTGACG TAAGAAGCTG AAAGGCGGCC CTTGCGTGCT        60
TTGAACTTTC TTATACAGCA CAGTCATCTG AAGCTTCCTG TGTGACCAAG ACAAGAACGC       120
GTGCACAAGA CTGAGAAACA GCAAGAAACA ACCCGGCATT CTACTTTCTC AACACTATCA       180
TACTTTAAAC CTTTCAC                                                     197
```

( 2 ) INFORMATION FOR SEQ ID NO:133:

(i) SEQUENCE CHARACTERISTICS:
(A) LENGTH: 200 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:133:

| | | | | | | |
|---|---|---|---|---|---|---|
| CTAGCTTACG | CTAGTCCCCC | ATGCATAAAG | ACTGATCGCT | TTTCCTTAGA | AAGGTGAGAG | 60 |
| GGTTAGGACA | AGGCCGTGTG | GTAACAACAC | CCGCAGCTCG | AAAAACCAAT | GGCTTGTTAA | 120 |
| CGTGTCAGTG | AGGCACTGTA | CGGACGTCCA | TAGTCCACAT | CTTCAAATTC | CCGCAGAAGG | 180 |
| CTTCCTATTC | TTAAACTCTA | | | | | 200 |

(2) INFORMATION FOR SEQ ID NO:134:

(i) SEQUENCE CHARACTERISTICS:
(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:134:

| | | | | | | |
|---|---|---|---|---|---|---|
| CTACATTTCT | GTATCCATTC | CTCTGTTGAA | GGCTCTGGTT | CTTTCCAGCT | TCTGGCTATT | 60 |
| ATAAATAAGG | CTGCTATAAA | CACAGTGGAG | GCATGTGTCC | TTGTTATATT | TTGGAGCATC | 120 |
| TTTTGGGTAT | ATGCCCAGAA | GTGCTATAGC | TGGTTCCTCA | GGTAGTACTA | TGTCGAATTT | 180 |
| TCTGAGGAAC | TGCCAGACTG | ATTTCCAGAG | TGGTTGTACC | AGCTTGCAAT | CCCACCAGCA | 240 |
| ATAGAGGAGT | GTTCCTCTTT | CTCTATATTC | TTGCCAACAT | CTGCTGTCAC | CTGAGTGTTT | 300 |

(2) INFORMATION FOR SEQ ID NO:135:

(i) SEQUENCE CHARACTERISTICS:
(A) LENGTH: 243 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:135:

| | | | | | | |
|---|---|---|---|---|---|---|
| TGGTAAAGGG | GGAATGATGT | CGAGGCCATC | CTGGGCTGTA | GAGCCAGGCC | CTGGCTTGGG | 60 |

```
GAGTGGGCAT TGTTAACTTG TTGCTGACTT TGTGTTGACC CCTGCATCAG CAACTATTTC    120

CTTAAATCCA GGATACAACT TGTTAAGTGT GACAGCTTTC CTTACACAC CATTTTTGTG     180

GGTGTATATA TATATTTGAC TTGGGGAGAA TTATTTTTA CAAAAATACA AAATAGCTTT     240

TAA                                                                  243
```

( 2 ) INFORMATION FOR SEQ ID NO:136:

( i ) SEQUENCE CHARACTERISTICS:
        ( A ) LENGTH: 270 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:136:

```
AGCTAAGGTC CGGACTCTAT GGCATGACCC CAAAAACATT GGCTGGAAAG ATTACACTGC    60

CTACAGGTGG CACCTGATTC ACAGGCCTAA GACAGGCTAC ATGAGAGTCT TAGTGCATGA    120

AGGAAAGCAA GTCATGGCTG ACTCAGGACC AATTTATGAC CAAACCTACG CTGGTGGACG    180

GCTGGGCTGT TTGTCTTCTC CAAGAGATGG TCTATTCTCG GACCTCAAGT ATGAGTGCAG    240

AGATGCTAGA GAGCAGGCTC AGTCTCAGCA                                     270
```

( 2 ) INFORMATION FOR SEQ ID NO:137:

( i ) SEQUENCE CHARACTERISTICS:
        ( A ) LENGTH: 260 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:137:

```
TGACCTACGT GTAGTTGGTG TGCTTGTTGT CGAAGATGAG GGCCTCCTGG ATGAGCTGGT    60

GCTGCTGCTC CAGCAGGTCC AGGCTGGGCT TGTAGTCCAC GAGTCTGCGC TCGTACTGCT    120

TCAGGTGGCT CAGCTGGTCT TCCAGAGTCC CGTTCATCTC AATGGAGATG CGCCCGATCT    180

CCTCCATCTT AGTCTGGATC CACGGCCCCA CCATATTGGC TTGGCTGGCG AACTGTCGGC    240

GAAGGCTGCA TTGGATTGCT                                                260
```

( 2 ) INFORMATION FOR SEQ ID NO:138:

( i ) SEQUENCE CHARACTERISTICS:
        ( A ) LENGTH: 187 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:138:

| | | | | | |
|---|---|---|---|---|---|
| AATTTTTTT | TTCGACGGCC | CAACGGGGGC | TTGGTGGATG | GAAATATGGT | TTTGTGAGTT | 60 |
| ATTGCACTAC | CTGGAATATC | TATGCCTCTT | ATTTGCGTGT | ACTGTTGCTG | CTGATCGTTT | 120 |
| GGTGCTGTGT | GAGTGAACCT | ATGGCTTAGA | AAAACGACTT | TGTCTTAAAC | TGAGTGGGTG | 180 |
| TTCAGGG | | | | | | 187 |

(2) INFORMATION FOR SEQ ID NO:139:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:139:

| | | | | | |
|---|---|---|---|---|---|
| CACCTGATTT | AAAGGAAAAG | CATTCTGACG | TAAGAAGCTG | AAAGGCGGCC | CTTGCGTGCT | 60 |
| TTGAACTTTC | TTATACAGCA | CAGTCATCTG | AAGCTTCCTG | TGTGACCAAG | ACAAGAACGC | 120 |
| GTGCACAAGA | CTGAGAAACA | GCAAGAAACA | ACCCGGCATT | CTACTTTCTC | AACACTATCA | 180 |
| TACTTTAAAC | CTTTCAC | | | | | 197 |

(2) INFORMATION FOR SEQ ID NO:140:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (v) FRAGMENT TYPE:

(v i) ORIGINAL SOURCE:

(x i) SEQUENCE DESCRIPTION: SEQ ID NO:140:

| | | | | | |
|---|---|---|---|---|---|
| CTAGCTTACG | CTAGTCCCCC | ATGCATAAAG | ACTGATCGCT | TTTCCTTAGA | AAGGTGAGAG | 60 |
| GGTTAGGACA | AGGCCGTGTG | GTAACAACAC | CCGCAGCTCG | AAAAACCAAT | GGCTTGTTAA | 120 |
| CGTGTCAGTG | AGGCACTGTA | CGGACGTCCA | TAGTCCACAT | CTTCAAATTC | CCGCAGAAGG | 180 |
| CTTCCTATTC | TTAAACTCTA | | | | | 200 |

(2) INFORMATION FOR SEQ ID NO:141:

( i ) SEQUENCE CHARACTERISTICS:
    ( A ) LENGTH: 300 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:141:

| | | | | | |
|---|---|---|---|---|---|
| CTACATTTCT | GTATCCATTC | CTCTGTTGAA | GGCTCTGGTT | CTTTCCAGCT | TCTGGCTATT | 60 |
| ATAAATAAGG | CTGCTATAAA | CACAGTGGAG | GCATGTGTCC | TTGTTATATT | TTGGAGCATC | 120 |
| TTTTGGGTAT | ATGCCCAGAA | GTGCTATAGC | TGGTTCCTCA | GGTAGTACTA | TGTCGAATTT | 180 |
| TCTGAGGAAC | TGCCAGACTG | ATTTCCAGAG | TGGTTGTACC | AGCTTGCAAT | CCCACCAGCA | 240 |
| ATAGAGGAGT | GTTCCTCTTT | CTCTATATTC | TTGCCAACAT | CTGCTGTCAC | CTGAGTGTTT | 300 |

( 2 ) INFORMATION FOR SEQ ID NO:142:

( i ) SEQUENCE CHARACTERISTICS:
    ( A ) LENGTH: 243 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:142:

| | | | | | |
|---|---|---|---|---|---|
| TGGTAAAGGG | GGAATGATGT | CGAGGCCATC | CTGGGCTGTA | GAGCCAGGCC | CTGGCTTGGG | 60 |
| GAGTGGGCAT | TGTTAACTTG | TTGCTGACTT | TGTGTTGACC | CCTGCATCAG | CAACTATTTC | 120 |
| CTTAAATCCA | GGATACAACT | TGTTAAGTGT | GACAGCTTTC | CTTTACACAC | CATTTTGTG | 180 |
| GGTGTATATA | TATATTTGAC | TTGGGGAGAA | TTATTTTTA | CAAAAATACA | AAATAGCTTT | 240 |
| TAA | | | | | | 243 |

( 2 ) INFORMATION FOR SEQ ID NO:143:

( i ) SEQUENCE CHARACTERISTICS:
    ( A ) LENGTH: 270 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:143:

```
AGCTAAGGTC CGGACTCTAT GGCATGACCC CAAAAACATT GGCTGGAAAG ATTACACTGC    60

CTACAGGTGG CACCTGATTC ACAGGCCTAA GACAGGCTAC ATGAGAGTCT TAGTGCATGA   120

AGGAAAGCAA GTCATGGCTG ACTCAGGACC AATTTATGAC CAAACCTACG CTGGTGGACG   180

GCTGGGCTGT TTGTCTTCTC CAAGAGATGG TCTATTCTCG GACCTCAAGT ATGAGTGCAG   240

AGATGCTAGA GAGCAGGCTC AGTCTCAGCA                                    270
```

( 2 ) INFORMATION FOR SEQ ID NO:144:

( i ) SEQUENCE CHARACTERISTICS:
          ( A ) LENGTH: 260 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:144:

```
TGACCTACGT GTAGTTGGTG TGCTTGTTGT CGAAGATGAG GGCCTCCTGG ATGAGCTGGT    60

GCTGCTGCTC CAGCAGGTCC AGGCTGGGCT TGTAGTCCAC GAGTCTGCGC TCGTACTGCT   120

TCAGGTGGCT CAGCTGGTCT TCCAGAGTCC CGTTCATCTC AATGGAGATG CGCCCGATCT   180

CCTCCATCTT AGTCTGGATC CACGGCCCCA CCATATTGGC TTGGCTGGCG AACTGTCGGC   240

GAAGGCTGCA TTGGATTGCT                                               260
```

( 2 ) INFORMATION FOR SEQ ID NO:145:

( i ) SEQUENCE CHARACTERISTICS:
          ( A ) LENGTH: 255 base pairs
          ( B ) TYPE: nucleic acid
          ( C ) STRANDEDNESS: single
          ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:145:

```
TGACCATCGA TAAGTTTAAT AACTACAGAC TTTTCCCAAG ACTACAAAAG CTTCTTGAAA    60

GTGACTACTT TAGATATTAC AAGGTGAACT TGAAGAAGCC TTGTCCTTTC TGGAATGACA   120

TCAACCAGTG TGGAAGAAGA GACTGTGCCG TCAAACCCTG CCATTCTGAT GAAGTTCCTG   180

ATGGAATTAA GTCTGCCGAG CTACAAGTAT TCTGAGGAAG CCCAACCGCA TTGAAGAATG   240

TGAGCAAGCT GAGCG                                                    255
```

( 2 ) INFORMATION FOR SEQ ID NO:146:

( i ) SEQUENCE CHARACTERISTICS:
          ( A ) LENGTH: 236 base pairs
          ( B ) TYPE: nucleic acid
          ( C ) STRANDEDNESS: single ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:146:

| | | | | | |
|---|---|---|---|---|---|
| AACTCTGTGA | ACCGTGCCTT | TCTCTGTGGA | GGTGGAGGTG | TCGGTTGAAG | ACAAGCGAGG 60 |
| TCCTCCAAGG | GGCTGTGTCT | TATGTTGCCA | TCTCCCCTTG | TAGCTTGGCT | GCCCACCCTC 120 |
| CAGACTGTGC | GCCATGGCTC | CAAGGCTGTG | ACCCGCCACT | GGAGTCATGC | ACTTCCAGCG 180 |
| GCAGAAGCTG | ATGCTATAAC | TGAGTATATT | CCTCCAAACC | TGCCATCAAC | CCGAGA 236 |

( 2 ) INFORMATION FOR SEQ ID NO:147:

( i ) SEQUENCE CHARACTERISTICS:
( A ) LENGTH: 291 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:147:

| | | | | | |
|---|---|---|---|---|---|
| ACTTCTCCAG | AGAATTTAAG | ATTGAGAATA | GCCCTCGGGA | TTTCGCTCTT | TACATTATTT 60 |
| TTGGGACAGG | AGAGCAGAGA | AAGCTAAAGA | AGACCGATGT | CCCACTGCTG | CAGAGGTTAC 120 |
| TACAAGGACC | ATCCAAAAGC | AATGCTCGGA | TCTTCCTCAT | GGATAAAGAT | GCAGAAGAAA 180 |
| TCAGCAGAGA | TGTGGCTCCG | TACATTAATT | TCACTTTTCT | TTCTTGGATC | CATCCTTCAA 240 |
| GATTAGATGA | AGAAGAGAAA | TGGAGATTGA | GAGAATATGC | AATCATACCG | A 291 |

( 2 ) INFORMATION FOR SEQ ID NO:148:

( i ) SEQUENCE CHARACTERISTICS:
( A ) LENGTH: 255 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:148:

| | | | | | |
|---|---|---|---|---|---|
| AGGGTTACTT | CAGGCTAAGG | CAATAGAAAT | CCATTTTAAG | ATGGTGTGCT | AAAGGCTTGA 60 |
| TGGATGTTCA | TCGTCTGTCT | AAAGGAGAAT | GAAGTCATCA | ACAGGATGTC | AGGGGAAAGT 120 |
| GAGATCATCG | CAGAAAGTAT | CAACTTAGCA | CAAACACACA | GGCATAGCTC | CTGCAAGAGG 180 |

```
TGAATGCTGT CCCCAAATAC CTGAGGAACT ATCCCTTTGG GCAAGAAAAT AGACAAGTCC    240

ATGAAGTCTG GGTGA                                                    255
```

( 2 ) INFORMATION FOR SEQ ID NO:149:

( i ) SEQUENCE CHARACTERISTICS:
        ( A ) LENGTH: 284 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:149:

```
GACCAGGTAC ACTTGAGCAA AGCACCCAGT ATTTAATTCC TTACAGAAAG GAGAGGAAAG    60

GTCTGCAGTT GGACTGATGG TATGCTAACA CCGCAAATGA CTGTCATTTG ATCTCAGAAG   120

TTCAGGATTG ATTGCTATGT TTTAGCTCTA ATTGTGAGAA ACAGTAGTCA TTTTAGTCTT   180

AAATTTTGCC CTCAGGAAAT TCAGGGAGAC TGAGCCTTCC TTCCCCACC TTCGTAAAGC   240

CGAATTCCAG CACACGGCGG CCGTTACTAG TGGATCCGAG CTCG                   284
```

( 2 ) INFORMATION FOR SEQ ID NO:150:

( i ) SEQUENCE CHARACTERISTICS:
        ( A ) LENGTH: 335 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:150:

```
TACAAGGTGG GATGGCAGGA ACTGAAGGCT TCTGTAAATC CAGTTTTGGC TCTCTCTCTG    60

GTCTTTCTTT CTCTTCTGTT CTGTTTGGAA GGGTTTCTGG TCTTTCAGGA GGTATTTTTT   120

TAATTTCATG TTTTCTCTCT GTGGTACCTG CCCCTTGTTT GACGACAGGA GCTGATGGAG   180

GTGGCGGTTT CTTGGGTCTA TTCCCTTCCT TGTCAAAGTC CGATGGAAGT AACTTCACGA   240

AGTTGTCAGG AAACACGCCT CGTCTGCCAT TGAGTTCTCC TTCCCACCAG CCTACGCGAT   300

GCAGTCTTAT TGATGAGAGT CACTATATCT CCTTA                              335
```

( 2 ) INFORMATION FOR SEQ ID NO:151:

( i ) SEQUENCE CHARACTERISTICS:
        ( A ) LENGTH: 254 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:151:

| TCACCCATGA | CTTCTATGGA | CTTGTCTATT | TTCTTGCCCA | AAGGGATAGT | TCCTCAGGTA | 60 |
| TTTGGGGACA | GCATTCACCT | CTTGCAGGAG | CTATGCCTGT | GTGTTTGTGC | TAAGTTGATA | 120 |
| CTTTCTGCGA | TGATCTCACT | TTCCCCTGAC | ATCCTGTTGA | TGACTTCATT | CTCCTTTAGA | 180 |
| CAGACGATGA | ACATCCATCA | GGCCTTTATG | CACACCATCT | TAAAATGGAT | TTCTATTGCC | 240 |
| TTAGCCTGAA | GTCC | | | | | 254 |

( 2 ) INFORMATION FOR SEQ ID NO:152:

( i ) SEQUENCE CHARACTERISTICS:
        ( A ) LENGTH: 241 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:152:

| CCCATAGAGA | TAGGTTTGCT | CCAGAACCTG | CAGCATTTGC | ACATCACAGG | GAACAAGGTG | 60 |
| GACATTCTGC | CAAAACAGTT | GTTTAAGTGC | GTGAAGTTGA | GGACTTTGAA | CCTGGGGCAG | 120 |
| AACTGTATCG | CCTCCCTGCC | TGAGAAAATC | AGTCAGCTCA | CCCAGCTCAC | TCAGCTGGAG | 180 |
| CTGAAGGGCA | ACTGCCTAGA | CCGCCTGCCA | GCCCAGCTGG | CAGTGTCGAT | GCTCAAGAAG | 240 |
| A | | | | | | 241 |

( 2 ) INFORMATION FOR SEQ ID NO:153:

( i ) SEQUENCE CHARACTERISTICS:
        ( A ) LENGTH: 256 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:153:

| CAATAATCCA | GGTAAAATAG | AGTAAAATAG | TCTGCTAGCA | GCAAGTTCCT | ACCATACTTT | 60 |
| CAACAACACT | CACGAGATAC | GGAATGATTA | CAGCATTAAG | AATATTTCAG | AAATGACAGG | 120 |
| TAGGTGTGGT | GGACAGGTGG | CTCACATTCA | AGACTCAAGT | CTACTTAAAA | AAGAAAATCT | 180 |
| CACTAGCACT | AGATTCTAGC | TCCTTTGTTT | CCCCCTTTCT | TTTGGTTTCA | AAGGCGTTTC | 240 |
| TACAACCCAT | AAGAGG | | | | | 256 |

( 2 ) INFORMATION FOR SEQ ID NO:154:

( i ) SEQUENCE CHARACTERISTICS:
        ( A ) LENGTH: 404 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:154:

```
GCCAAGCTAT TATGACACTA TAGATACTCA ACGTATCGAT CAACGTTGGT ACCGAGCTCG    60
GATCCACTAG TAACGGCCGC CAGTGTGCTG GAATTCGGCT TGGATTGGTC AGAGCAGTGT   120
GCAATATGAT CCAACTAAGT CTCCTCCCTT GGCCCCTCCC CAAAATGTTT GCAGTGTTAT   180
TTTTGTGGGT TTTTTTTTAA CACCCTGACA CCTGTTGTGG ACATTGTCAA CCTTTGTAAG   240
AAACCCAAA  TAAAAATTGA  AAAATAAAAT  AAAAAGAAAC  CCATGAACAT  TCGCACCACT  300
TGTGGCTTCT GACTATCTTC CACAGAGGGA AGTTTAAAAC CCAAACTTCC AAAGGTTTGA   360
ACTACCTCAA GACACTTTCG CAGTGGAGTC GTAGACCAAT CCCA                    404
```

( 2 ) INFORMATION FOR SEQ ID NO:155:

( i ) SEQUENCE CHARACTERISTICS:
        ( A ) LENGTH: 167 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:155:

```
TAAATAAATT AAAAAACTAT TAAACCTAAA AACGTCCACC AAACCCTAAA ACCATTAAAC    60
AACCAACAAA CCCACTAACA ATTAAACCTA AACCTCCATA AATAGGTGAA GGCTTTAATG   120
CTAACCCAAG ACAACCAACC AAAAATAATG AACTTAAAAC AAAAATA                 167
```

( 2 ) INFORMATION FOR SEQ ID NO:156:

( i ) SEQUENCE CHARACTERISTICS:
        ( A ) LENGTH: 212 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:156:

| | | | | | |
|---|---|---|---|---|---|
| GGTAAAGGGG | ACCTGGAGAA | CGCCTTCCTG | AACCTGGTCC | AGTGCATCCA | GAACAAGCCC | 60
| CTGTACTTCG | CTGACCGGCT | GTACGACTCC | ATGAAGGGCA | AGGGGACTCG | AGACAAGGTC | 120
| TGATTAGAAT | CATGGTCTCT | CGCAGTGAAG | TGGACATGCT | GAAAATCAGA | TCTGAATTCA | 180
| AGAGGAATAT | GGCAAGTCCT | GTACTACTAC | AT | | | 212

( 2 ) INFORMATION FOR SEQ ID NO:157:

( i ) SEQUENCE CHARACTERISTICS:
        ( A ) LENGTH: 214 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:157:

| | | | | | |
|---|---|---|---|---|---|
| AGAGCAGCAG | GCCAGCTGTA | CTTGGTTTGG | CAAGAAAAAG | AAGCAGTACA | AAGATAAATA | 60
| TTTGGCAAAG | CACAACGCAG | TGTTTGATCA | ATTAGATCTT | GTCACATATG | AAGAAGTAGT | 120
| CAAACTGCCA | GCATTCAAAA | GGAAAACATT | AGTCTTATTA | GGTGCACATG | GTGTTGGAAG | 180
| AAGACACATA | AAAAATACCC | TCATCACAAA | GCAC | | | 214

( 2 ) INFORMATION FOR SEQ ID NO:158:

( i ) SEQUENCE CHARACTERISTICS:
        ( A ) LENGTH: 342 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:158:

| | | | | | |
|---|---|---|---|---|---|
| TCGGTCATAG | TAGTAAGGGA | AATCTCCCAG | GTAAGATGAA | TACTGCGGTA | GGACGAACAA | 60
| TCCTCCAGGA | TGTTTGTTCC | ATATTAAACT | GTTACGTGAT | ATGTGCTTGA | ATATTCTGTC | 120
| CTGAATAATC | TCTAGTGTAG | TTAATACAAT | CTTCTCAACT | GAAGAAAAT | AAGCCTCCCA | 180
| CAAGAACTGT | GTCTGCTGTC | TAAGTGCTAG | GATTTATCC | TGATGAATAG | ACCTGATTGT | 240
| AGAAGGAATC | TGTAATAGCA | ATCTCTCATC | GCCTATGACC | GAAAGCCGAA | TTCTGCAGAT | 300
| ATCCATCACA | CTGGCCGGCC | GCTCGAGCAT | CGATCTAGAG | GG | | 342

( 2 ) INFORMATION FOR SEQ ID NO:159:

( i ) SEQUENCE CHARACTERISTICS:
        ( A ) LENGTH: 303 base pairs
        ( B ) TYPE: nucleic acid ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:159:

| | | | | | | |
|---|---|---|---|---|---|---|
| CTGCTTGATG | ACAAAGGGTG | TAGTCTTCAT | CTTTTCCTGG | ATTATTTTGG | AAGTGACAGG | 60 |
| TGGAAATTCC | ATCGTCACGT | TTATGTGGTC | TGTAAAGCCA | ACGATCTCAA | ATTCTGGCGG | 120 |
| CTCAAGAGGA | GCGTTTGCAG | GCACGATGTA | GTCTGAGCAG | CGGCACACGG | TCAAGTCCCC | 180 |
| TCTGTGCACT | ATGACGATGG | CGACGACGTA | GCTCTCCATG | CCCTCCAACC | ACTTATCTGT | 240 |
| CACGTCACAT | GATGACTTCG | TGGTATCTGA | ACAGTTCTTA | ACCTTCGTCA | GATTTCGTC | 300 |
| TTT | | | | | | 303 |

( 2 ) INFORMATION FOR SEQ ID NO:160:

( i ) SEQUENCE CHARACTERISTICS:
        ( A ) LENGTH: 345 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:160:

| | | | | | | |
|---|---|---|---|---|---|---|
| AAATCGTTGC | TTCAGAAAGA | CTCAATAACA | CTTACTTGTG | CCTGGCTGTG | CTGACAGTAC | 60 |
| ATTCTGTGTC | ATTTTCCTTC | ATGGGCGGAA | CAGTCCACAG | AGCTCACCAA | CAAGTACTCC | 120 |
| AAAACTGAGC | AAGAGTTTAA | GCTTCGAGAT | GCAACCAGAT | GAGCTTCTAG | AAAAGCCCAT | 180 |
| GTCTCCCATG | CAGTACGCAC | GGTCTGGACT | AGGGACAGCA | GAGATGAATG | GCAAACTCAT | 240 |
| AGCTGCAGGT | GGTTATAACA | GAGAGGAATG | TCTTCGAACA | GTTGAATGCT | ATGATCCACA | 300 |
| TACAGATCAC | TGGTCCTTCC | TTGCTCCCAT | GAGAACATCA | AGCAG | | 345 |

( 2 ) INFORMATION FOR SEQ ID NO:161:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:161:

```
CTTTCCGAAG  AGCACACCCT  CCTCTCAATG  AGCTTGTGAG  GTCTCTTTCT  TCTCTTCCTT    60

CCAACGTGGT  GCTAGCTCCA  GGCGAGCGAC  GTGAGAGTGC  CACCTGAGAC  AGACACCTTG   120

GTCTCAGTTA  GAAGGAAGAT  GCAGGTCTAA  GAGGAATCCC  CGCAGGTCTG  TCTGAGCTGT   180

GATCAAGAAT  ATTCCGCAAT  GTGCCTTTTC  TGAGATCGTG  TTAGCTCCAA  AGCTTTTTCC   240

TATCGCAGAG  TGTTCAGTTT  GTGTTTGTTT  GTTTTGTTT   TGTTTGTTT   TTCCCTTGGC   300

GGATTTCCCG  TGTGT                                                        315
```

( 2 ) INFORMATION FOR SEQ ID NO:162:

( i ) SEQUENCE CHARACTERISTICS:
    ( A ) LENGTH: 243 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:162:

```
CCTATTGAAC  GGTCTTGCAA  TGACGAGCAT  TCAGATGCTT  AAGGAAAGCA  TTGCTGCTAC    60

AAATATTTCT  ATTTTAGAA   AGGGTTTTTA  TGGACCAATG  CCCCAGTTGT  CAGTCAAAGC   120

CGTTGGTGTT  TTCATTGTTT  AAAATGTCAC  CTATAAAACG  GGCATTATTT  ATGTTTTTT    180

TCCCTTTGTT  CATATTCTTT  TGCATTCCTG  ATTATTGTAT  GTATCGTGTA  AAGGAAGTCT   240

GTA                                                                      243
```

( 2 ) INFORMATION FOR SEQ ID NO:163:

( i ) SEQUENCE CHARACTERISTICS:
    ( A ) LENGTH: 243 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:163:

```
CCTATTGAAC  GGTCTTGCAA  TGACGAGCAT  TCAGATGCTT  AAGGAAAGCA  TTGCTGCTAC    60

AAATATTTCT  ATTTTAGAA   AGGGTTTTTA  TGGACCAATG  CCCCAGTTGT  CAGTCAAAGC   120

CGTTGGTGTT  TTCATTGTTT  AAAATGTCAC  CTATAAAACG  GGCATTATTT  ATGTTTTTT    180

TCCCTTTGTT  CATATTCTTT  TGCATTCCTG  ATTATTGTAT  GTATCGTGTA  AAGGAAGTCT   240

GTA                                                                      243
```

( 2 ) INFORMATION FOR SEQ ID NO:164:

( i ) SEQUENCE CHARACTERISTICS:
    ( A ) LENGTH: 266 base pairs ( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:164:

| | | | | | |
|---|---|---|---|---|---|
| CCTGGGTCCG | TCCTCCAACC | CCTCACGCCC | AAACCCTCCG | ACTTTCACTT | CTTGAAGTGA | 60 |
| TCGGAAAGGG | CAGTTTTGGA | AAGGTTCTTC | TGGCTAGGCA | CAAGGCAGAA | GAAGTATTCT | 120 |
| ATGCAGTCAA | AGTTTTACAG | AAGAAGCCAT | CCTGAAGAAG | AAAGGAAGGA | AGCATATTAT | 180 |
| GTCAGAGCGG | AATGTTCTGT | TGAAGAATGT | GAAGCACCCT | TTCCTGGTGG | GCCTTCACTT | 240 |
| CTCATTCCAG | ACCGCTGACA | AGCTCT | | | | 266 |

( 2 ) INFORMATION FOR SEQ ID NO:165:

( i ) SEQUENCE CHARACTERISTICS:
( A ) LENGTH: 204 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:165:

| | | | | | |
|---|---|---|---|---|---|
| GATGCTGAAC | ACAAAAAGAA | AGAAGAAAAG | GAAGAGGAGG | AGCAAGAGAA | GCTGAAGGGA | 60 |
| GGGAGCCTTG | GCGAAAATCA | GATCAAAGAT | GAGAAGATTA | AAAAGGACAA | AGAGCCCAAA | 120 |
| GAAGAGTCAA | GAGCTTCTTG | GATAGAAAGA | AAGGATTTAC | AGAGTGAGGC | GCAGAATGGA | 180 |
| GATTCATGAC | CCACAAACTT | AAAC | | | | 204 |

( 2 ) INFORMATION FOR SEQ ID NO:166:

( i ) SEQUENCE CHARACTERISTICS:
( A ) LENGTH: 200 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:166:

| | | | | | |
|---|---|---|---|---|---|
| AAAGCCAATT | GGTAGAGAAA | TTGAAGACAC | AAATGCTGGA | TCAGGAAGAG | CTTCTGGCAT | 60 |
| CAACCAGAAG | GGATCAAGAT | AATATGCAAG | CTGAACTGAA | TCGCCTCCAA | GCAGAAAATG | 120 |

| ATGCTTCTAA | AGAAGAGTAA | AGAGTTTTAC | AGGCCTTAGA | GGACTGCTGT | TAATTATGAT | 180 |
| CAGAGTTCAG | GAGTTAAGAC | | | | | 200 |

( 2 ) INFORMATION FOR SEQ ID NO:167:

( i ) SEQUENCE CHARACTERISTICS:
        ( A ) LENGTH: 337 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:167:

| CTGCTTGATG | TCCTGTGTAG | CGAATGTCAC | AGCGTACAAC | ATTGTTAGTG | TAGTCTGATT | 60 |
| CAGGCACCAG | GTAGCTGGGG | TTTACACTGA | CCTTTAGAAT | GTAGTTTCCA | GGTTGTACAT | 120 |
| CTGTAATATC | AATCCACTGG | CAGTCTATGT | CTGCCGCATA | GGTGTCATAA | CATCCAGGAC | 180 |
| TCAATCCCTG | TGTGTGTGCA | GTGCACGCAA | AGGCCCTGTG | GTACCCATAG | TCACAGGACG | 240 |
| TGTCCTCCAG | ACAGAAGCTT | GCTTTGTGGC | CTTCAGCCAC | TCTCCTCTGT | GTGTTGGCAT | 300 |
| CAACGAGAAG | CCGAATTCTC | GAGATATCCA | TCACACT | | | 337 |

( 2 ) INFORMATION FOR SEQ ID NO:168:

( i ) SEQUENCE CHARACTERISTICS:
        ( A ) LENGTH: 337 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:168:

| CTGCTTGATG | TCCTGTGTAG | CGAATGTCAC | AGCGTACAAC | ATTGTTAGTG | TAGTCTGATT | 60 |
| CAGGCACCAG | GTAGCTGGGG | TTTACACTGA | CCTTTAGAAT | GTAGTTTCCA | GGTTGTACAT | 120 |
| CTGTAATATC | AATCCACTGG | CAGTCTATGT | CTGCCGCATA | GGTGTCATAA | CATCCAGGAC | 180 |
| TCAATCCCTG | TGTGTGTGCA | GTGCACGCAA | AGGCCCTGTG | GTACCCATAG | TCACAGGACG | 240 |
| TGTCCTCCAG | ACAGAAGCTT | GCTTTGTGGC | CTTCAGCCAC | TCTCCTCTGT | GTGTTGGCAT | 300 |
| CAACGAGAAG | CCGAATTCTC | GAGATATCCA | TCACACT | | | 337 |

( 2 ) INFORMATION FOR SEQ ID NO:169:

( i ) SEQUENCE CHARACTERISTICS:
        ( A ) LENGTH: 374 base pairs
        ( B ) TYPE: nucleic acid
        ( C ) STRANDEDNESS: single
        ( D ) TOPOLOGY: linear ( i i ) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:169:

```
GATCTGACAC TACAGCATGA GCGTTAGATT TCATAAAATT ATTTTTCTTC TAAATGCTGG      60
AAACTCTAAG GGTTTATTCA GAAAAAAAC  TGGCCAATTT TCAAATGGCT TAGAAGCAGG     120
GTTAATTAAG TATTGAATGA GCCACTGTGA TATCCTGATG ACACCCAGTC ACAATGACAG     180
TTTTGAAGCA TACAACCAAA ACAATTGAGA TCTCAAAACT ATTTACATC  ACTTATGGTA    240
ATGTTATGTA AAAATGAAAA TGCTTTCTGT GGAAGTTACA TTCTTTACCA GGTCTTTAAC    300
ATAAATTAAC ACGACGTCGA GTAAGCCTTT GTTCGGAAGA CAAACTAGTT TGTGAGTTCA    360
GTCAGATCCC AGCT                                                     374
```

(2) INFORMATION FOR SEQ ID NO:170:

(i) SEQUENCE CHARACTERISTICS:
    (A) LENGTH: 334 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:170:

```
AGTTGCCAGG ACCACCACCA TAGTTGCCAG GTTCATCATA AACAAATCCA ACATCAATCT      60
TAAATTCCCC CATCAGACAA TCTGCCCTCA AAGAATGGGA ATTATAAACC CGGATACTGA    120
TGATCTCATC CATGAGCTCA GAGGGTGTGA TGTGCACATT GTAGAAAAAT AACTCGTCAA    180
AAAACGGATT GTTCCCTCTC TTGATTCTCG TGCGATGCGT CTGACCACAG ATGTGAACTT    240
TCACCACGGG CCTTATGTTG TTGCCGCATA ACTGACGGCC CTCGATCACT CTGACACGGA    300
TCTGGAAATC TGTGGCTTGT TGGACAGCAT CCTT                                334
```

(2) INFORMATION FOR SEQ ID NO:171:

(i) SEQUENCE CHARACTERISTICS:
    (A) LENGTH: 380 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:171:

```
AAGCCGTGTC CCAAAGAATG GATAGAGACG CGATCAGATG CGACAGTGCT GTGGAGAAAG      60
```

```
CCCAGGAACC  TGCACAATTG  CCCTGGTCCA  ATGGCTCGTG  GATCAGGTTG  GGCCACTTCT    120

CTGAAGCTTC  AAAGGCAGTG  GGTAGCACTT  CCCCTTGGCC  CAGCACCGTA  TAAATCTCAT    180

TCATATTCAT  GACAGTGGAG  GATGGGCGGA  TTGTGCCCAG  GCGGTACGGA  ATGCCCTCAT    240

CCAGGGTCAT  GCCCCAGAAG  GCACTGTGGT  TCCCAGCCTG  CCACCCGTAG  TTGCCTCGGT    300

TGATGGCTTT  AATCATGTCT  GGTCACTAGA  CACGGCTTAA  GCGAATCTCG  AGATATCCAT    360

CACACTGGCG  GCGTCGAGAT                                                    380
```

( 2 ) INFORMATION FOR SEQ ID NO:172:

( i ) SEQUENCE CHARACTERISTICS:
        ( A ) LENGTH: 353 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:172:

```
AAGCCGTGTC  TGATGATGGA  GGTAGTGGTG  GGGGAGGAGG  GACTGAGGGT  CCTGAGGTGG     60

TGGCCCCTGG  AACTGATCCC  ACATAGTTAC  CCACTGCTAG  TTCTGACCCC  GTGGACAACG    120

TGCCAGAGGC  CATGACTGGC  AGTATGGCAA  TGTCCCCATC  CCCTTCTTC   TTAATTTTAA    180

TGGTCCCTTG  TTTCTCCAGT  TCGTGAATCT  TTTTTCCAG   GGTAGACTGT  CTTTGAATGG    240

CTTCTTCCTT  TTCTTTGACC  ATTTTTCTTA  ACGTGTGAAC  TTGGGTATTT  GCATCTTTGT    300

AGATTTCCGG  ACAACATCAG  TTCCTTATTC  CTCTGCATAA  GTTGCTTTCA  GTT           353
```

( 2 ) INFORMATION FOR SEQ ID NO:173:

( i ) SEQUENCE CHARACTERISTICS:
        ( A ) LENGTH: 350 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:173:

```
CGAGTCAGAC  ACATGAAAGC  AAAACGCGGG  CAGATAAAAC  GATCGCCTTA  CCTTCTAGCA     60

AAAATCTGAA  GCTTGTGTCA  GAAACAAAGA  CTCAGAAAGG  TTTGTTTTCA  GATGAAGAAG    120

ACTCTGAGGA  TTTGTTTTCT  TCTCAAAGTT  CAAGTAAGCC  AAAAAGTGCA  TCACTTTCAT    180

CCAGCCAGCC  CCCAACATCA  GTCTCCCTTT  TGGTGATGA   AGATGAAGAG  GACAGTCTTT    240

TTGGGAGTGC  AGCAGCTAAG  AAGCAGACTT  CATCTCTACA  ACCTCAGAGT  CAAGAGAAAG    300

CAAAGCCTTC  CGAGCAGCCC  TCAAAGAAGA  CATCTGCCTT  GTTGTTCAGA                350
```

( 2 ) INFORMATION FOR SEQ ID NO:174:

( i ) SEQUENCE CHARACTERISTICS:
        ( A ) LENGTH: 377 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:174:

```
CGAGTCAGAC TTAATTTAAA AACGAAACAA AACAAAAATA ACATAGTTTA GAAATCAAGG    60
AGAAAGGACA GATAGTCTAA GAAAAAAGAC AACACAAAAG AGGGGCAGGG CGGCCAGCTT   120
GCATCAGGGA TCTTGGCTGG AGACCTGCTT TGAATAGGTT TCTTGCAGGT ATTTCTTAAA   180
TGCTGTGGGG TTTTTCCAGA GTTCGCAGC  GTGTGTGTTC AAAGGGCTAT CGATGTTGGG   240
TTCTCCTAGC AGGCTCTGGA TAGAGAGCAA GATAGTCCTG ACATCATATA GTGCAGACCA   300
CTTATCCTTG AGGATGTCCG GCAGATGTTG CCTGGGTGTC ACGTTGGGGT GGTAGCAGGG   360
TGTGAGGAAC TTCACTG                                                  377
```

( 2 ) INFORMATION FOR SEQ ID NO:175:

( i ) SEQUENCE CHARACTERISTICS:
        ( A ) LENGTH: 326 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:175:

```
CGAGTCAGAC ACTCCTGGCT CCTGGATTCT TTAGATGCCT CCATCAGACT GGGTACTTTA    60
GATGCCTCCA TCAGACTACT TCGTCATTGT ATTTCTCAGT TCGCTCAGGG CAAGCGGCAG   120
TCTCTGGGCT GCTGTGGCAG GTGCCACCAC TGCATTTAAA AGTTAAAATT TCTTCAAATA   180
TTCCCATCAA GGCCTTGTAG CCTCTGAGAT TGGTTTACTA TTTGCCCAGT TATTTAAAGC   240
TCTCTGCATT CCTTCCTGAT TTAATATTGC TATGGCCAGG ACAATGTGTA GAAGTAAAAA   300
GGATATCATA TTTACAGGTG TAACGC                                        326
```

METHOD FOR IDENTIFYING METASTATIC SEQUENCES

RIGHTS IN THE INVENTION

This invention was made in part with United States Government support under grant number CA350129, awarded by the National Cancer Institute, National Institute of Health and the United States Government has certain rights in the invention.

REFERENCE TO RELATED APPLICATION

This patent application is a continuation of United States provisional patent application, serial number 60/006,838, filed Nov. 16, 1995.

BACKGROUND

1. Field of the Invention

The present invention relates to methods for the identification and isolation of metastatic sequences, to diagnostic probes and kits which contain metastatic sequences and to therapeutic treatments for neoplastic disorders based on metastatic sequences.

2. Description of the Background

The development of higher organisms is characterized by an exquisite pattern of temporal and spatially regulated cell division. Disruptions in the normal physiology of cell division are almost invariably detrimental. One such type of disruption is cancer, a disease that can arise from a series of genetic events.

Cancer cells are defined by two heritable properties, uncontrolled growth and uncontrolled invasion of normal tissue. A cancerous cell can divide in defiance of the normal growth constraints in a cell leading to a localized growth or tumor. In addition, some cancer cells also gain the ability to migrate away from their initial site and invade other healthy tissues in a patient. It is the combination of these two features that make a cancer cell especially dangerous.

An isolated abnormal cell population that grows uncontrollably will give rise to a tumor or neoplasm. As long as the neoplasm remains in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from epidermiological and clinical studies, most cancers develop in slow stages from mildly benign into malignant neoplasms. Malignant cancer usually begins as a benign localized cell population with abnormal growth characteristic called a dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the more clear examples of the progression of normal tissue to benign neoplasm to malignant neoplasm.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma; a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder. Left untreated, a percentage of these prostate hyperplasia and neoplasias may develop into malignant prostate carcinoma.

In its more aggressive form, transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasions typically involve the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Surgery or radiotherapy is the treatment of choice for early prostatic neoplasia. Surgery involves complete removal of the entire prostate (radical prostatectomy), and often removal of the surrounding lymph nodes, lymphadenectomy. Radiotherapy, occasionally used as adjuvant therapy, may be either external or interstitial using $^{125}$I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. Despite the advances made in achieving a pharmacologic orchiectomy, the survival rates for those with late stage carcinomas are rather bleak.

SUMMARY OF THE INVENTION

The present invention overcomes the problems and disadvantages associated with current strategies and designs and provides new methods for the identification of sequences related to metastasis.

One embodiment of the invention is directed to methods for the identification of a metastatic sequence. One or more oncogenic sequences are transfected into a cell to form a transfected cell. The transfected cell is introduced into a primary site of a host animal to establish a colony which is incubated in the animal for a period of time sufficient to develop both a primary tumor and a metastatic tumor. Expressed sequences are harvested from the primary tumor and the metastasis. Harvested sequences are compared to each other and to non-metastatic cells to identify sequences related to metastasis. Dominant metastatic genes are genes whose expression leads to metastasis. Such genes are typically expressed at high levels in metastatic cells and not significantly expressed in normal or nonmetastatic cells. Recessive metastatic genes, genes whose expression prevents metastasis, may be selectively expressed in normal and nonmetastatic cells and absent in metastatic cells. Dominant and recessive metastatic genes may act directly or act pleiotropically by enhancing or inhibiting the expression or function of other dominant and recessive metastatic genes.

Another embodiment of the invention is directed to methods for identifying metastatic sequences. A mammalian cell is treated with a metastatic agent and the treated cell is implanted into a primary site of a host mammal. The host animal is maintained for a period of time sufficient for the cells to proliferate and to develop a metastatsis at a secondary cite. Expressed squences from cells of the primary cite and cells of the secondary site are reverse transcribed into cDNA by differential display polymerase chain reaction to identify differentially expressed sequences.

Another embodiment of the invention is directed to sequences isolated by the methods of the invention. Sequences may be in the form of DNA, RNA or PNA. The nucleic acid may be single-stranded or double-stranded. Single stranded nucleic acid may be in the form of a sense strand or an antisense strand. In addition, the sequence may be part of a homologous recombination vector designed to recombine with another metastatic sequence.

Another embodiment of the invention is directed to a method for treating a neoplastic disorder comprising administering a pharmaceutically effective amount of a metastatic nucleic acid to a patient. The nucleic acid may be single-stranded in the sense or the antisense direction. Alternatively, the nucleic acid may be packaged in a viral vector such as, for example, a retroviral, a vaccinia or an adenoviral vector. Administration may be performed by injection, pulmonary absorption, topical application or delayed release of the nucleic acid along with a pharmaceutically acceptable carrier such as water, alcohols, salts, oils, fatty acids, saccharides, polysaccharides and combinations thereof.

Another embodiment of the invention is directed to a kit for detecting of the presence or absence of a metastatic sequence.

Other objects and advantages of the invention are set forth in part in the description which follows, and in part, will be obvious from this description, or may be learned from the practice of the invention.

FIG. A–RR 12 Nucleotide sequences of metastatic nucleic acids.

FIG. 13 A–D Characterization of metastatic sequences isolated.

Figure 14A:
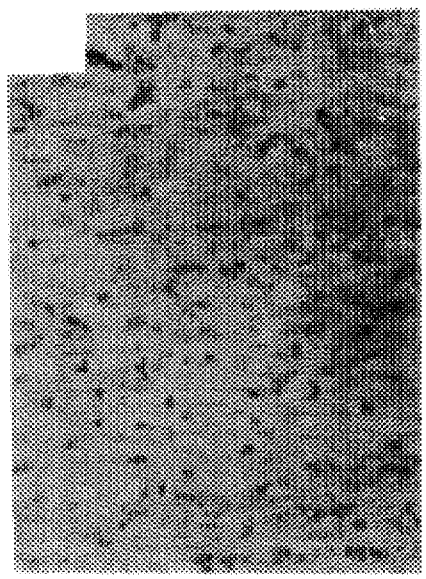
Figure 14B:
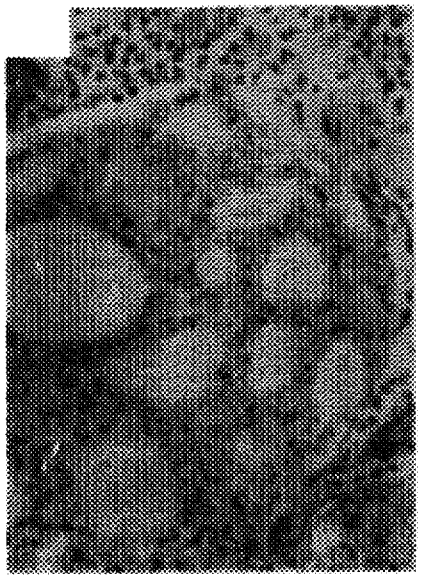

FIG. 14 Immunohistological staining of primary and metastatic human prostate tumors using anti-caveolin antibodies.

DESCRIPTION OF THE INVENTION

As embodied and broadly described herein, the present invention is directed to methods for identifying metastatic sequences, to the metastatic sequences identified, to methods for the detection, diagnosis and treatment of disorders related to metastasis, and to diagnostic kits which comprise these sequences.

Figure 1A:
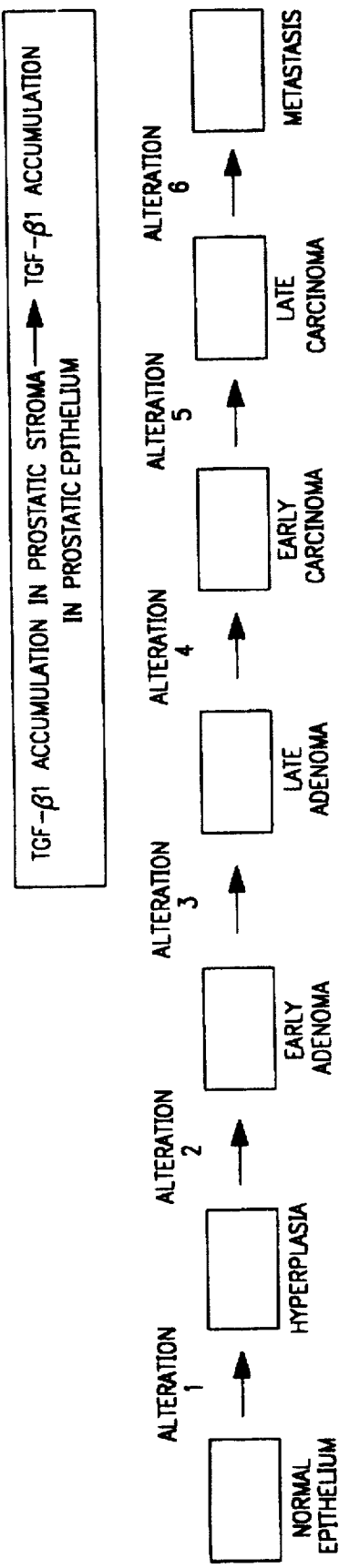
FIG. 1 Schematic showing two paths in the multistep progression to cancer.
Figure 1B:
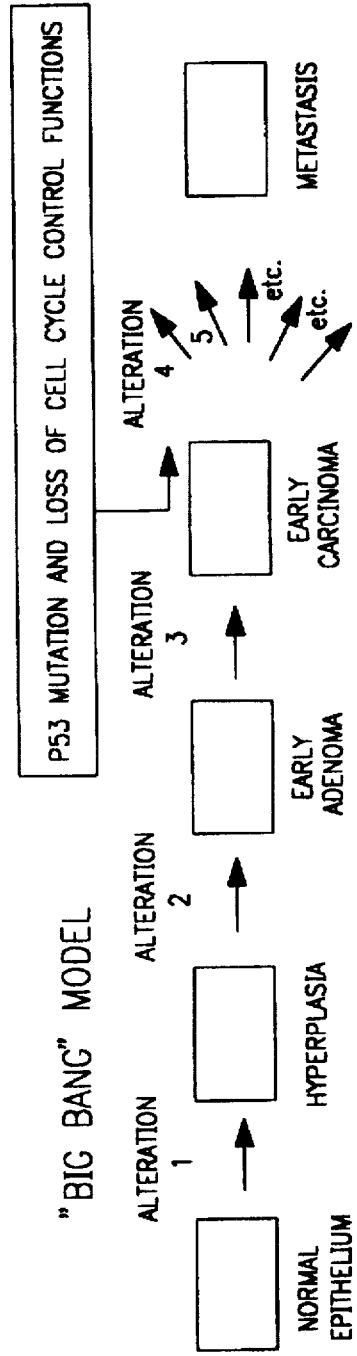

The ability of cancers to metastasize makes tumors difficult to eradicate by any means. Malignant cancer involves a multistage progression from, for example, normal tissue through hyperplasia, early adenoma, early carcinoma and finally to a metastatic tumor (FIG. 1). Cells of a typical tumor loosen their adhesion to their original cellular neighbors and cross the basal lamina and endothelial lining to enter the body's circulation. Once in circulation, the metastatic cell exits from the circulation to disseminate throughout body and proliferate in a new environment.

Like the initial oncogenic event, the ability of a cell to metastasize requires additional mutationic or epigenetic changes. An understanding of the molecular mechanisms of metastasis allow for the design of treatments to inhibit metastasis. Knowledge of stage specific gene expression for neoplastic disorders allows for early detection and typing of tumors. With early detection and typing, proper treatment may be administered to a patient with the neoplastic disorder earlier, which will lead to a higher probability of a complete cure.

For human prostate tumors, the study of stage specific tumors is difficult, if not impossible, as cell lines are extremely difficult to grow and it is rare that tissue becomes available from the primary tumor as well as metastatic disease from the same patient. This problem is exacerbated because of the infrequent biopsy of metastatic deposits in conjuntion with isolation of material from the primary tumor. Furthermore, the growth of cell lines from malignant prostates has proved to be problematic over the last few decades. This is evidenced by the lack of cell lines from prostate cancer obtained under any conditions.

One embodiment of the invention is directed to a method for identifying a metastatic sequence. A mammalian cell is transformed into a pre-neoplastic or neoplastic state or phenotype by transfection with one or more oncogenic sequences. Alternatively, or in addition to transfection, the mammalian cell may be treated with an agent or subjected to a condition that potentiates the metastatic character of the cell or predisposes the cell to metastasis. The transfected or treated cell is implanted into a host animal at a primary site and grown for a period of time sufficient to develop a metastasis at a secondary site. Expressed sequences from cells of the primary site and cells at the secondary site are amplified by differential display polymerase chain reactions. PCR products from these reactions are compared and the metastatic sequence identified by alteration in the levels or patterns of the resulting products.

Mammalian cells from a wide variety of tissue types and species are suitable for transfection or treatment including surgically obtained or primary or immortalized cells and cell lines. Cells may be from humans or primates, mice, rats, sheep, cows, rabbits, horses, pigs or guinea pigs or from transgenic or xenogeneic host mammals. Cells may be obtained from adult, juvenile or fetal tissue, and used directly from the mammal, from cryogenically preserved samples, or after culturing in vitro or in vivo for a period of time. In vitro culturing typically involves tissue culture conditions (e.g. 37° C.; 5% $CO_2$) while in vivo culturing may involve successive passage of cells through host animals such as, for example, mice or rabbits. Cells passed in vivo may be obtained from sites proximal or distal to the site of implantation. The tissue type from which the cells are derived or obtained may be any tissue which is susceptible to transfection or other treatment including, for example, urogenital tissues, epithelial cells, hepatic cells, fibroblasts lymphatic tissues, hematopoietic cells, cells of the immune system, cells of the gastrointestinal system and cells of the nervous system.

Figure 5A:
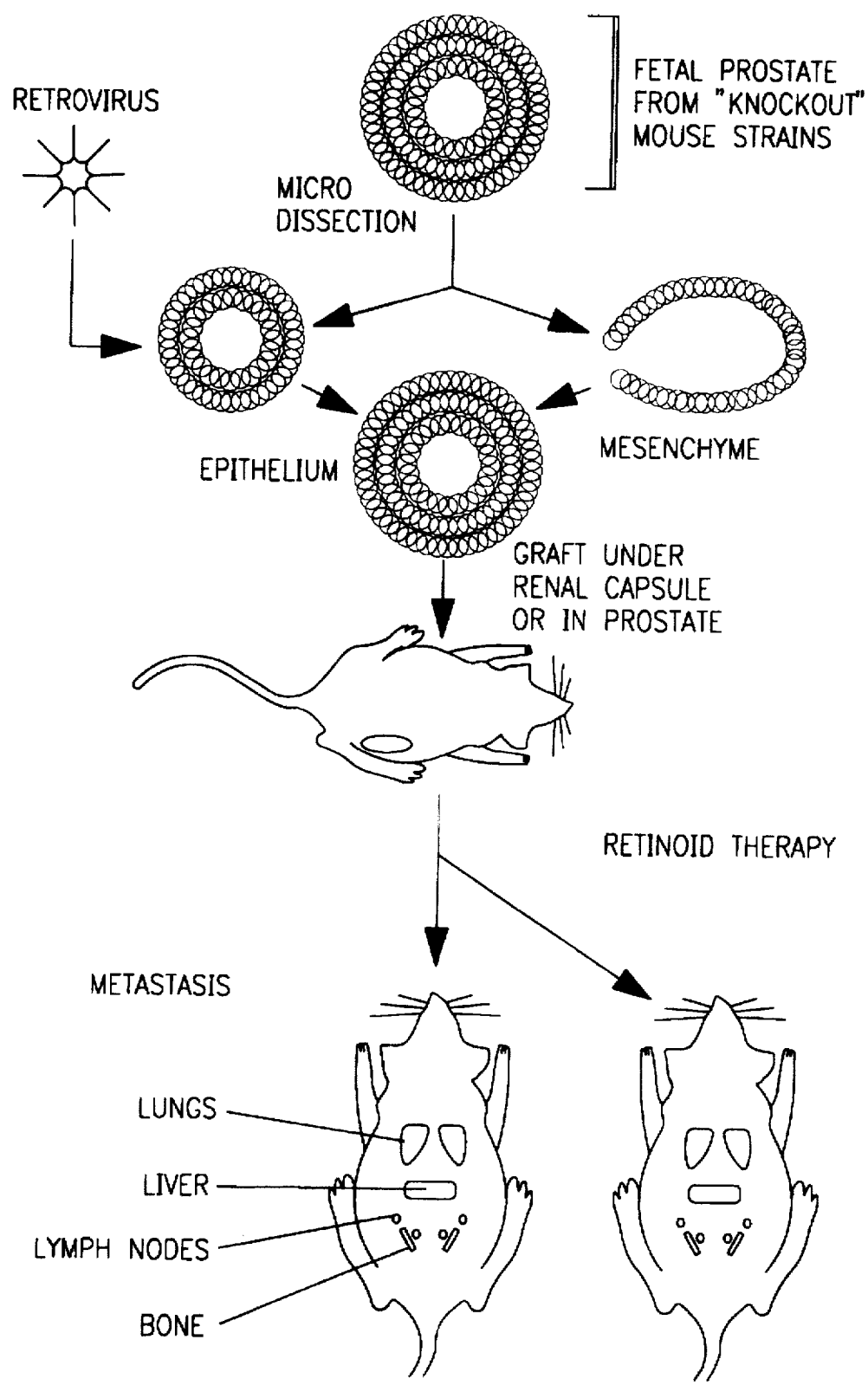
FIG. 5 A–B Schematic showing method to establish a tumor and a metastatic transplant from fetal tissue(A) and from cell lines and tumors (b).

Cell types useful for the identification of metastatic sequences related to prostate cancer include cells and cell lines of the fetal prostate lineage from normal or transgenic animals, and cells from normal or reconstituted prostate tissue. One method of generating reconstituted prostate cells is to isolate fetal prostate tissue and microdissect the fetal prostate epithelium away from fetal mesenchyme. Fetal prostate epithelium may be genetically manipulated before reassociation with fetal mesenchyme (FIG. 5A). Genetic manipulation involves treatment or transfection with a metastatic agent or a nucleic acid sequence that affects neoplastic or metastatic potential of the cell. Reassociation of fetal epithelium and mesenchyme is performed by implanting epithelial tissue within a pocket of mesenchymal tissue. After manipulation, cells are reimplanted into a mammalian host in a similar manner as other cells, such as reimplantation into or under the renal capsule.

Mammalian cells may be transfected by a variety of techniques, all of which are well-known to those of ordinary skill. Direct methods involve the introduction of genetic material into the nucleus of a cell by injection. These techniques include high velocity projectile injection, microinjection, and electroporation. Indirect methods, involving the active or passive uptake of the genetic information by the cell, include transduction with recombinant vectors, and chemical or physical treatments such as calcium phosphate uptake, lipofection or dextran sulfate transfection. Chemical techniques rely on chemical carriers to introduce nucleic acids into a cell. These methods, for example, utilize unilamellar phospholipid vesicles (e.g. liposomes) loaded with DNA (or RNA). The approach relies on the fusion of the DNA containing vesicles with the plasma membrane of the recipient cells. After entry, DNA traverse the cytoplasm and enter the nucleus. Another lipofection technique uses a synthetic cationic lipid such as N-[1-(2,3-dioleyloxy)propyl] -N,N,N-trimethylammonium chloride (DOTMA). DOTMA spontaneously associates with nucleic acids and forms unilamellar vesicles upon sonication. Genetic material is incorporated into these vesicles and subsequently transfected into the cell. Calcium phosphate co-precipitation involves mixing of purified nucleic acid with buffers containing phosphate and calcium chloride which results in the formation of a fine precipitate. Presentation of this precipitate to cells results in incorporation of the nucleic acid into cellular genome. Other chemicals, such as DEAE dextran or polybrene, when present in media with nucleic acids, can also cause the transfection of mammalian cells.

Physical methods of transfection rely on electric fields, needles and particles to enable nucleic acids to traverse the cellular membrane. Electric field mediated DNA transfection, commonly called electroporation, is based on the principle that membranes, when subjected to an electric field, undergo a reversible breakdown resulting in pores large enough to permit the passage of nucleic acids. In micro-projectile mediated gene transfer, micro-projectiles of subcellular dimensions are coated with nucleic acid and propelled at high velocity into a cell using a particle gun. The nucleic acid is introduced into the nucleus directly when the particles impinge upon the nucleus. In microinjection, nucleic acid is injected directly into the nucleus of a cell with a needle. Lasers have also been used to introduce minute holes in cellular membrane to allow introduction of nucleic acids. All these methods may be used for transfection and the selection of the method will depend on the cell type, the desired transfection efficiency and the equipment available.

The efficiency of transfection may be monitored and enhanced by the co-transfection of a selectable marker. If a marker is co-transfected with a genetic construct, positively transformed cells may be separated from nontransformed cells by chemical selection. The efficiency of transfection will be increased in most cases because the chemicals will selectively kill non-transfected cells. The number of transfected cells may also be monitored by analyzing the degree of chemical resistance of the transfected cells. Markers commonly used for selection purposes include, for example, nucleic acids encoding dihydrofolate reductase, metallothionein, CAD, adenosine deaminase, adenylate deaminase, UMP synthetase, IMP 5'-dehydrogenase, xanthine-guanine phosphoribosyltransferase, mutant thymidine kinase, mutant HGPRTase, thymidylate synthetase, P-glycoprotein 170, ribonucleotide reductase, glutamine synthetase, asparagine synthetase, arginosuccinate synthetase, ornithine decarboxylase, HMG-CoA reductase, N-acetylglucosaminyl transferase, theronyl-tRNA synthetase, sodium or potassium dependent ATPase or derivatives or mutants of these nucleic acids. Markers may be used individually or in combination. Chemicals useful for selection include methotrexate, cadmium, PALA, Xyl-A, adenosine, 2'-deoxycoformycin, adenine, azaserine, coformycin, 6-azauridine, pyrazofuran, mycophenolic acid, limiting xanthine, hypoxanthine, aminopterin, thymidine, 5-fluorodeoxyuridine, adriamycin, vincristine, colchicine, actinomycin D, puromycin, cytocholasin B, emetine, maytansine, Bakers' antifolate, aphidicolin, methionine sulfoximine, β-aspartyl hydroxamate, albizziin, canavanine, α-difluoromethylornithine, compactin, tunicamycin, borrelidin, ouabain, and derivatives and analogs and combinations of these chemicals. Some chemicals, such as methotrexate, may be used individually while other chemicals, such as HAT (hypoxanthine, aminopterin and thymidine), need to be used in combination to be effective.

The oncogene transfection efficiency, the fraction of live cells tranfected by an oncogene, may be indirectly enhanced by chemical selection for a co-transfected marker. An oncogene is a sequence which can predispose, or induce the cell into a pre-neoplastic or neoplastic condition or otherwise enhance the metastatic potential of the cell. Sequences with these properties are referred to as oncogenes and include abl, ahi, akt, bcl, crk, dsi, erb, ets, evi, fes/fps, fim, fis, fgr, flv, fms, fos, gin, gli, int, jun, kit, mas, lck, met, mil/raf, mis, mlv, mos, myb, myc, neu, onc, pim, raf ras, rel, ros, seq, sis, ski, spi, src, tcl, thy, trk, and yes. Some oncogenes, such as ras, are oncogenic when mutated. Other oncogenes, such as myc, are oncogenic when overexpressed or underexpressed. Many oncogenes represent members of multigene families or homologs families. Homologs are proteins that have similar primary, secondary or tertiary structures. Genes may differ in nucleic acid sequence or encoded peptide sequence and still be homologs when the encoded polypeptides have similar spatial folding. Many oncogenes can be classified into dominant oncogenes and recessive oncogenes. One or more dominant oncogenes can confer a neoplastic or pre-neoplastic phenotype to a cell. One or more recessive oncogenes, when silenced, may also confer a neoplastic or preneoplastic phenotype. Gene silencing is performed by transfecting cells with nucleic acids which cause genetic ablation or by antisense suppression.

While any oncogene may be used, the preferred oncogenes are those that are normally associated with metastasis such as a metastasis specific gene. Such genes include for example, TGF-β1, Cyclin D1 p21, p34, p53, lysyl oxidase, caveolin, actin binding protein, ubiquitin activating enzyme E1, nmb or α-actinin 3. Metastatic-specific genes may be used individually or in combination with other oncogenes.

The metastatic potential of a cell may be altered, for example, by gene ablation with a sequence specific for a recessive oncogene. Recessive oncogenes are those genes which encode products which can suppress oncogenesis and metastasis. A gene ablation sequence can be designed to specifically suppress a recessive oncogene. Ablation may include pre-transcriptional inhibition such as homologous recombination with endogenous recessive oncogenes and post transcriptional inhibition such as the expression of antisense oncogenes to suppress translation. Gene ablation sequences may be targeted towards well known recessive oncogenes such as, for example, the retinoblastoma gene (Rb) or Bcg. Other candidates for ablation include metastatic genes previously isolated by the invention such as, for example, TGF-β1, cyclin D1, p21, p34, p53, lysyl oxidase, caveolin, actin binding protein, ubiquitin activating enzyme E1, nmb or α-actinin-3. The effects of ablating a recessive oncogene may include oncogenesis and metastases.

Alternatively, or in addition to transfection the mammalian cell may be treated with an agent, either before or after transfection, that alters the expression of the cell's nucleic acids. Treatment may comprise contacting the cells with one or more agents which affect the neoplastic predisposition (e.g. neoplastic agents; phorbol esters), metabolization (e.g. metabolic agents), metastasis (e.g. metastatic agents), differentiation (e.g. differentiation agents; retinoic acid), activation or proliferation (e.g. growth factors) of the cell. Agents which can alter gene expression include chemicals such as benzanthracene (BA), dimethyl benzanthracene (DMBA) or 5-azacytidine. Alternatively, treatment may also comprise altered conditions such as hypoxia which involves subjecting a cell to a reduced oxygen content, exposable to radiation or other stresses to the cell.

Treatment may be in vitro or in vivo and may include for example, direct or indirect induction or suppression of well known oncogenic sequences and genes isolated by the invention such as, for example, TGF-β1, Cyclin D1, p53, lysyl oxidase, caveolin, actin binding protein, ubiquitin activating enzyme E1, nmb, α actinin 3, and p34. Gene expression induction includes transfecting expression vectors encompassing coding regions of the gene. Gene repression comprises introducing a gene ablation sequence or a repressor of the gene to the cell.

Cells which have one or more genes ablated may also be used. For example, a metastatic suppressor gene may be ablated to prevent inhibition to metastases. A useful gene for ablation is a gene capable of affecting the phenotype and behavior of a cell or tumor. For example, with prostate tumors, suitable genes include both well known genes and genes isolated by the methods of the invention such as for example, TGF-β1, Cyclin D1, p21, p34, p53, lysyl oxidase, caveolin, actin binding protein, ubiquitin activating enzyme E1, nmb and α actinin 3. Genetic ablation (gene knockout) refers to a process of silencing the expression of a particular gene in a cell. The silencing process may include, for example, gene targeting or antisense blocking. Gene targeting refers to a process of introducing a nucleic acid construct into a cell to specifically recombine with a target gene. The nucleic acid construct inactivates the targeted gene. Inactivation may be by introduction of termination codons into a coding region or introduction of a repression site into a regulatory sequence. Antisense blocking refers to the incorporation into a cell of expression sequences which directs the synthesis of antisense RNA to block expression of a target gene. Antisense RNA hybridizes to the mRNA of the target gene to inhibit expression.

The host animal is preferably the same species as the implanted cell. In cases of xenogeneic transplants, the host may be immunocompromised genetically or by treatment with drugs such as immunosuppressants. A host may be immunocompromised genetically by breeding such as with nude mice or severe combined immunodeficient (SCID) mice. A host may also be immunocompromised by chemical or irradiation methods. An additional route to immunocompromise a host is to use transgenic technology to introduce an immunosuppressing gene or to introduce a foreign antigen gene. An immunosuppressing gene is a gene that affects the efficiency of the immune system such as a gene which inhibits the formation of cells of the B cell or T cell lineage. A foreign antigen gene, when expressed, may cause the host to tolerate the antigens in a xenogeneic transplant and not mount an immune response.

Cells may be implanted into any primary site in a host animal, such as, for example, subcutaneous implantation, intravenous injection, or implantation into the abdominal cardiac, chest, pulmonary, thoracic or peritoneal cavity. Using techniques known to those of ordinary skill in the art, cells can be placed on or in nearly any organ or tissue. Reasons for choosing a site include ease of implant, proximity of similar tissue type, immunoprivileged position and ease of inspection. Metastasises migrate from the primary site to one or more secondary sites such as, for example, the lung, kidney, liver, lymph nodes, brain, testis, bone, spleen, ovaries or mammary. Preferred sites include the renal capsule, the testes, the prostate and the ovaries.

To avoid histocompatibility problems, the implant may be placed into a histocompatible host animal. Such problems are generally avoided if the implant and host animal are syngeneic. Alternatively, a non-histocompatible host may be used if the host can be made immunotolerant. Hosts may also be transgenic or immunocompromised animals or genetically matched to the mammalian cells to be introduced. Immunocompromised animals may be derived from established mouse lines such as nude mice or severe combined immune deficiency (SCID) mice, or by treatments such as radiation, chemical, pharmaceutical or genetic targeting. Sufficiently immunosuppressed animals can be made tolerant to xenogeneic transplants.

After implantation the host animal is maintained under normal conditions to develop metastases. Alternatively, the host animal may be subjected to an altered treatment or environmental condition to stimulate or repress metastasis or induce other cellular functions. In metastasis, a subpopulation of cells of the implantation site invade and establish one or more secondary colonies in the host animal. The behavior of the implanted cell will depend on the cell type, the transfected sequence and the implantation location. Typical secondary sites for metastatic colonies include lung, kidney, liver, lymph nodes, brain, testis, spleen, bone, ovary, skin and mammary tissue. Metastatic development times vary from days to weeks even months. Cells with a high metastatic potential tend to progress to metastasis quickly while cells with a low metastatic potential may require very long periods of time that span significant portions of the lifespan of the animal.

The host animal may be analyzed for metastatic development weekly, from one week to 20 weeks to six months, nine months or one year after implantation. For animals with longer lifespans such as sheep, the animal may be inspected yearly from one year on up to ten years for metastatic tumors. Metastases can be detected by examinations such as palpation, biopsy, imaging, exploratory surgery, CAT scans, autopsy, X-ray and direct observation. In addition, tissue samples may be taken surgically from the host mammal and subjected to histological or other examination for the detection of metastases.

Expressed sequences include mRNA, rRNA, hnRNA, DNA, cDNA and any nucleic acid sequence that is expressed in the cell. These sequences may be amplified by in situ techniques or by purification of nucleic acid from collected cells. Expressed sequences may be obtained by extracting nucleic acids from cells before implantation, at the primary site or at the secondary site. Cells collected at these sites may optionally be cultured for a time before nucleic acid extraction. The effects of treatment with gene expression modifying agents or environmental conditions can be ascertained by collecting cells before and after treatment. Treatment may be applied to the cells while the cells are in the host mammal or after the cells are excised and in culture. Nucleic acid are collected from cells using techniques that are well known to those of ordinary skill in the art.

Expressed sequences may be used directly for polymerase chain reaction (PCR) analysis using, for example, the technique of reverse transcriptase polymerase chain reaction (RT-PCR). Alternatively, RNA may be enriched for mRNA using a poly-A RNA enrichment method. Numerous poly-A RNA enrichment methods exist and are commercially available. Techniques used for poly-A RNA enrichment include oligo-dT columns, oligo-dT magnetic beads, and oligo-dT cellulose. RNA may be further processed into cDNA before analysis by reverse transcription using reverse transcriptase. The cells or the extracted nucleic acid may be preserved, such as by freezing, and analyzed at a later time.

Differential display polymerase chain reactions (DD-PCR) are performed on the expressed sequences using two variable primers which may contain the same or entirely different sequences or an anchor primer and a variable primer. If an anchor primer is used, one anchor primer and one variable primer create a single or a single set of reaction products for each reaction. A complete profile may include 25 or more different PCR reactions per sample wherein each PCR reaction is performed with the same anchor primer and a different variable primer. DD-PCR may also be performed using anchor and variable primers which contain the same sequence. Whether a particular reaction is used depends on whether a difference exists between the products of two PCR reactions using the same primers. When a significant difference exists between the expression sequences amplified, one pair of PCR reactions may be sufficient and informative.

Anchor primers are preferably oligonucleotides with a poly-T sequence at the 5'-terminas and a dinucleotide selected from the group consisting of AA, AG, AC, AT, GA, GG, GC, GT, CA, CG, CC and CT at the 3'-terminas. For example, the sequence may be 5'-TTTTTTAA-3' or 5'-TTTTTTAG-3'. The length of the poly-T sequence is typically between about 5 to about 30 bases in length and preferably between about 10 to about 20 nucleotides long. The total length of the anchor primer can vary greatly for each experiment but is preferably between about 7 to about 32 and more preferably between about 12 and about 22. Differential diagnostic polymerase chain reaction may also be performed using an anchor primer of any sequence and a length between about 5 to about 30, preferably between about 5 to about 20 and more preferably between about 7 to about 12 bases.

The variable primer may comprise a random sequence, or a specific sequence such as, for example, a sequence of SEQ ID NO. 1 to SEQ ID NO. 24. Variable primers preferably are oligonucleotides with a length between about 5 to about 30, preferably between about 5 to about 20, and more preferably between about 7 to about 12 bases in length.

To enhance detection of the PCR product, the anchor primer or the variable primer, or both, may comprise a detectable moiety. Examples of detectable moieties include radioactive moieties, phosphorescent moieties, magnetic moieties, luminescent moieties, conjugatable moieties or other detectable moiety. A plurality of detectable moieties may be used to enhance detection or to simplify data analysis. Other detectable moieties include conjugatable moieties and molecules which can bind specifically to other molecules which are themselves detectable. Examples of conjugatable moieties include avidin, streptavidin, biotin, antibody, antigen, cell adhesion molecules and other molecules with similar activities. Detectable moieties are preferably labeled nucleotides. A nucleotide may be any natural or synthetic nucleotide or nucleotide analog capable of incorporation into an elongation reaction in a polymerase chain reaction. Labeled nucleotides include nucleotide triphosphates labeled with one or more radioactive atoms such as $^{32}P$, $^{33}P$, $^{3}H$, $^{14}C$ and $^{35}S$. Products of DD-PCR reactions are compared to detect the metastatic sequence. Comparisons can be performed between expressed sequences from cells at secondary sites with cells at any stage in the method including untreated mammalian cells, transfected or treated manmmalian cells, implanted cells or cells obtained from the primary site in the host animal. DD-PCR products may be analyzed by any method which reliably compares the products of two polymerase chain reactions. Typical analytical methods used for this purpose include polyacrylamide gel electrophoresis, capillary electrophoresis and high pressure liquid chromatography (HPLC). Product produced from DD-PCR may be analyzed in double-stranded or single-stranded forms. When the products of the DD-PCR reaction are labeled the sizes and distribution of the products may be monitored and analyzed by following the labels using a radiation monitor or by autoradiography. For example, DD-PCR performed in the presence of radioactive primers or nucleotide triphosphates, can be analyzed by gel electrophoresis, by capillary electrophoresis, or by HPLC. Products are easily monitored by the presence of radioactivity.

Another method for analyzing and isolating metastatic sequences is to sequence the amplified nucleic acid sequences. Sequencing may be performed using standard methods well known to those of ordinary skill in the art. The resulting sequence may be compared to a sequence database created or well-known, such as Genbank, for identification or for locating homologs. The sequencing information may be used to calculate the physical characteristics of the nucleic acids such as melting temperature and secondary structure. The primary sequence and the physical characteristic may be used to synthesize optimal nucleic acid probes for the detection or staging of metastasis or conditions that are predictive of the presence or absence of the metastatic condition.

Another embodiment of the invention is directed to a method for identifying a metastatic sequence. A mammalian cell is pretreated with a metastatic agent to form a population of cells predisposed to metastasize. The treated cells are introduced into a host mammal at a primary site. The host animal is maintained for a period of time sufficient to develop a metastasis at a secondary site. Expressed sequences of cells at the primary site and cells at the secondary site are treated with a genotoxic agent or subjected to genotoxic conditions. Expressed sequences of the treated cells are amplified by differential display polymerase chain reaction and compared with untreated cells from any previous step to identify the metastasis sequence.

The metastatic agent may be a chemical compound, a nucleic acid or a protein that alters the metastatic potential of a cell or relates to or is associated with the metastatic process. Chemical compounds include retinoids such as 4-hydroxyphenyl (4HP). Other agents include the proteins TGF-$\beta$1, Cyclin D1, p21, p34, p53, lysyl oxidase, caveolin, actin binding protein, ubiquitin activating enzyme E1, nmb or $\alpha$-actinin 3, or their respective genes. The metastatic agent may be a metastatic stimulant or a metastatic suppressant. Metastatic stimulants may be used to enhance the sensitivity of the metastasis sequence detection method. Conversely metastatic suppressants may be used to decrease the sensitivity of the method enabling the selective identification of potent metastatis sequences or sequences specific to a particular tissue type or metastatic disorder. Treatment may comprise direct contact with the metastatic agent or incubation for a period of time. Metastatic agents enhance the metastatic potential of the implanted cells and increase the sensitivity and the speed of the overall method.

The cells at the primary site and the metastatic cells at the secondary site may be treated with a genotoxic agent in vivo or in vitro. In vivo treatment may comprise injecting genotoxic agents directly into the host mammal or specifically applying the agent with, for example, topical formulations. The cells at the primary site and the secondary site may also be isolated from the host animal and treated with the genotoxic agent in culture. Genotoxic agents are chemical compounds, nucleic acids or proteins that alter gene expression by effecting the nucleic acid genome directly by, for example, chemical modification, or indirectly by, for example, altering components associated with gene expression. Such agents include, for example, benzanthracene (BA), dimethyl benzanthracene (DMBA) and 5-azacytidine, and may include metastatic agents as well. In addition to or in place of genotoxic agents, the cells may be treated to hypoxic conditions or radiation to alter gene expression. Metastatic sequences identified in these methods may be specific for particular genotoxic agents or conditions.

Another embodiment of the invention is directed to the use of a host animal with an altered genotypic or phenotypic predisposition for metastases. A host animal may be screened for endogenous expression of metastases gene. Examples of metastatic sequences which may be screened for include sequences isolated by the method of the invention, such as, for example, the sequences listed in FIG. 12 and FIG. 13. Particularly useful metastatic sequences include TGF-$\beta$. A host animal with reduced levels of a metastatic gene product may be used to isolate novel metastatic genes. Host animals may be screened for reduced levels of metastatic gene expression. In addition, transgenic technology may be use to ablate a metastatic gene in the germline of a host animal.

Another embodiment of the invention is directed to analysis of a cell line before their use as a starting material to isolate metastatic genes in a particular pathway. Analysis is useful in identifying cells, and consequently sequences specific to these cells, which are particularly susceptible or resistant to metastatic transformation. For example, a cell highly predisposed to metastasis may be especially sensitive for detecting metastatic genes. Conversely, a cell showing high resistance to metastasis can be used to isolate especially potent metastatic sequences. One method to analyze susceptibility to metastasis is to determine the cellular response to growth factors or growth inhibitors. Briefly, a control population and a test population of cells are exposed to a growth factor or a growth inhibitor and the cellular response (e.g. proliferation, metabolism) recorded. Cells showing abnormal responses to the growth factor or growth inhibitor may be used as the starting material for metastatic gene isolation. Cellular response include changes in the rate of cellular division (e.g. thymidine uptake), changes in the expression of RNA or proteins, changes in cellular localization or modification patterns of RNA or proteins, and changes in the rate of uptake, release or metabolism of nutrients.

Figure 2A:
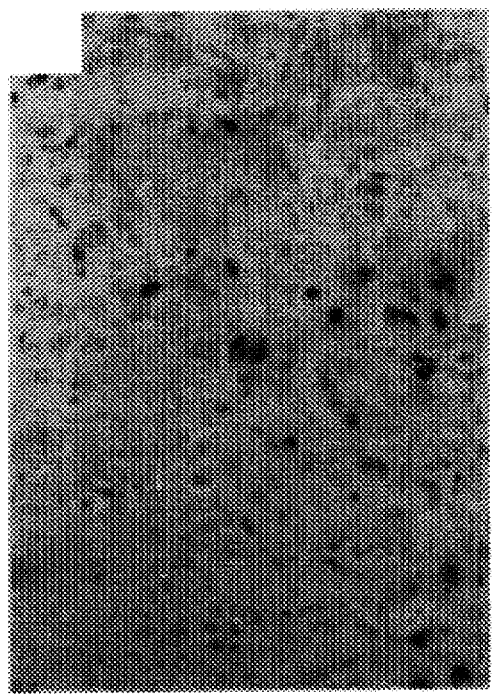
FIG. 2 A–B Staining of primary tumor (A) and metastatic deposit (B) from the lung of the same animal.
Figure 2B:
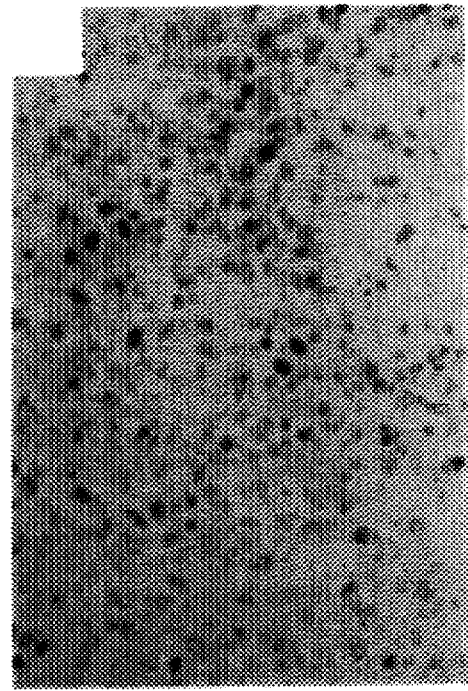
Figure 3A:
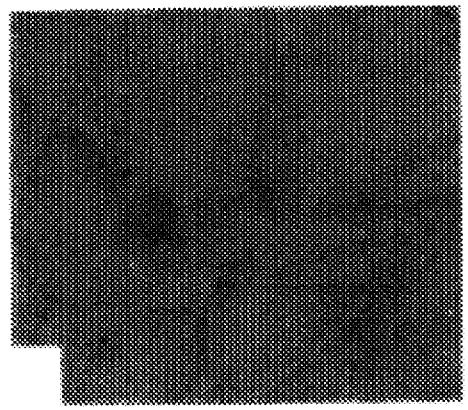
FIG. 3 A–D Staining of normal human prostate (A), moderately differentiated human prostate tumor (B and C), and poorly differentiated prostate tumor (D).
Figure 3B:
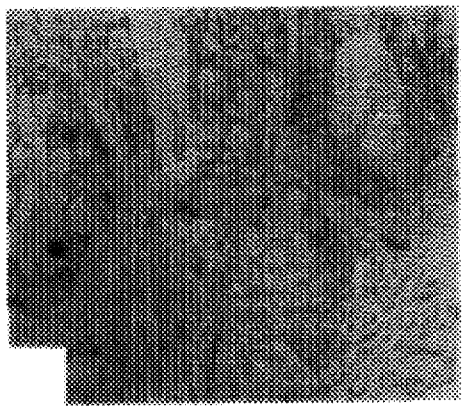
Figure 3C:
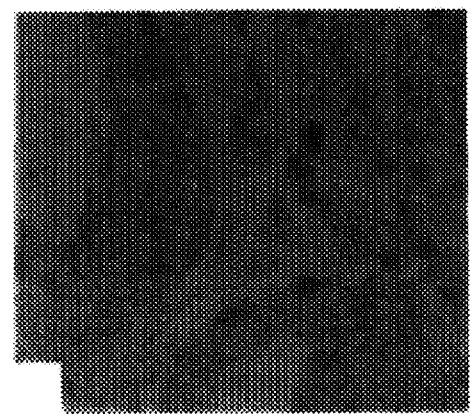
Figure 3D:
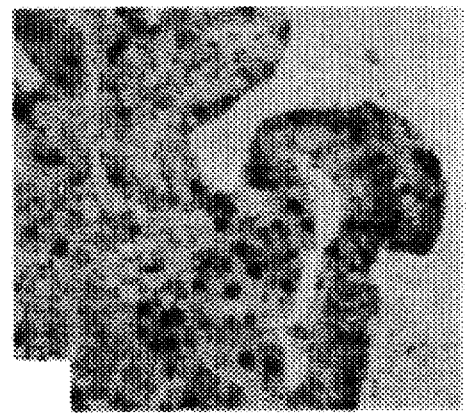

Especially potent or weak metastatic genes may be detected by treating and analyzing the metastatic potential of different cells and selecting a suitable cell type as the starting material. For example, cells may be treated with myc, ras, p53 or combinations thereof and analyzed for cyclin D1 expression which is shown to correlates with metastasis. FIG. 2 shows the in situ analysis of cyclin D1 in primary MPR tumors (FIG. 2A) and in metastatic deposits from the lung of the same animal (FIG. 2B). The gene expression pattern of cyclin D1 in MPR correlates with that of human prostate tumors (FIG. 3) analyzed with stains specific for cyclin D1 expression. Normal human tissue shows no cyclin D1 expression or staining (FIG. 3A). Moderately differentiated prostate cancers with dispersed (FIG. 3B) or focal positively staining (FIG. 3C) show moderate staining. Advanced poorly differentiated prostate cancer show strong nuclear as well as cytoplasmic staining (FIG. 3D) implying strong expression of cyclin D1. After treatment with myc, ras or p53, cyclin D1 expression shows correlation with the metastatic potential of the cell. Thus, cyclin D1 expressing cells are a source of cells with high metastatic potential. Conversely, cells with low cyclin D1 expression are a source of potentially metastatically resistant cells.

Figure 4:
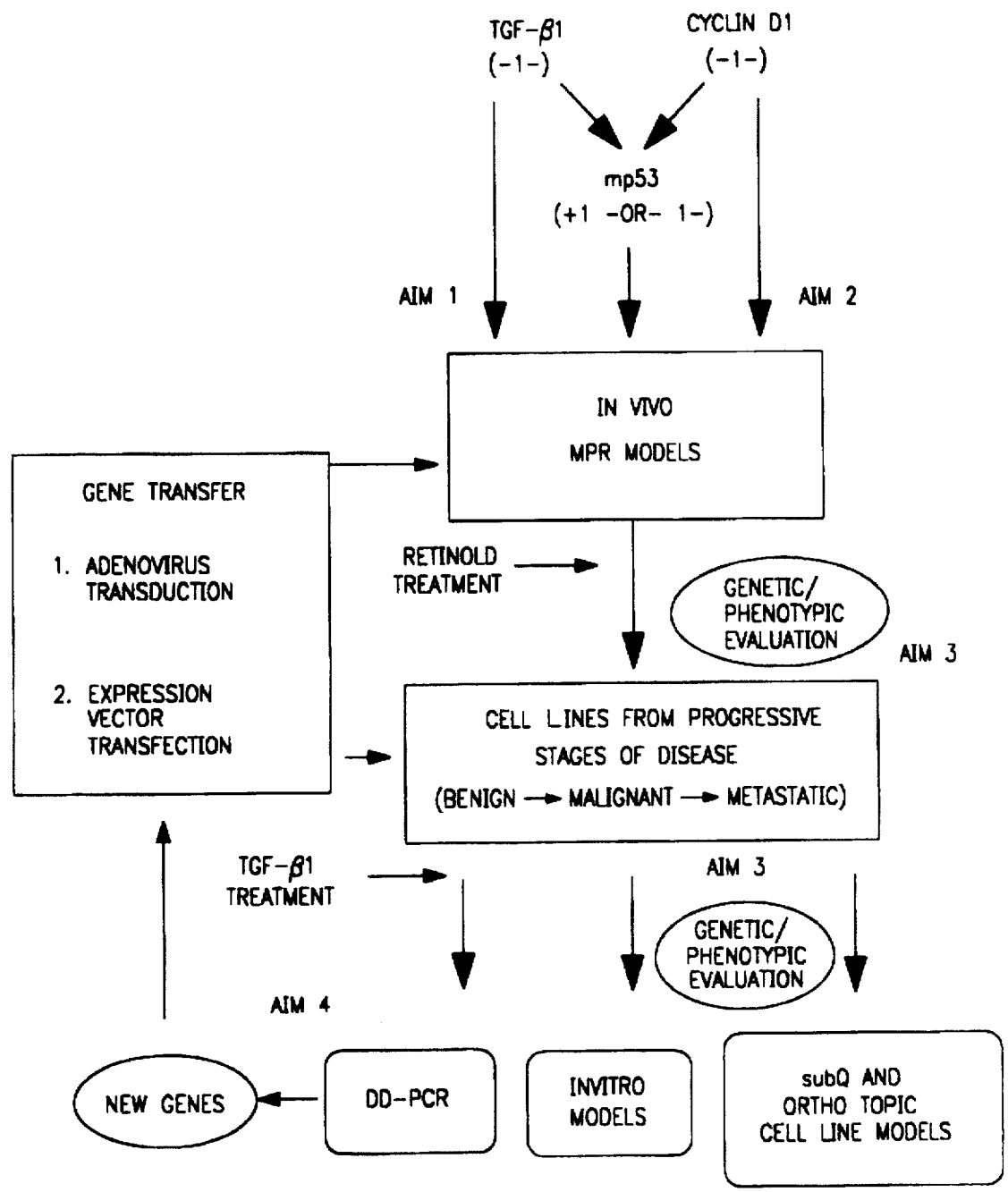
FIG. 4 Schematic of method for isolating a metastatic gene from a gene ablated mouse strain.

This method may be adjusted for the isolation of metastatic sequences expressed along a particular developmental or differentiation pathway by combining the various treatment and analytical techniques. This approach is schematically represented in FIG. 4. For example, a mammalian cell may be genetically ablated for TGF-β6, Cyclin D1, p53, lysyl oxidase, caveolin, actin binding protein, ubiquitin activating enzyme E1, nmb, α actinin 3, or p34. The genetically altered cell is used in an in vivo mouse prostate reconstitution (MPR) model. Metastatic and nonmetastatic cells isolated from the MPR may be analyzed directly or after induction with an agent such as the TGF-β gene or its product. Analysis involves the use of differential display polymerase chain reaction to identify differentially expressed bands. Sequences identified may be used for subsequent ablation, transformation or differential analysis.

Genetic ablation (gene knockout) may be performed after a cell is selected or by selecting a cell comprising a genotype with the proper genetic ablation. Cells already comprising gene ablation may be acquired from a cell depository, from other laboratories or from a transgenic animal. As transgenic animals comprise genetically ablated genes in every cell, any tissue from a transgenic animal may be used as the starting material.

The effects of oncogenes are at least additive and often synergistic. Thus, dominant oncogenes may be transfected together or multiple recessive oncogenes ablated together for a stronger effect. Furthermore, both methods may be combined and dominant oncogene transfection may be accompanied by recessive oncogene ablation.

The function of the metastatic sequence may be determined by the differential expression pattern. For example, a dominate metastatic gene will be present in a metastatic cell while a recessive metastatic gene is present in a non-metastatic cell. Metastatic sequences may be detected as bands which are present in the DD-PCR of metastases isolated in secondary sites and absent from DD-PCR products of primary cells. These sequences may be dominant metastatic genes whose expression is directly responsible for metastases, or they may be metastasis associated genes whose expression correlates with metastasis. Either are useful for therapy and diagnosis. Conversely, DD-PCR bands which are present in primary site tumors, but absent in secondary metastatic sites, may be dominant metastasis suppression genes. Dominant metastasis suppression genes comprise genes whose expression suppresses metastasis while nonmetastatic genes comprise genes whose expression correlates with non-metastatic tissue. Genes which are highly correlative with either the metastatic phenotype or the non-metastatic phenotype may be isolated. Isolation can be performed by cutting the appropriate nucleic acid in the band of a polyacrylamide gel or by collecting the appropriate fraction in an HPLC or capillary electrophoresis. The nucleic acid may be cloned into a plasmid vector, and sequenced, or synthetically prepared.

Figure 5B:
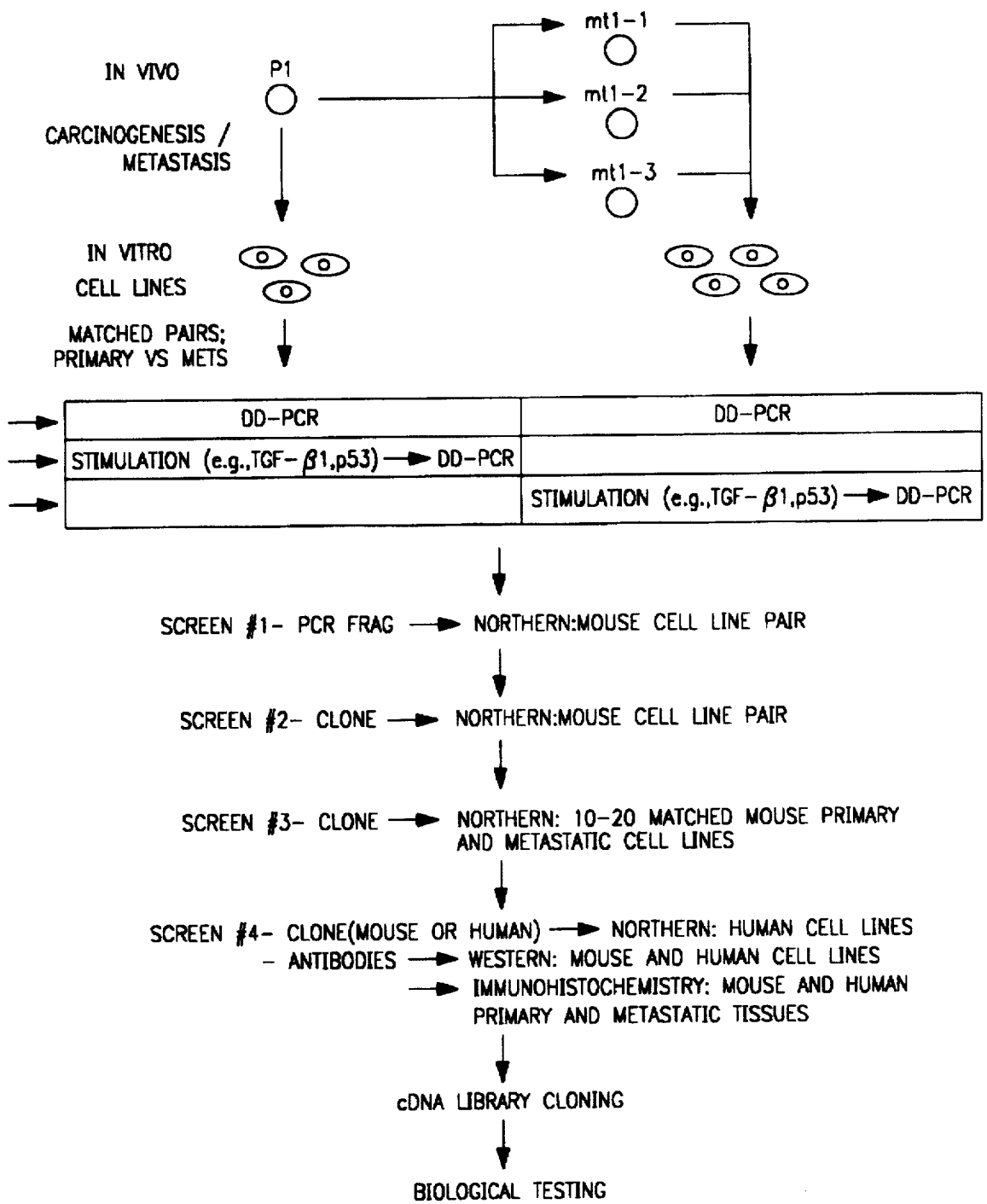

Another embodiment of the invention is directed to a method for identifying sequences in a metastatic pathway which are responsive or unresponsive to extracellular signals. Such sequences may be used in therapy and diagnosis of metastatic disorders. Implanted cells or cells from a primary site and cells from a secondary site are treated with extracellular signals. RNA sequences from the treated cells are compared with RNA sequences of the untreated cells (FIG. 5B). Treated cells and untreated cells may be derived from a short term or long term in vitro culture of primary tumors and malignant tumors. Alternatively, a part of a primary tumor and a part of a malignant tumor may be collected before the animal is treated with an extracellular cytokine or other factor. Long term cultures, or cell lines of primary and malignant cells may also be used as recipients of extracellular growth signal treatment. Suitable signals for each experiment will depend on the cell type. Generally, growth factors, lymphokines, inhibitory factors, migratory factors or hormones may be used. Factors previously isolated by commercial or methods of the invention and factors associated with or causative or suppressive of metastasis are preferred. Thus, transforming growth factor β1 (TFG-β1) may be used to treat cells before DD-PCR analysis. Proteins encoded by the genes isolated by this method are especially useful for the treatment of cells for the isolation of additional sequences. The identification of one sequence responsive to the extracellular signal pathway allows for identification of additional genes upstream and downstream from that sequence.

Another embodiment of the invention is directed to metastatic sequences identified by the methods of the invention. Metastatic sequences are sequences associated with the presence or absence of a metastasis or related to the metastatic process can be used in the therapeutic treatment of metastasis. Metastatic-related sequences include dominant metastatic sequences, recessive metastatic sequences, metastasis associated sequences, dominant oncogenes, recessive oncogenes and cell cycle genes. These genes encode for example, proteins involved in cell cycle, signal processing, DNA replication, growth regulation, inter and intra cellular signaling transcription control and translation control. Isolated sequences are useful in the treatment and for the detection of metastatic and other disorders. Disorders which may be treated comprise diseases involving proteins and sequences which are isolated by interaction with the sequences and proteins isolated by the method of the invention. Both malignant or nonmalignant disorders may be treated. Non malignant disorders include hyperplasia, dysplasia and hypertrophy. Examples of nonmalignant disorders include benign enlargement of the prostate, nodular hyperplasia, and benign prostatic hypertrophy.

Treatment may involve gene replacement, gene targeting, antisense inhibition, gene expression or gene suppression. Gene replacement involves replacing a copy of a defective gene with another copy by homologous recombination. Gene targeting involves the disruption of a cellular copy of a gene by homologous recombination. Antisense inhibition exploits the specificity of hybridization reactions between two complementary nucleic acid chains to suppress gene expression. Cloned genes can be engineered to express RNA from only one or the other DNA strands. The resultant RNA hybridizes to the sense RNA and inhibits gene expression. Gene expression and gene suppression involve the introduction of genes whose expression actively inhibits neoplastic transformation and metastasis.

Another embodiment of the invention is directed to nucleic acids which comprise a sequence identified by the methods of the invention. The nucleic acid may be DNA, RNA or PNA and may be used as a diagnostic tool in the treatment of neoplastic disorders and malignant tumors. The nucleic acids may comprise additional sequences such as promoters, for expression of a sense or antisense message, recombination sequences for gene targeting, selectable markers for transfections, or replication origins for passage in a prokaryotic or eukaryotic host such as animal cells, bacteria or yeast.

Another embodiment of the invention is directed to nucleic acids which comprise sequences identified by the method of the invention such as, for example, the caveolin, ABP280 (actin binding protein 280), the lysyl oxidase gene, and the nmb gene (clone 29), and other sequences listed in FIG. 12 and FIG. 13. Nucleic acids comprising a sequence corresponding to these genes may be used in treatment or diagnosis and in diagnostic kits for screening biological samples for the presence or absence of metastasis or metastatic potential. Treatment may involve using the sequences in gene therapy, including gene ablation, gene expression and antisense suppression. Diagnosis may involve genotypic analysis of samples to determine the existence and expression levels of the expressed sequences.

Another embodiment of the invention is directed to the use of caveolin gene and protein in the isolation of oncogenes and in the treatment of neoplastic disorders such as, for example, prostate cancer. Caveolin is an integral membrane protein and a principal component of caveolae. Caveolae are small invaginations at or near the plasma membrane of most smooth muscle cells and may function as a component of specific signal transduction pathways. Surprisingly, caveolin expression increases in metastatic human prostate cells as compared to human primary prostate tumors.

As caveolin expression correlates with metastasis, application of biological technologies designed to block the activity of caveolin or the function of caveolae may have therapeutic benefits for the treatment of neoplastic disorders such as human prostate tumors. Specific treatment approaches using caveolin may include the delivery of antisense or dominant negative caveolin sequences using expression or viral vectors; as well as the use of specific anti-caveolin antibodies. Additional approaches could also target the cavoeolae, but are not specifically based on caveolin function. Additional protein and non-protein components of caveolae could also be targeted for abrogation or the local or systemic administration of nutritional or biological agent may also be used. For example, caveolae are extremely rich in cholesterol and disruption or depletion of this molecule may alter the function of caveolae.

Another embodiment of the invention is directed to methods for treating a neoplastic disorder comprising administering a pharmaceutically effective amount of composition containing a nucleic acid having a sequence identified according to the methods of this invention, its expression product or fragments of either. The nucleic acid may be in the form of a sense or antisense single-stranded or double-stranded nucleic acid. The composition may be combined with a pharmaceutically acceptable carrier such as water, alcohols, salts, oils, fatty acids, saccharides, polysaccharides administered by injection, pulmonary absorption, topical application or delayed release. More than one carrier may be used together to create a pharmaceutical with desirable properties.

Another embodiment of the invention is directed to a kit or diagnostic acid for screening biological samples for detection of metastasis, neoplasia or kits comprise sequences isolated according to the methods of the invention and reagents and materials useful in such kits, such as, for example, buffers, salts, preservatives, and carriers, all of which are well known to those of ordinary skill in the art. Kits are useful for the analysis of tissues to screen those for the determination of normal, nonmalignant neoplastic or malignant cells. Kits may comprise additional reagents useful for the extraction of nucleic acids from a tissue sample. Reagents for analyzing the nucleic acid extracted from a tissue sample such as polymerase chain reaction reagents and Southern blots reagents may also be included.

The following experiments are offered to illustrate embodiments of the invention and should not be viewed as limiting the scope of the invention.

EXAMPLES

Example 1
Production of Mouse Prostate Reconstitution Tumors and Metastasis.

Mouse Urogenital Sinus (UGS) tissue was isolated from 17 day old mice embryos. Each isolated UGS was digested with 1% trypsin for three hours at 4° C. The trypsin was inactivated by the addition of fetal calf serum. UGS cells were digested with 0.125% collagenase for 1.5 hours, counted and mixed at the appropriate cell ratios prior to infection with retrovirus in the presence of polybrene. Retroviruses used include Zipras/myc-9. Control experiments were performed using BAGA virus. After a two-hour infection, the infected cells were centrifuged and individual reconstitutions containing $1.5 \times 10^6$ cells produced by resuspending the cells in rat tail collagen at a density of $6.0 \times 10^7$ cells per ml. Aliquots of the infected UGS cells were placed in (DME) with 10% fetal calf serum overnight at 37° C., 5% $CO_2$.

The next morning each cell/collagen reconstitution was implanted under the renal capsule of an adult male +/+ animal. Reconstitutions were harvested from the mice five weeks later when they showed signs of obvious distress from the tumor burden. Metastasized tumors were isolated from the same mice at sites outside the renal capsule. Isolated tumors and metastasises were either stored in liquid nitrogen or in preservatives such as 10% buffered formalin.

Cell lines were derived from fresh tumors by mincing a small portion of the primary and metastatic tumor and placing each in explant culture in Dulbecco's Modified Eagle Medium (DMEM) supplemented with 10% fetal calf serum. Cells which grow from each explant were propagated in DMEM and 10% fetal calf serum.

For histological analysis, a portion of a fresh tumor was fixed in 10% buffered formalin and embedded in paraffin for sectioning and staining with hematoxylin and eosin (H&E) or immunohistochemical staining. Immunohistochemical localization of cytokeratins was detected using polyclonal cytokeratin antiserum A575 (Dake Co.; Carpinteria, Calif.) and Vectastain ABC kit (Vector Laboratories; Burlingame, CA).

Example 2
Isolation of C-DNA for DD-PCR.

Total cellular RNA was isolated by ultracentrifugation through cesium chloride. Briefly, up to one gram of cells from culture, tumors or organs was placed into 4 ml of ice-cold GIT buffer (4M guanidine isothiocyanate, 0.025M sodium acetate, 0.1M M β-mercaptoethanol) and homogenized in a tissue homogenizer (Polytron or equivalent). The homogenate was carefully layered over 4 ml of 5.7M CsCl, 0.024M sodium acetate (1.8 g CsCl per ml) in a centrifuge tube. The layers were centrifuged at 35,000 RPM for 18 hours in a SW50.1 rotor. DNA was collected from the interface between the cushion and the supernatant, diluted two folds with water, added to 2.5 volumes of ethanol and spooled out on a glass rod. RNA that formed a pellet on the bottom of the CsCl layer was resuspended, and once extracted with an equal volume of phenol:chloroform (1:1), twice with chloroform and precipitated with ethanol and resuspended in diethylpyrocarbonate treated water. The concentration of DNA and RNA were be determined by absorption at 260 nanometers.

Example 3
Differential Display Polymerase Chain Reaction.

mRNA isolated from primary tumors or metastasis was reverse transcribed with one of the primers and subjected to DD-PCR using the same primer as both the forward and reverse primer. A set of 24 primers comprising short oligonucleotides were used for both the reverse transcription of mRNA into c-DNA and for differential display polymerase chain reaction. The sequence of the primers used are shown in Table 1.

TABLE 1

| Primer No. | Sequence | Sequence number |
|---|---|---|
| 1 | 5'-TGACAATCG-3' | (SEQ. ID. NO. 1) |
| 2 | 5'-AGCTAAGGTC-3' | (SEQ. ID. NO. 2) |
| 3 | 5'-TCTGCGATCC-3" | (SEQ. ID. NO. 3) |
| 4 | 5'-ATACCGTTGC-3' | (SEQ. ID. NO. 4) |
| 5 | 5'-TACGAAGGTG-3' | (SEQ. ID. NO. 5) |
| 6 | 5'-TGGATTGGTC-3' | (SEQ. ID. NO. 6) |
| 7 | 5'-CTTTCTACCC-3' | (SEQ. ID. NO. 7) |
| 8 | 5'-GGAACCAATC-3' | (SEQ. ID. NO. 8) |
| 9 | 5'-TGGTAAAGGG-3' | (SEQ. ID. NO. 9) |
| 10 | 5'-TCGGTCATAG-3' | (SEQ. ID. NO. 10) |
| 11 | 5'-CTGCTTGATG-3' | (SEQ. ID. NO. 11) |
| 12 | 5'-GATCAAGTCC-3' | (SEQ. ID. NO. 12) |
| 13 | 5'-GATCCAGTAC-3' | (SEQ. ID. NO. 13) |
| 14 | 5'-GATCACGTAC-3' | (SEQ. ID. NO. 14) |
| 15 | 5'-GATCTGACAC-3' | (SEQ. ID. NO. 15) |
| 16 | 5'-TTAGCACCTC-3' | (SEQ. ID. NO. 16) |
| 17 | 5'-ACCTGCATGC-3' | (SEQ. ID. NO. 17) |
| 18 | 5'-GCTATACTGC-3' | (SEQ. ID. NO. 18) |
| 19 | 5'-AGTTGCCAGG-3' | (SEQ. ID. NO. 19) |
| 20 | 5'-AAGCCGTGTC-3' | (SEQ. ID. NO. 20) |
| 21 | 5'-TCAACGCTCA-3' | (SEQ. ID. NO. 21) |
| 22 | 5'-TGTTCGAATC-3' | (SEQ. ID. NO. 22) |
| 23 | 5'-CGAGTCAGAC-3' | (SEQ. ID. NO. 23) |
| 24 | 5'-TATGAGTCCG-3' | (SEQ. ID. NO. 24) |

Figures 6A, 6B:
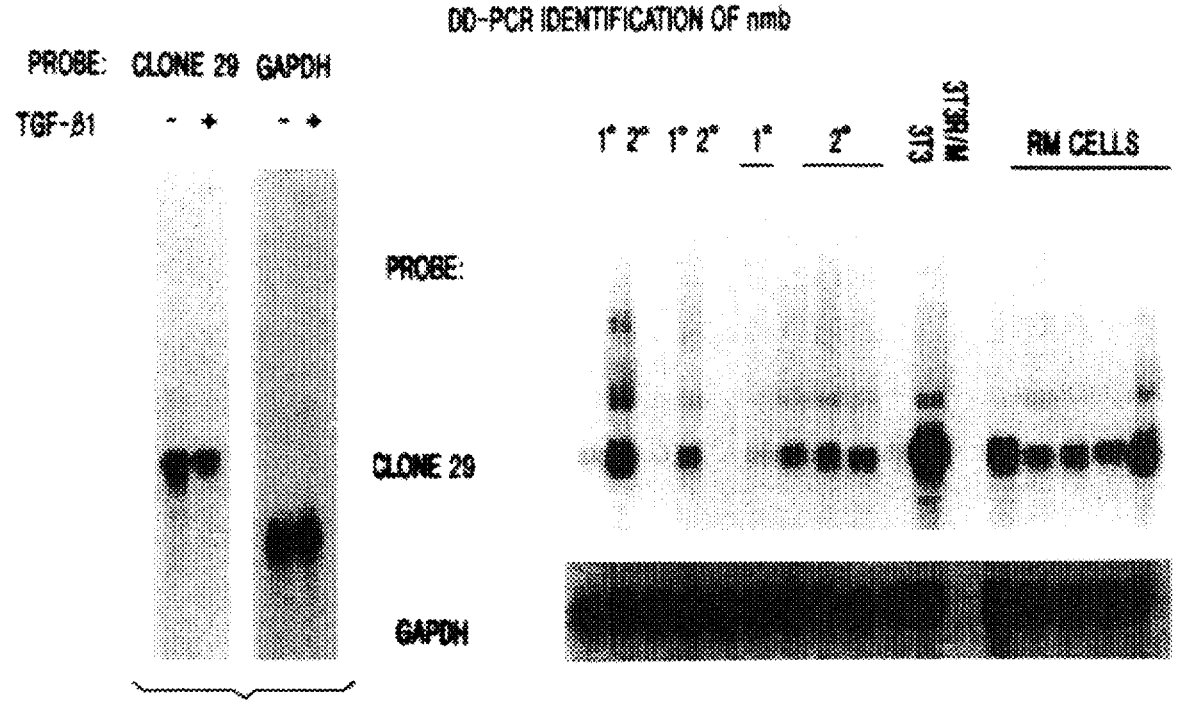
FIG. 6 Isolation and characterization of nmb gene expression by DD-PCR and RNA blot in primary and metastatic cells.
Figures 7A, 7B:
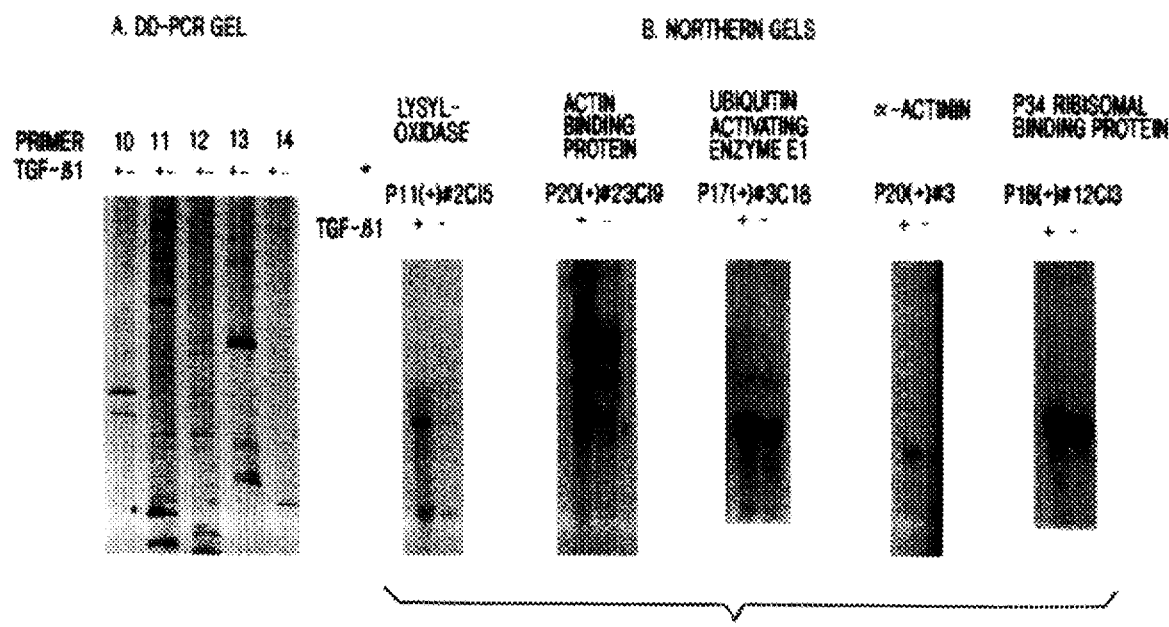
FIG. 7 Differential expression of multiple genes is determined by DD-PCR and RNA blot of primary and metastatic cells.
Figure 8:
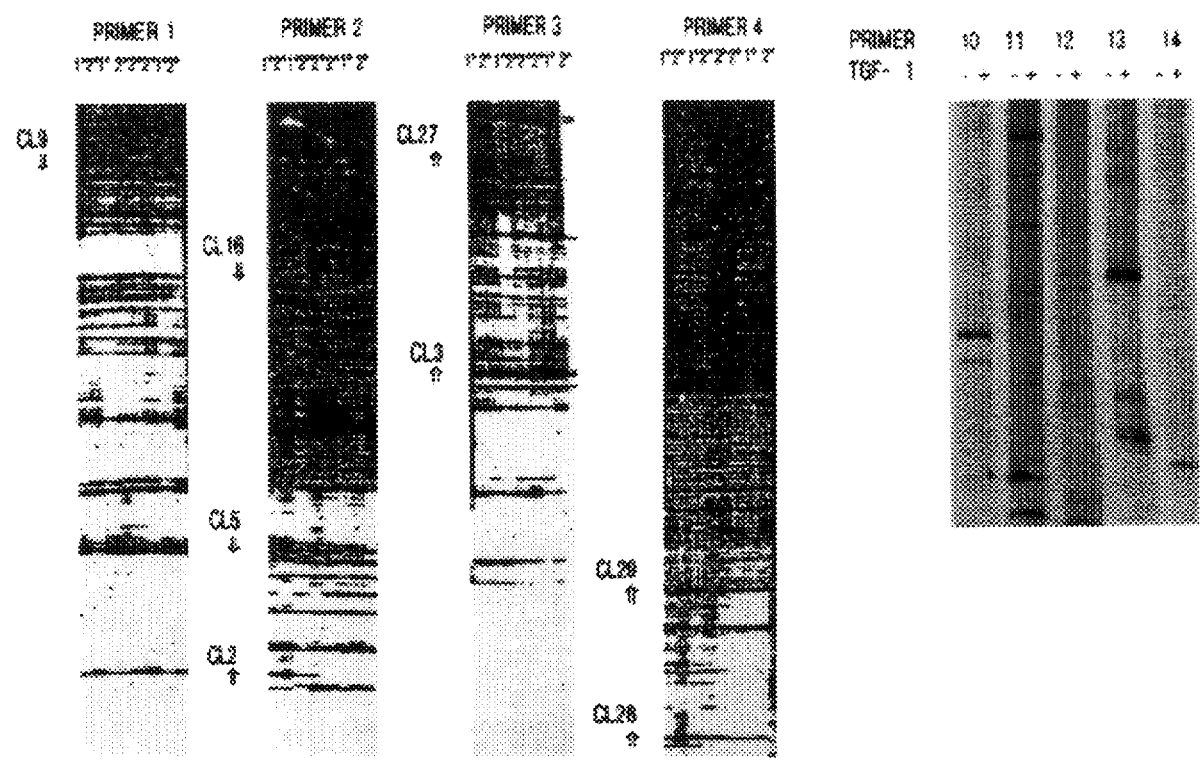
FIG. 8 Caveolin identified as a differentially expressed gene by DD-PCR.
Figure 9:
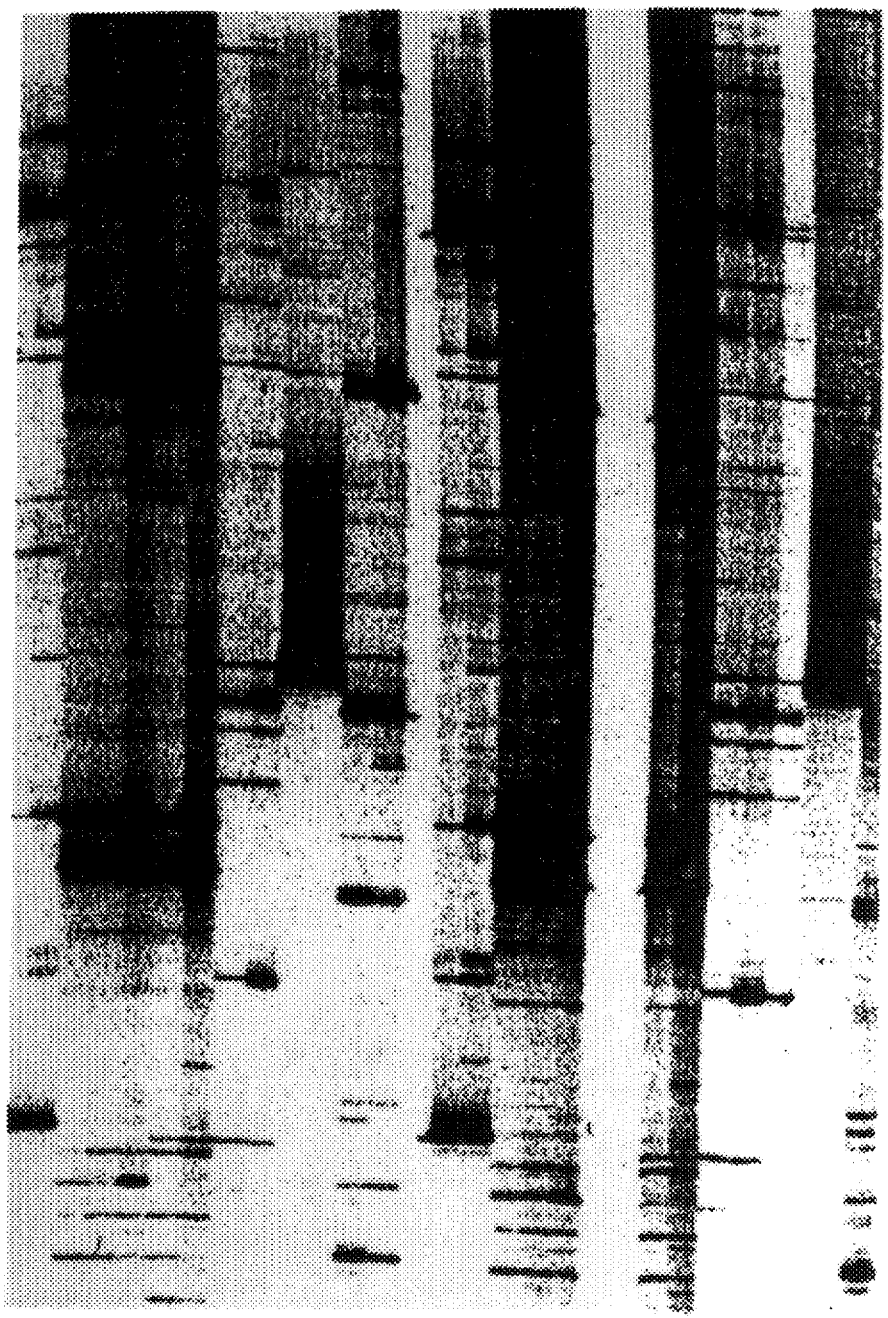
FIG. 9 Differential expression of genes isolated by DD-PCR confirmed by RNA blots.

PCR was performed using standard conditions with 40 cycles of denaturation at 94° C. for 40 seconds, annealing at 40° C. for 2 minutes, and elongation at 72° C. for 35 seconds. After PCR, the products were analyzed with non-denaturing polyacrylamide gel electrophoresis (PAGE) at 12 watts for 15 hours. Bands which differed between test and control samples were eluted from the gel, subjected to reamplification by PCR and cloned. Polyacrylamide gel electrophoresis of DD-PCRs, and the accompanying RNA blot analysis showing the isolation of sequences with substantial similarity to nmb and TGF-β is shown in FIG. 6 and FIG. 7 respectively. Additional sequences isolated by this method show substantial similarity to lysyl oxidase, actin binding protein, ubiquitin activating enzyme E1, α-actinin, and P34 ribosomal binding protein sequence (FIG. 8). Differential expression of caveolin was demonstrated by DD-PCR followed by PAGE (FIG. 9).

Example 4
p53 Allelotype Determination.

The p53 allelotype of a cell sample was determined by PCR. Briefly, nucleic acid is extracted from a tissue sample or a cell culture sample. An aliquot of nucleic acids in placed in 45 μl aliquot of a master mix which contained a final concentration of 0.2 mM of each dATP, dTTP, dGTP, dCTP, 1.5 mM MgCl$_2$, 0.5 unit Taq polymerase, 0.05 μM of each of two primers set specific for the normal wildtype allele of p53 (5'-GTGTTTCATTAGTTCCCCACCTTGAC-3', SEQ. ID NO. 25; 5'-AGAGCAAGAATAAGTCAGAAGCCG-3', SEQ. ID NO. 26). A control set of primers specific for the fibroblast growth factor-7 gene was used to monitor the polymerase chain reaction experiment (5'-ACAGACCGTGCTTCCACCTCGTC-3', SEQ. ID NO. 27; 5'-CCTCATCTCCTGGGTCCCTTTCA-3', SEQ. ID NO.28). One μl of the reaction from the first round of PCR was used as the starting material for a second round of PCR using a second set of wildtype p53 specific primer (5'-GTCCGCGCCATGGCCATATA-3', SEQ. ID NO. 29; 5'-ATGGGAGGCTGCCAGTCCTAACCC-3', SEQ. ID NO. 30). This second round of PCR was also monitored using a control set of primers specific for the fibroblast growth factor-7 (5'-ACAGACCGTGCTTCCACCTCGTC-3', SEQ. ID NO 27; 5'-CCTCATCTCCTGGGTCCCTTTCA-3', SEQ. ID NO 28).

After PCR the products were analyzed with non-denaturing polyacrylamide gel electrophoresis (PAGE) at 12 watts for 15 hours. Bands which differed between test and control were eluted from the gel, subjected to reamplification by PCR and cloned.

Example 5
Induction of cell lines with TGFβ6 Influence Cellular Gene Expression.

1481-PA cells were grown overnight in DME supplemented with 10% fetal calf serum overnight at 37° C., and 5% $CO_2$. Induction was performed by treatment with TGF-β1 at a concentration of 2 nanograms per ml. The treated cells were returned to the incubator and cultured for 12 hours. After induction, cells were washed in phosphate buffered saline and harvested and concentrated by centrifugation.

Figure 10:
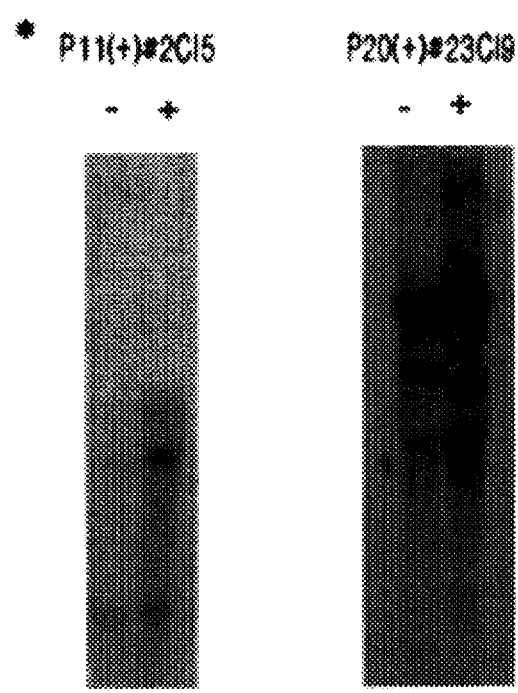
FIG. 10 RNA blot analysis of total tumor mRNA using clone 29 GADPH probes.

RNA was extracted from treated and untreated cells and subjected to DD-PCR. Differentially expressed bands detected by DD-PCR were cloned and differential expressions were confirmed using RNA blots (FIG. 10). Subsequent cloning and sequencing identified the bands as ABP280 or filamin.

Figure 11:
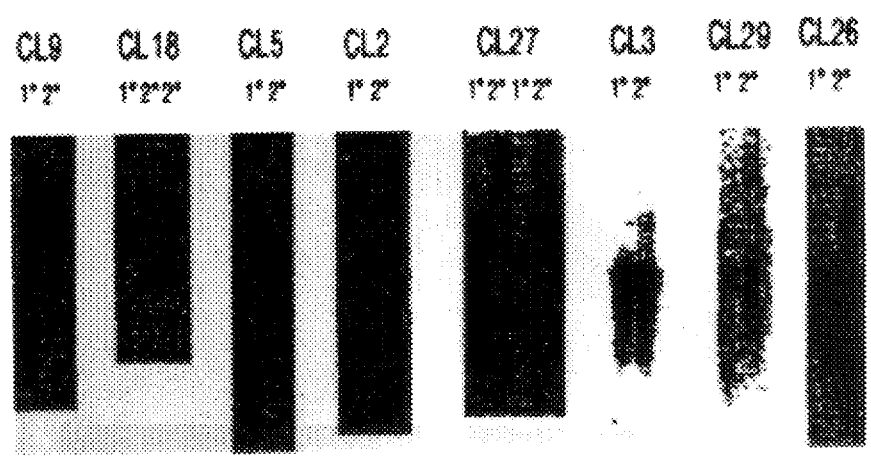
FIG. 11 RNA blot of three independent MPR metastatic tumors and 5 MPR non-metastatic tumors.

One gene isolated showed differential expression in cells induced by TGF-β (FIG. 11, clone 29), while a control probe on the same cell line showed no difference in expression levels (FIG. 11, GAPDH).

Example 6
Metastatic Sequences Isolated.

Using the methods of Examples 1, 2, 3, 4, and 5, a plurality of metastatic sequences were isolated and sequenced. The expression of the metastatic sequences in primary cells and in metastatic cells were determined using RNA blots. The nucleic acid sequences of other isolated sequences are listed in FIG. 12. Sequence analysis and expression analysis was performed on the isolated cloned and the results of these studies are summarized in FIG. 13.

Example 7
Caveolin Immunoassay in Human Prostate Cancers.

Primary site human prostate tumors and metastases were isolated and analyzed for caveolin expression by immunoassay. The results of the assay is shown in Table 3. Metastases shows higher levels of caveolin proteins in metastases than in primary tumors. Immunohistology of tissue sections reveals both elevated levels and distinct distribution of caveolin protein in metastatic human prostate when compared to a primary human prostate tumor (FIG. 14).

TABLE 3

| Patients | Primary-site | Metastases in lymph node |
|---|---|---|
| 1 | + | ++ |
| 2 | ++ | +++ |
| 3 | ++ | +++ |
| 4 | ++ | ++ |
| 5 | + | + |
| 6 | ++ | ++ |
| 7 | ++ | +++ |
| 8 | + | + |
| 9 | − | − |
| 10 | + | + |
| 11 | + | + |
| 12 | ++ | ++ |
| 13 | + | + |
| 14 | ++ | +++ |

Other embodiments and uses of the invention will be apparent to those skilled in the art from consideration of the specification and practice of the invention disclosed herein. The specification and examples should be considered exemplary only with the true scope and spirit of the invention indicated by the following claims.

I claim:

1. A method for identifying a sequence expressed in a metastasis comprising the steps of:

a) transfecting an oncogenic sequence into a mammalian cell to form a population of transfected cells;

b) administering tranfected cells to a primary site of a host mammal to form a primary tumor;

c) maintaining said mammal for a period of time sufficient to develop a metastasis at a secondary site;

d) amplifying expressed RNA sequences of the transfected cells and expressed RNA sequences of the metastasis by differential-display PCR; and e) comparing the amplified expressed RNA sequences of the transfected cells with the amplified expressed RNA sequences of the metastasis and identifying the sequence expressed at a higher level in the metastasis as compared to the expressed RNA sequences of the transfected cells.

2. The method of claim 1 wherein the mammalian cell is transfected by calcium phosphate transfection, viral transduction, lipofection, dextran sulfate transfection or electroporation.

3. The method of claim 1 wherein the oncogenic sequence is a sequence of the gene that erodes the oncoproteins p21, p34, p53, myc, ras or src.

4. The method of claim 1 wherein the oncogenic sequence is a sequence that enhances metastatic potential.

5. The method of claim 4 wherein the oncogenic sequence is a sequence of the gene that encodes cyclin D1, caveolin or TGF-β1.

6. The method of claim 1 wherein the mammalian cell is treated with an agent that alters gene expression prior to the administration of said cell to said host mammal.

7. The method of claim 6 wherein the agent is benzanthracene (BA), dimethyl benzanthracene (DMBA) or 5-azacytidine.

8. The method of claim 1 wherein the mammalian cell is a primary cell or an established cell line.

9. The method of claim 1 wherein the mammalian cell is isolate from urogenital sinus tissue.

10. The method of claim 1 wherein the mammalian cell is a fetal cell.

11. The method of claim 1 wherein the mammalian cell contains a gene selected from the group consisting of TGF-β1, cyclin D1, p21, p34, p53, ras, and myc.

12. The method of claim 1 wherein the mammalian cell is isolated from the same species as the host mammal.

13. The method of claim 1 wherein the mammalian cell and the host mammal are histocompatible.

14. The method of claim 1 wherein the mammalian cell and the host mammal are syngeneic.

15. The method of claim 1 wherein the transfected cell is isolated and maintained in vivo or in vitro for a period of time prior to introduction of said cell to the host mammal.

16. The method of claim 1 wherein the expressed sequences of the transfected cells are obtained from a cell line of immortalized transfected cells.

17. The method of claim 1 wherein the transfected cells are administered to the primary site by subcutaneous implantation.

18. The method of claim 1 wherein the host mammal is a mouse, a rabbit or a primate.

19. The method of claim 1 wherein the host mammal is a syngeneic, xenogeneic, immunocompromised or transgenic host mammal.

20. The method of claim 1 further comprising suppressing expression of TGF-β in the host mammal prior to the introduction of transfected cells into said host mammal.

21. The method of claim 1 wherein the primary site is the renal capsule, the prostate or the testis.

22. The method of claim 1 wherein the secondary site is selected from the group of sites consisting of lung, kidney, liver, lymph nodes, brain, bone, testis, spleen, ovaries and mammary.

23. The method of claim 1 wherein differential display PCR is performed with an anchor primer and a variable primer.

24. The method of claim 22 wherein the anchor primer comprises a polythymidine sequence and a dinucleotide sequence connected to a 3'-terminus.

25. The method of claim 24 wherein the polythymidine sequence comprises between about 5 to about 30 thymidines.

26. The method of claim 24 wherein the dinucleotide sequence is selected from the group of sequences consisting of AA, AG, AC, AT, GA, GG, GC, GT, CA, CG, CC and CT.

27. The method of claim 23 wherein the anchor primer or the variable primer comprise a detectable moiety selected from the group consisting of radioactive moieties, phosphorescent moieties, magnetic moieties, luminescent moieties and conjugatable moieties.

28. The method of claim 23 wherein the anchor primer and the variable primer have a common sequence.

29. The method of claim 7 wherein the agent is a retinoid.

30. A method for identifying a sequence expressed in metastasis comprising the steps of:
  a) pretreating a mammalian cell with an agent that enhances metastatic potential to form a population of cells predisposed to metastasis;
  b) introducing the pretreated cells to a primary site of a host mammal;
  c) maintaining said mammal for a period of time sufficient to develop a metastasis at a secondary site;
  d) amplifying expressed RNA sequences of pretreated cells and expressed RNA sequences of the metastasis by differential-display PCR; and
  e) identifyg the sequence expressed at a higher level in the metastasis as compared to expressed RNA sequences of the pretreated cells.

31. The method of claim 30 further comprising the step of treating cells of the primary or secondary sites with a genotoxic agent prior to amplification.

32. The method of claim 31 wherein the genotoxic agent is benzanthracene (BA), dimethyl benzanthracene (DMBA) or 5-azacytidine.

33. The method of claim 30 further comprising the step of comparing the expressed sequences amplified from the metastasis with expressed sequences amplified from mammalian cells before pretreatment to identify the sequence selectively expressed in the metastasis.

34. The method of claim 30 wherein the chemical compound is a benzanthracene, dimethyl benzanthracene, or 5-azacytidine.

35. The method of claim 30 wherein the mammalian cell is transfected, prior to the administration of said cell to the host mammal, with an oncogenic sequence before or after treatment of said cell with the agent that enhances metastatic potential.

36. The method of claim 30 wherein the mammalian cell is a cell line.

37. The method of claim 30 wherein the mammalian cell is isolated from lymphatic tissue, hematopoietic cells, reproductive tissues or urogenital sinus tissue.

38. The method of claim 30 wherein the mammalian cell is a fetal cell.

39. The method of claim 30 wherein the mammalian cell is isolated from a transgenic animal.

40. The method of claim 30 wherein the primary site is the renal capsule, the prostate or the testis.

41. The method of claim 30 wherein the secondary site is selected from the group of sites consisting of lung, kidney, liver, lymph nodes, brain, bone, testis, spleen, ovaries and mammary.

42. The method of claim 30 wherein differential display PCR is performed using an anchor primer and a variable primer.

* * * * *